United States Patent [19]

Kaddurah-Daouk et al.

[11] Patent Number: 5,324,731
[45] Date of Patent: Jun. 28, 1994

[54] METHOD OF INHIBITING TRANSFORMATION OF CELLS IN WHICH PURINE METABOLIC ENZYME ACTIVITY IS ELEVATED

[75] Inventors: Rima Kaddurah-Daouk, Watertown; James W. Lillie, Somerville; Jonathan J. Burbaum, Cambridge, all of Mass.

[73] Assignee: Amira, Inc., Cambridge, Mass.

[21] Appl. No.: 610,418

[22] Filed: Nov. 7, 1990

Related U.S. Application Data

[63] Continuation-in-part of Ser. No. 467,147, Jan. 18, 1990, abandoned, which is a continuation-in-part of Ser. No. 344,963, Apr. 28, 1989, abandoned, which is a continuation-in-part of Ser. No. 310,773, Feb. 14, 1989, abandoned.

[51] Int. Cl.$^5$ .................... A01N 43/54; A01N 43/50; A61K 31/415; A61K 31/505
[52] U.S. Cl. .................................. 514/275; 514/385; 514/386; 514/396; 514/553; 514/561; 514/563; 514/564; 514/579; 514/631; 514/638; 514/646
[58] Field of Search .............. 514/275, 385, 386, 396, 514/553, 561, 563, 564, 579, 631, 638, 646

[56] References Cited

PUBLICATIONS

El Hiyani, L. et al., *Biological Abstracts*, 84(9): AB-729, No. 89661 (1987). and *Chem.-Biol. Interactions*, 62: 167–178 (1987).
Toleikis, A. I. et al., *Biological Abstracts*, 86(11): AB-170, No. 110912 (1988) and *Biokhimiya*, 53(4): 649–654 (1988).
Moss, R. J. et al., *J. Med. Chem.*, 31: 786–790 (1988).
Kappler, F. et al., *J. Med. Chem.*, 25: 1179–1184 (1982).
Miranda, A. F. et al., *Proc. Natl. Acad. Sci., USA*, 80: 6581–6585 (1983).
Rubery, E. D. et al., *Biological Abstracts*, 76(5): 3844, No. 35410 (1983) and *Eur. J. Cancer Clin. Oncol.* 18(10): 951–956 (1982).
Gazdar, A. F. et al., *Biological Abstracts*, 805: AB-578, No. 578, No. 41779 (1985) and *Cancer Res.*, 45(6): 2924–2930 (1985).
van der Krol., A. R., J. N. M. Mol, and A. R. Stuitje, *BioTechniques*, 6(10): 958–976 (1988).
Maker, H. S. et al., *Biological Abstracts*, 78(2): 1470, No. 12908 (1984), and *Res. Comm. Chem. Pathol. Pharmacol.*, 40(3): 355–366 (1983).
Daouk, G. H. et al., *J. Biol. Chem.*, 263(5): 2442–2446 (Feb. 15, 1988).
Lillie, J. W. et al., *Cell*, 50: 1091–1100 (1987).
Inhorn, L. et al., *Biological Abstrcats*, 86(2): AB-700, No. 17059 (1988) and *Blood*, 71(4): 1003–1011 (1988).
Rivedal, E. and T. Sanner, *Chemical Abstracts*, 103(9): 50, No. 153568m (1985) and *Cancer Lett.*, 28(1): 9–17 (1985).
Folbergrova, J. et al., *Biological Abstracts*, 84(2): AB-684, No. 17158 (1987) and *Neoplasma*, 34(1): 3–14 (1987).
Mariman, E. C. M. et al., *Genomics*, 1:126–137 (1987).
Mariman, E. C. M. et al., *Nucl. Acids Res.*, 17: 6385 (1989).
Zerler, B. et al., *Mol. Cell. Biol.*, 7: 821–829 (1987).
Shields, R. P. et al., *Lab. Invest.*, 33: 151–158 (1975).
McLaughlin, A. C. et al., *J. Biol. Chem.*, 247: 4382–4388 (1972).
Johnston, J. B. et al., *Cancer Res.*, 46: 2179–2184 (1986).
Kaddurah-Daouk, R. et al., *Mol. Cell. Biol.*, 10(4): 1476–1483 (1990).

(List continued on next page.)

*Primary Examiner*—Nathan M. Nutter
*Attorney, Agent, or Firm*—Lahive & Cockfield

[57] ABSTRACT

A method of inhibiting growth, transformation and/or metastasis of mammalian cells, particularly epithelial cells, in which activity of at least one enzyme, which participates in purine metabolism or regulation of nucleotide levels or the relative ratios of their phosphorylated states, is elevated. In particular, a method of inhibiting transformation, growth and/or metastasis of mammalian cells in which a DNA tumor virus, a DNA tumor virus factor or other factor which has an equivalent effect on cells has acted.

17 Claims, 39 Drawing Sheets

OTHER PUBLICATIONS

Feld, R. and Witte, D. L., *Clin. Chem.,* 23(10): 1930-1932 (1977).

Annesley, T. M. and J. B. Walker, *J. Biol. Chem.,* 253: 8120-8125 (1978).

Silverman, L. M. et al., *Clin. Chem.,* 25(8): 1432-1435 (1979).

Gazdar, A. F. et al., *Cancer Res.,* 41: 2773-2777 (1981).

Carney, D. N. et al., *Cancer Res.,* 44: 5399-5403 (1984).

Carney, D. N. et al., *Cancer Res.,* 45: 2913-2923 (1985).

Lillie, J. W. et al., *Cell,* 46: 1043-1051 (1986).

Moran, E. and M. B. Mathews, *Cell,* 48: 177-178 (1987).

White, P. et al., *Nature,* 334: 124-129 (Jul. 1988).

Kaye, F. J. et al., *J. Clin. Invest.,* 79: 1412-1420 (1987).

Phelps, W. C. et al., *Cell* 53: 539-547 (May, 1988).

Phelps, W. C. et al., Functional and Sequence Similarities Between HPV-16 E7 and Adenovirus E1A, In: *Transforming Proteins of DNA tumor Viruses,* Current Topics in Microbiol. and Immunol., vol. 144, (1989), R. Knippers and A. J. Kevine (Eds.), Springer-Verlag, Berlin, pp. 153-166.

von Knebel Doeberitz, M. et al;, *Cancer Res.,* 48: 3780-3786, (Jul. 1988).

Kleinheinz et al., Human Papillomavirus Early Gene Products and Maintenance of the Transformed State of Cervical Cancer Cells In Vitro, In: *Transforming Proteins of DNA Tumor Viruses,* Current Topics in Microbiol. and Immunol., vol. 144, (1989), R. Knippers and A. J. levine (eds.), Springer-Verlag, Berlin, pp. 179-179.

Dyson, N. et al., *Science,* 243: 934-937 (Feb. 17, 1989).

Ch'ng, J. L. C. et al., *Proc. Natl. Acad. Sci, U.S.A.,* 86: 10006-10010 (Dec. 1989).

Colberg-Poley, A. M. and Santomenna, L. D., *Virology,* 166(1):217-228 (1988).

Ishiguro, Y. et al., *Cancer,* 65: 2014-2019 (May 1990).

FIG. 3

B ISOZYME

```
CGCGGCGCGGCCAATGAATGGGCTATAAATAGCCCGGTGTGCCCTTAAGAGAGCCGGGAGCGCGGAGAGCGGCC
   |||||||||||       ||||||||||||||  |||||||||||||  ||||||||||||||||||||
-90        -80       -70        -60       -50        -40       -30        -20        -10
```

EIIaE

```
GGGTGTGGCCGCTGGAGATGACGTAGTTTTCGCGCTTAAAATTTGAGAAAGGGGCGAAACTAGTCCTTAAGAGTCAGCGCGCAGTATTTGCTGA
-90        -80       -70        -60       -50        -40       -30        -20        -10
```

(-90→-63)   (-63→-50)   (-48→-36)   (-30→-19) (-19→-11)
   IV          III          II          I         V

Sequence of phckl1lf

```
  1  CAGATCGAAA CGCTCTTCAA GTCTAAGAAC AACTACGAGT TCATGTGGAA CCCTCACCTG
 61  GGCTACATCC TCACCTGCCC CTCCAACCTG GGCACGGGGC TGCGGGCAGG CGTGCACATC
121  AAGCTGCCCC ACCTGGGCCA GCACCAGAAG TTCTCCCAGG TGCTCAAGCG GCTGCGGCTT
181  CAGAAGCGAG GCACAGGTGA GCAGGGCAGG TGCTGCGGCT TCCCGTGGCC TTTGGGCAGC
241  CCTGTTTCCT CCGCCCTGAC TTGCTGTCCC CAGGCGGTGT GGACAAGGCT GCGGTGGGCG
301  GGGTCTTCGA CGTCTCCAAC GCTGACCGCC TGGGCTTCTC AGAGGTGGAG CTGGTGCAGA
361  TGCTGGACGG AGTGAAGCTG CTCATCGAGA TGGAACAGCG GCTGGAGCAG GGCCAGGCCA
421  TCGACGACCT CATGCCCTGC CAGAAATGAA GCCCGGCCCA CACCGACACA GCCCTGCTGC
481  TTCCTAACTT ATTGCCTgGG CAGTGCACCA TGCACCCTGA TGTTCGCCGT CTGACGCCCT
541  TAGCCCTTGCT GTAGAGACTT cCGTCACCTT GGTAGAGTTT ATTTTtGAT
```

Sequence displayed from position 1 to end (position 589)
Sequence numbered from position 1

FIG. 7

METHOD OF INHIBITING TRANSFORMATION OF CELLS IN WHICH PURINE METABOLIC ENZYME ACTIVITY IS ELEVATED

FUNDING

The government has rights in this invention pursuant to grant Number NIH-5-R01-GM34366 awarded by the National Institutes of Health. Work described herein was also sponsored in part by NSF grant Number DMB-84-51645, from the National Science Foundation.

RELATED APPLIATIONS

This application is a continuation-in-part of U.S. Ser. No. 07/467,147, filed Jan. 18, 1990, entitled METHOD OF INHIBITING TRANSFORMATION OF CELLS IN WHICH PURINE METABOLIC ENZYME ACTIVITY IS ELEVATED, by Rima Kaddurah-Daouk and now abandoned which is a continuation-in-part of U.S. Ser. No. 07/344,963, filed Apr. 28, 1989, entitled "ALTERATION OF ONCOGENIC OR VIRAL ACTIVATION OF CELLULAR GENES INVOLVED IN ADENOSINE METABOLIC PATHWAYS" by Rima Kaddurah-Daouk, Ghaleb Daouk, Paul R. Schimmel, Robert Kingston James W, Lillie, Michael Green and Scott D. Putney and now abandoned which is a continuation-in-part of U.S. Ser. No. 07/310,773, filed Feb. 14, 1989, entitled "REGULATION OF EXPRESSION OF A GENE FOR ENERGY METABOLISM BY DOMAIN II OF THE ADENOVIRUS E1A GENE" by Rima Kaddurah-Daouk, Ghaleb Daouk, Paul R. Schimmel, Robert Kingston, James W. Lillie, Michael Green and Scott D. Putney and now abandoned. The teachings of the above-identified applications are incorporated herein by reference.

BACKGROUND

Transformation, or malignant transformation, of cells results in changes in their growth characteristics and can cause them to form tumors in animals into whom they are introduced. For example, transformation of adherent cells can be associated with alterations such as changes in growth control, cell morphology, membrane characteristics, protein secretion and gene expression. Although transformation can occur spontaneously, it can be caused by a chemical or irradiation or may result from infection by a tumor virus. Little is known about the underlying molecular events. One type of RNA viruses (the retroviruses) and many different types of DNA viruses can act to transform cells and collectively are referred to as tumor viruses. In the case of tumor viruses, it is clear that the virus does not itself carry all of the genes necessary to produce the phenotypic changes characteristic of infected cells. Tumor viruses may act through a gene or genes in their genome (oncogenes) which, in some way, influence or induce target cell genes. The induced target cell genes, in turn, act to carry out the changes observed in transformed cells. There are at least three major classes of transforming DNA viruses: adenoviruses, which have two groups of oncogenes, E1A and E1B, which act together to produce transformation; papovaviruses, which synthesize proteins, called T antigens, which may work together to transform cells; and herpes viruses, for which no oncogene has been identified as yet.

Although considerable effort has been expended in identifying transforming genes or oncogenes and, in some cases, has also resulted in identification of their protein products, very little is known about the cellular mechanisms affected in the transformation process. There is a consensus that these oncogenes perturb cell growth by modifying the expression or activity of key growth related genes. It would be very helpful to have a better understanding of how transformation occurs, particularly if the biochemical pathways affected can be identified. Such knowledge would make it possible to design compounds which can interfere with or counter the effects of the transforming signals and, thus, are useful in preventing transformation or minimizing the extent to which it occurs, once begun, and, thus, to reduce effects on individuals in whom it occurs.

DISCLOSURE OF THE INVENTION

The present invention relates to a method of inhibiting growth, transformation and/or metastasis of mammalian cells in which activity of at least one purine metabolic enzyme is elevated (i.e. greater than that in the corresponding untransformed or normal cell). As used herein, the term purine metabolic enzyme includes any enzyme which participates in purine metabolism or in regulation of nucleotide levels or the relative ratios of the phosphorylated states (e.g., ATP/ADP), or both. In particular, the present invention relates to a method of inhibiting (preventing, reducing or reversing) transformation of mammalian cells by a DNA tumor virus, a DNA tumor virus factor (or product) or other factor (e.g., a cellular factor) which has an equivalent effect on cells as that of the DNA tumor virus or DNA tumor virus factor (i.e., causes, either directly or indirectly, an increase in purine metabolic enzyme activity). The present invention also relates to a method of inhibiting growth and/or metastasis of mammalian cells in which such a virus, virus factor or other factor has acted. The method is carried out by inhibiting (or interfering with) the increase in purine metabolic enzyme activity caused by the DNA tumor virus or factor, by contacting cells in which the level is increased with a drug capable of causing the desired effect (i.e., inhibition of purine metabolic enzyme activity). This is carried out, for example, by interfering with the ability of the virus or the factor to increase expression of a gene(s) which encodes a host cell purine metabolic enzyme(s) or by counteracting the increase in purine metabolic enzyme activity, directly or indirectly. In carrying out the present method, cells in which the purine metabolic enzyme level is elevated are contacted with the drug (or drugs) under appropriate conditions: that is, conditions appropriate for the drug to pass into the cell (in those embodiments in which an intracellular effect is necessary) or under conditions appropriate for the drug to remain at or within cell membranes (in those embodiments in which an effect at or within the cell membrane is necessary). The present invention further relates to compounds or drugs useful in reducing the effects on cells of a DNA tumor virus, DNA tumor virus oncogenic product, or other factor. It also relates to a method of inhibiting replication of a DNA tumor virus in cells in which purine metabolic enzyme activity is increased and to a method of inhibiting viral activity.

Drugs useful in the present method can have the desired effect on cell transformation, growth or metastasis by acting to combat an effect of the viral product or other factor or to interfere with action of the viral product in one or more of the following ways: by inhibiting the purine metabolic enzyme whose activity in the cell is elevated; by decreasing the message level; by interfering with the transcription factors which induce expression of the host cell purine metabolic enzyme(s); by inhibiting the interaction of the viral product or other factor with a host cell gene(s) encoding a purine metabolic enzyme(s); and by inhibiting interaction of the viral product or factor with a host cell gene product(s) that regulates or that is recruited to regulate the activity or expression of the purine metabolic enzyme(s). As antiviral agents, such drugs act by interfering with the replication of the virus.

Drugs useful in the present method can be existing drugs, analogues of existing drugs or drugs designed specifically for the purpose of reducing purine metabolic enzyme activity, such as by inhibiting the DNA tumor virus or its activity. The present method is particularly useful in blocking the ability of a papillomavirus oncogenic product (e.g., an E7 product) to increase the expression of the host cell creatine kinase gene, or other host cell gene(s) which participates in purine metabolism (e.g., in cervical epithelial cells). Thus, it is useful in inhibiting transformation of such cells.

Other tumors which are characterized by elevated activity of a purine metabolic enzyme(s) (i.e. greater activity than in the corresponding untransformed or normal cell) and which are associated, directly or indirectly, with the presence of the DNA tumor virus, tumor virus factor or other factor can be treated in a similar fashion. For example, tumors that result from cellular mutations that mimic the effects of infection by a DNA tumor virus can be treated in a similar manner. For instance, loss of anti-oncogene products Rb, DCC or p53 may mimic infection by a DNA tumor virus, leading ultimately to elevated activity of a purine metabolic enzyme(s). These tumors are likely candidates for treatment by the present method.

Through use of the present method, it is possible to prevent, reduce or reverse transformation of mammalian cells by DNA tumor viruses, DNA tumor virus factors or other factors that have an equivalent effect on cells and to prevent, reduce or reverse growth and/or metastasis of transformed cells in which such a virus, virus factor, or other factor has acted. Thus, through use of the present method, it is possible to prevent tumor formation, reduce the extent to which tumor formation occurs, or to reverse the progress (e.g. growth or metastasis) of a tumor.

BRIEF DESCRIPTION OF THE DRAWINGS

FIG. 3 shows the sequence relationship between the adenovirus E2E promoter and that of an isozyme (B) of creatine kinase; lines connect identical nucleotides.

FIG. 7 shows part of the sequence of CKB gene, from which antisense oligonucleotides useful to block CKB translation can be determiryed.

FIG. 9 shows the results of an assessment of the effects of concentration on prostate DU145 tumor cell line.

FIG. 10 shows that homocyclocreatine (20–30 irreversibly inhibits DNA synthesis in prostate tumor cell line DU 145.

FIG. 10A is a graph depicting the effect of 0–3 mM of homocyclocreatine on DNA synthesis in prostate tumor cell line DU145 16–46 hours after release from drug.

FIG. 10B is a graph depicting the effects of 0.0, 5.0, 10.0 and 20 mM of homocyclocreatine on DNA synthesis in prostate tumor cell line DU145 1–6 days after release from drug.

DETAILED DESCRIPTION OF THE INVENTION

Figure 1:
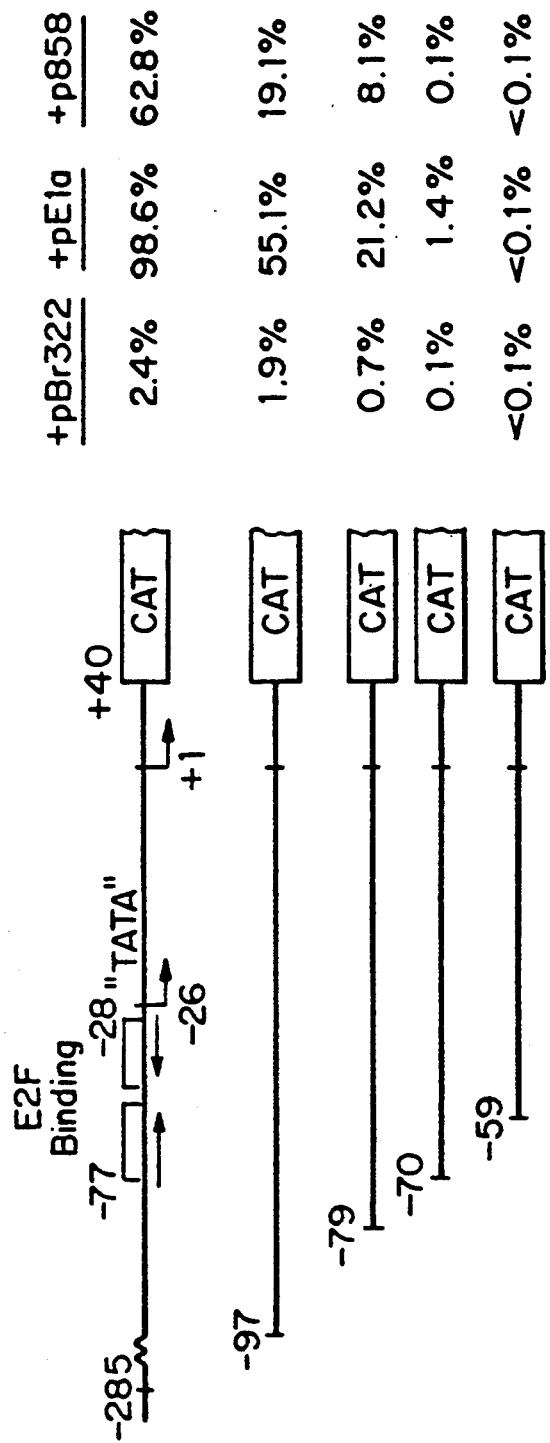
FIG. 1 is a schematic representation depicting the CAT activity of E7 target sequences in the adenovirus E2 promoter hooked to the CAT gene after cotransfection with either pBR322, pE1a or p858 into CV1 monkey cells. This figure shows colocalization of the E7 and E1a target sequences in the E2 promoter attached to the CAT gene.

Oncogenic products of DNA tumor viruses, particularly those DNA tumor viruses associated with transformation or tumors of epithelial cells, have been shown to have certain functional, structural and sequence similarities which make it reasonable to expect that they have a common or similar effect on host cells which results in induction of cellular transformation. In addition, activity of an enzyme which participates in purine metabolism or in regulation of nucleotide levels or the relative ratios of the phosphorylated states (i.e., a purine metabolic enzyme) is known to be elevated (increased) in transformed mammalian cells. In particular, it is known that the activity of brain creatine kinase (CKB), which is a purine metabolic enzyme, is characteristically elevated in transformed cells and tumors in which a DNA tumor virus or DNA tumor virus factor is present or on which such a virus or virus factor has acted, resulting in transformation or tumor formation. CKB is characteristically elevated in many types of tumors and is a reliable marker for at least one tumor type (small cell lung carcinoma). CKB is induced by at least one DNA tumor virus (i.e., adenovirus) and CKB induction correlates with the ability of the oncogenic region of the virus to transform cells.

In particular, it is known that the oncogenic products of two DNA tumor viruses, the E7 protein of human papillomavirus (HPV) 16 and the adenovirus Ela protein, have many similar functions in cells and are able to increase host gene expression. As described in detail herein, these similarities and the ability shown by these DNA viruses to induce cellular transformation appear to be linked to their ability to increase host gene expression, particularly their ability to increase expression of purine metabolic enzymes. In addition, the ability of these viruses to replicate has been shown to be linked to their ability to increase host gene expression of nucleotide metabolic enzymes.

The present invention relates to a method of inhibiting growth, transformation, and/or metastasis of mammalian cells in which activity of one or more purine metabolic enzymes is elevated. This is carried out by inhibiting (reducing or eliminating) the ability of: 1) a DNA tumor virus, 2) a factor produced by or characteristically associated with a DNA tumor virus (a DNA tumor virus factor) or 3) other factor (e.g., a cellular factor) which has an effect corresponding to that of the DNA tumor virus or virus factor to induce cellular transformation or to maintain a transformed phenotype (DNA tumor virus factor equivalent) and to cause an elevation of purine metabolic enzyme activity. This is effected by interfering with the ability of the virus or factor to increase expression of such purine metabolic enzymes or by countering the increase in purine metabolic enzyme activity. Compounds or drugs useful in the present method are also the subject of the present invention.

In particular, through use of the present method, it is possible to inhibit the ability of a DNA tumor virus, a DNA tumor virus factor, or other factor which has an equivalent effect on cells, to increase the expression of host cell enzymes, such as creatine kinase, adenylate kinase, adenylate cyclase and adenosine kinase, which participate in purine metabolism or which interact with these host cell enzymes. It is also possible by the use of inhibitors of these enzymes to counterbalance the induction effect caused by the virus. Thus, it is possible to inhibit the ability of the DNA tumor virus, DNA tumor virus factor, or other factor to induce cellular transformation or to maintain the transformed state. As a result, cellular transformation, maintenance of transformation, growth and/or metastasis is inhibited (i.e., it is prevented or occurs to a lesser extent than would be the case if the present method were not carried out or is reversed, wholly or in part, once a cell has been transformed).

The present method of inhibiting transformation of mammalian cells in which purine metabolic enzyme activity is elevated (i.e., greater than purine metabolic enzyme activity in untransformed cells) can have its effect by several different mechanisms. For example, the ability of a DNA tumor virus, DNA tumor virus factor or other factor to induce transformation can be interfered with by:

1) inhibiting the purine metabolic enzyme(s) whose activity in transformed cells is elevated as a result of the effect of the virus or factor. This can be carried out, for example, by administering a compound or drug which reduces the activity of the purine metabolic enzyme(s) or reduces the association of two or more purine metabolic enzymes;

2) decreasing the message level/preventing translation of the MRNA. This can be carried out by administering antisense constructs which are oligonucleotides selected to bind to a region of the cellular purine metabolic enzyme MRNA necessary for translation. For CKB, for example, this region is defined and is that region at the 3' end, shown in FIG. 7;

3) interfering with transcription factors. This can be carried out by modifying the activity or association of unique factors with their specific promoters. For example, drugs can be designed to interfere with (prevent or modify) the association of transcription factors with genes encoding purine metabolic enzymes, in order to control the extent of initiation and the amount of enzyme produced;

4) by inhibiting interaction of viral products with host cell genes encoding the purine metabolic enzymes. This can be carried out by identifying the target and preventing the association with and/or activation of the promoter. The unique TTAA element on the CKB promoter, which is shared with the adenovirus E2E promoter, might be an excellent candidate; and 5) by inhibiting interaction of viral product(s) with host cell product(s), that regulate or are recruited to regulate the activity or expression of purine metabolic enzymes. This can be carried out by means of compounds designed to bind to the viral products and to inhibit binding of the host cell product with the viral product.

Because it is known that the activity of purine metabolic enzymes, such as creatine kinase, is elevated in mammalian cells transformed by a DNA tumor virus or virus factor, and because there are enzymes which work in conjunction with creatine kinase, such as adenosine kinase, adenylate kinase and adenylate cyclase, such enzymes might be useful as markers for identifying transformed cells. For example, the occurrence (presence/absence) or quantity of one or more of these enzymes can be determined, using known enzyme assays or specific probes from the isolated genes. The occurrence or quantity of one or more of the enzymes can be an indicator or marker useful for detecting transformation or viral infection of cells. The information can be used for diagnostic purposes or for monitoring treatment in an individual in whom diagnosis has been made.

The present method of inhibiting cellular transformation, growth and/or metastasis can be carried out using existing drugs, analogues of such drugs, or drugs specifically designed for the purpose. Drugs can be administered to produce inhibition of cellular transformation by direct interaction with the virus (e.g., by inhibiting production of viral DNA or MRNA expression of the encoded protein); by blocking the domain or sequence of the virus which is responsible for inducing expression of a cellular gene involved in cell growth perturbing functions; by blocking the activity of a factor, produced by or characteristic of the DNA tumor virus, which is the inducer of such a cellular gene; or by acting directly upon host cell products which interact with a viral product to cause transformation. Drugs may act at the enzyme level as well, so that the activity of the purine metabolic enzyme(s), which is elevated in the cell is reduced. Drug analogues and drugs designed for the specific purpose intended are also the subject of the present invention.

The following is a description of DNA tumor viruses able to induce cellular transformation, which can be inhibited by the present method; the basis on which this inhibition is effected; the use of the present method in inhibiting cellular growth and/or transformation and compositions useful in the present method. It is important to note that in each of the instances described, in which cellular transformation occurs, the activity of host cell creatine kinase is increased (is greater than the activity which occurs in the absence of transformation). Therefore, it is reasonable to expect that the present method can be used in the treatment of any tumor in which the activity of creatine kinase is increased significantly above activity in normal cells. Similarly, it is reasonable to expect that the present method can be used in inhibiting transformation of cells in which activity of other purine metabolic enzymes, particularly those which associate functionally with CKB, is increased. it is also possible to inhibit growth and/or metastasis of transformed cells (reduce the extent to which it occurs or prevent its occurrence) using the method and drugs described.

DNA TUMOR VIRUSES

Human Papillomaviruses and Association with Human Anogenital Cancers

Recent investigation has established a strong association between certain human papillomaviruses (HPVs) and some types of human anogenital cancers. More than a dozen different HPV types have been isolated from epithelial tumors of the genital region. Precancerous lesions, such as moderate to severe cervical dysplasia and carcinoma in situ, as well as invasive cervical carcinoma, have been associated with HPV types 16, 18, 31 and 33 (Zur Hausen and Schneider, 1987 In: Howley PM Salzman N Eds. *The Papovaviridae: The Papillomaviruses,* Plenum, N.Y. pp. 24–263) Of the HPVs which have been associated with anogenital malignancies, HPV-16 has been detected most frequently (greater than 60%) in biopsies from cervical carcinoma. RNA analyses for cervical carcinoma tissues and derived cell lines have revealed that the E6 and E7 ORFs are generally expressed, suggesting that their gene products may be necessary for the maintenance of the malignant phenotype. (Schneider-Gadicke and Schwarz, *EMBO-J.*, 5:2285–2292 (1986); Smotkin and Wettstein *PNAS*, 83:4680–4684 (1986); Baker, C. C. et al., *J. Virol.* 61:962–971 (1987); Takebe, N. et al., *Biochem. Biophys. Res. Commun.*, 143:837–844 (1987)). Morphological transformation of established rodent cells has been described for HPV-16 (Yasumoto, B. et al., *J. Virol*, 57:572–577 (1986); Tsunokawa, Y. et al., *PNAS*, 83:220–2203 (1986); Kanda, T. et al., *Jpn. J. Cancer Res.*, 78:103–108 (1987)). This transforming activity has been localized to the E6/E7 region (Bedell, M. A. et al., *J. Virol*, 61:3635–3640 (1987); Kanda et al., ibid, 62:610–613 (1987)). In addition, the HPV-16 E6/E7 region has been shown to encode a function capable of cooperating with an activated ras oncogene in the transformation of rat embryo fibroblasts. (Matlashewski, C. et al., *EMBO J.*, 6:1741–1746 (1987)).

The immortalization function of HPV 16 has been mapped to the E7 ORF by Phelps and co-workers. (Phelps, W. C. et al., *Current Topics in Microbiological and Immunology*, 144:153–166, Springer-Verlag, Berlin Heidelberg, (1989). These researchers also found the E7 product of HPV-16 to have activities similar to those of the oncogenic product of another virus, the E1a protein of adenovirus.

Adenoviruses

Adenoviruses are a class of viruses which cause upper respiratory infections in many animals. They have been isolated from a wide range of species, and at least 31 different serotypes of human adenoviruses have been characterized. Luria et al., *General Virology*, pp. 360, 3rd Ed., Wiley & Sons, New York (1978). The basic molecular biology of these viruses is very similar. The early adenovirus gene products are oncogenes that have been shown to be able to immortalize primary cells in culture. In collaboration with a second oncogene, such as the H-ras gene, they can transform cells in vitro.

The proteins encoded by the E1a region of the adenovirus genome are necessary for efficient viral replication and for viral transformation of cells in culture. The E1a proteins contain three distinct domains that are strongly conserved among adenovirus subgroups and species. H. van Ormond et al., *Gene*, 12:63 (1980); D. Kimelman et al., *J. Virol.*, 53:99 (1985). The vast majority of domain 3 is unique to the 289 amino acid protein and is important for trans-activation of early viral promoters. A. J. Berk, *Ann. Rev. Genet.*, 20:45 (1986). Domains 1 and 2 are required for transcriptional repression, transformation, and induction of DNA synthesis, but not for activation of transcription. J. W. Lillie et al., *Cell*, 46:1043 (1986); J. W. Lillie et al., *Cell*, 50:1091 (1987).

Similarities Between Human Papillomavirus E7 Onco-genic Product and Adenovirus E1a Oncogenic Product In summary, the papillomavirus oncogenic product and the adenovirus oncogenic product described above have been shown to have the following similarities:

1. Phelps et al. have shown that E7 has transcriptional transactivation properties analogous to those of adenovirus E1a. That is, E7 can affect heterologous promoters, including the adenovirus E2 promoter (Phelps, W. C. et al., Current Topics in Microbiology and Immunology: Transforming Proteins of DNA Tumor Viruses, Knappers, R. and Levine, A. J., Eds., Springer-Verlag, pp. 153–166 (1989)). The adenovirus E2 promoter sequences required for E1a stimulation and HPV-16 E7 activation have been shown to be coincident.

FIG. 1 is taken from Phelps et al. (Phelps, W. C. et al., Current Topics in Microbiology and Immunology: Transforming Proteins of DNA Tumor Viruses, Knappers, R. and Levine, A. J., Eds., Springer-Verlag, pp. 153–166 (1989)). The figure is a schematic representation of the E7 target sequence in the adenovirus E2 promoter hooked to the CAT gene. Bal31 deletions with end points at −97, −79, −70 and −59 derived from the −285 to +40 AdE2CAT plasmid were generated. Five micrograms of each Ad E2CAT plasmid together with 5 µg of either PBR322, PELA (a plasmid encoding adenovirus E1a product) or p858 (a construct expressing the papillomavirus E7 product) were co-transfected into CVI monkey cells and assayed for CAT activity. The locations of the E2F binding sites and its major and minor RNA initiation sites are shown. 2. Comparison of the amino acid sequences of HPV-16 E7 and adenovirus E1a proteins reveals regions of significant amino acid similarity which are well conserved within the E7 proteins of other papillomaviruses present in genital tissues.

Figure 2:
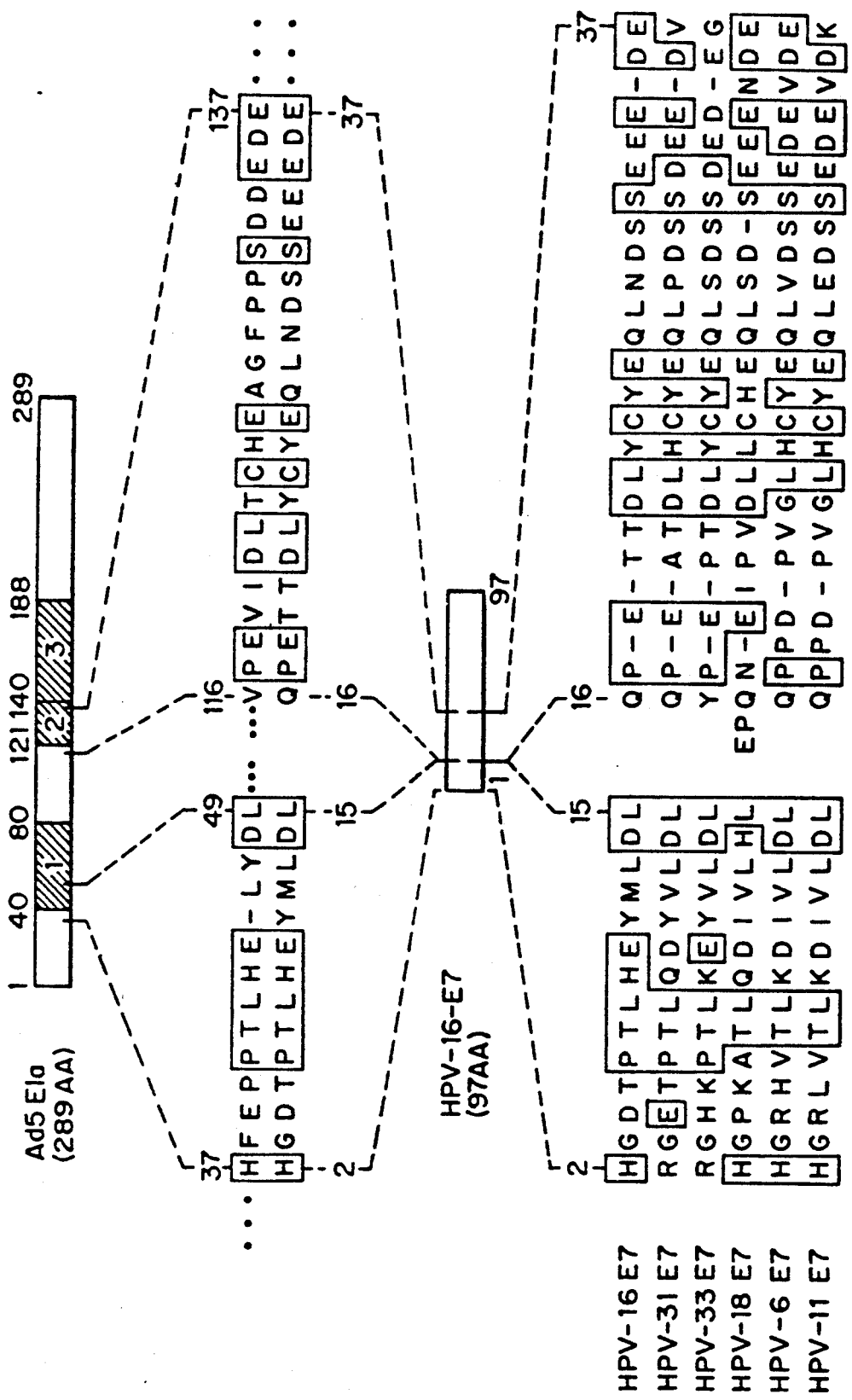
FIG. 2 shows the structural similarity between adenovirus E1a and papillomavirus HPV-16 E7 transforming proteins.

FIG. 2, taken from Phelps, et al., (ibid), shows structural similarity between Adenovirus E1a and HPV-16 E7. A schematic diagram of the Ad5 E1a region is shown at the top of the figure with the conserved amino acid domains 1–3. Homologous (boxed) and functional (hatched) amino acids of domains 1 and 2 from E1a which are found in HPV-16 E7 are located within the N-terminal 37 residues. The predicted amino acid sequences for this region of the E7 proteins of the other genital-associated HPVs are shown.

3. The conserved sequences between E1a and E7 mentioned above are restricted to domains 1 and 2 of E1a. Those sequences are important for the ability of E1a to transform and induce DNA synthesis. (Lillie, J. W. et al., (1986) *Cell*, 46:1043–1051).

4. Both E1a and E7 associate with the anti-oncogene product of the retinoblastoma (Rb) gene (N. Dyson et al., *Science*, 243:934–937 (1989)). The conserved sequences between the two proteins which are important for transformation are also important for the association with the Rb protein. This suggests that the two proteins interact with the same cellular metabolic events to cause transformation.

5. E7 can complement the ras oncogene in transforming baby rat kidney cells in a similar fashion to E1a complementation (Phelps et al., ibid).

Thus, two DNA tumor viruses, each belonging to a different class of DNA viruses, have been shown to have structural and sequence similarities and to modulate host gene expression. Both E7 and E1a appear to possess multiple functions and it is reasonable to assume that their ability to modulate host gene expression is an important event in their ability to induce cellular transformation. If the cellular gene products which are targets for such oncogenic regulators which require the transforming domains of these DNA tumor viruses were identified, it would not only provide great insight into metabolic events which are affected during transformations, but also provide a means by which transformation by such DNA tumor viruses can be inhibited. In addition, it would make it possible to design markers useful in diagnosing infection with the responsible DNA virus and in monitoring subsequent transformation. It would also make it possible to design compounds or drugs useful for inhibiting activated targets or activation events, which could serve as chemotherapeutic and antiviral drugs. As described in the following sections, it has been determined that at least one cellular enzyme which is involved in energy metabolism and purine pathways (i.e., creatine kinase) and which is a tumor marker is a reasonable target of DNA tumor viruses. The oncogene proteins of the DNA tumor viruses act on host/cellular genes and modify expression of some selected genes, resulting in induction of a transformed state.

IDENTIFICATION OF CELLULAR GENE PRODUCTS WHICH ARE TARGETS FOR ONCOGENIC REGULATORS

It is reasonable to expect that a cellular gene product, creatine kinase, which is an enzyme involved in maintenance of ATP at sites of cellular work or energy production, is a target of oncogenic products of DNA tumor viruses, such as the HPV E7 product and the adenovirus E1a product, which act as regulators and modify or regulate expression of cellular genes. In addition to discrete DNA tumor viruses, there appear to be factors which are consistently present in or secreted from some transformed cells or tumor cells, which in and of themselves are capable of inducing DNA synthesis in host cells and probably are able to modulate cellular gene expression with much the same effect that a DNA tumor virus has (i.e., increase in expression of the cellular gene). Such factors are referred to herein as DNA tumor virus factors.

Creatine kinase has been shown to be elevated in a variety of tumors and has been described as a tumor-associated marker. High levels of creatine kinase are found in breast and prostate carcinomas, especially in the presence of overt metastasis (Silverman, L. M. et al., *Clin. Chem.*, 25:1432–1435 (1979); Homberger, et al., *Clin. Chem.* 26: 1821–1824 (1980); Thompson et al., *Lancet* 98: 673–675 (1980)). In breast cancer, the tumor burden correlates well with the degree of elevation of brain creatine kinase. In cancers of the bladder, prostate, testis, head and neck, raised serum creatine kinase B levels occurred more frequently in patients with metastatic disease than in those thought to have local disease alone, while in sarcoma, cancer of the ovary, uterus, cervix, stomach, bowel and anal canal, the presence of persistent disease correlated with high serum CKB levels (Rubery, E. D. et al., *Eur. J. Cancer Clin. Oncol.*, 18:951–956 (1982)). In neuroblastomas, the extent of the disease was associated with an increased incidence of elevated serum creatine kinse B. The highest pre-treatment blood levels were found in stage IV disease, and a strong correlation between the pretreatment CKB level and the outcome of the disease in patients with neuroblastomas was observed (Ishiguro, Y. et al., *Cancer* 65:2014–2019 (1990)).

It is clear that CKB is an enzyme that is very active in many tumors, particularly those of epithelial origin (e.g., small cell carcinoma, neuroblastomas retinoblastomas, cervical carcinomas, bladder cancer, and ovarian cancer). Some of these malignancies may be triggered by a DNA tumor virus or DNA tumor virus factor. Alternatively, transformation could result from the action of other factors (e.g., cellular factor, growth factor), which have an effect on cells equivalent to that of DNA tumor virus or virus factor. For example, activated oncogenes, mutated tumor suppressors or antioncogenes, or autocrine growth factors may also act to increase purine metabolic enzyme activity. The present method of inhibiting growth, transformation, and/or metastasis of mammalian cells, is applicable to cells transformed by diverse mechanisms in which the activity of at least one purine metabolic enzyme is elevated.

As discussed below, creatine kinase has several characteristics which support the idea that it is such a target of oncogenic products of DNA tumor viruses. As is also discussed below, other enzymes which have a similar role in cellular metabolism (i.e., purine metabolic enzymes) and which work in association with CKB are likely to be targets of oncogenic products as well. Thus, interference with the ability of an oncogenic product of a DNA tumor virus, DNA tumor virus factor, or other factor which has an equivalent effect on cells to regulate expression of enzymes which participate in purine metabolism and/or interference with another enzyme(s) which interacts with the purine metabolic pathway enzyme(s) will result in inhibition of or interference with the ability of such viruses or factors to transform cells. This should be particularly useful in inhibiting tumor formation, growth or metastasis in epithelial cells and, particularly, in epithelial cells of the cervix, in which HPV is known to be present. The method of the present invention makes it possible to inhibit the ability of DNA tumor viruses to act as mediators of cell transformation, and thus, to inhibit cell transformation or tumor formation or spread, by acting upon production of viral DNA, RNA or encoded oncogenic products, as well as by interfering with other viral or cellular products which normally interact or cooperate with viral or cellular products to bring about cell transformation.

As described in co-pending applications U.S. Ser. No. 07/310,773, entitled Regulation of Expression of a Gene for Energy Metabolism by Domain II of the Adenovirus E1A Gene, U.S. Ser. No. 07/344,963, entitled Alteration of Oncogenic or Viral Activation of Cellular Genes Involved in Adenosine Metabolic Pathways, and U.S. Ser. No. 07/467,147, entitled Method of Inhibiting Transformation of Cells in Which Purine Metabolic Enzyme Activity is Elevated, the teachings of which are expressly incorporated herein by reference, the gene encoding human brain creatine kinase (CKB) has been isolated and sequenced and its promoter has been shown to have a strong sequence relationship with the promoter region of the adenovirus E2E gene (FIG. 3). The first 95 bases of the E2 and CKB promoters are shown. Solid lines connect identical bases. This is the first example of a strong sequence similarity between a cellular gene promoter region and a viral gene promoter. As also described in these co-pending applications, it has been shown that brain creatine kinase expression is regulated by the oncogenic products of the E1a region of the adenovirus. Thus, it has been shown that a cellular gene which is associated with energy metabolism and regulation of intracellular nucleotide levels is turned on, or activated, by the transforming region of an oncogene encoded by a DNA tumor virus. Induction of a cellular gene by oncogenic products has, thus, been shown for the first time to require both of the transforming domains of the oncogenic protein of the virus.

The CKB gene encodes an enzyme involved in the maintenance of ATP at sites of cellular work. (Bessman, S. P., *Ann. Rev. of Biochem.*, 54:831–862 (1985)). The enzyme is highly elevated in many tumors and is used as a diagnostic marker for small cell lung carcinoma (Gazdar, A. F. et al., *Cancer Res.*, 41:2773–2777 (1981)). As also described in the co-pending applications, preliminary characterization of the regulatory region of the isolated CKB gene revealed an unexpectedly striking resemblance to that of the adenovirus E2E gene. FIG. 3 shows the promoter sequences of CKB and E2E. Solid lines connect the same bases on the two promoters. The E2E gene of adenovirus encodes a 72 Kd single stranded DNA binding protein which is involved in virus replication (Friefeld, B. R. et al., *Virology*, 124:380-389 (1983)).

Figure 4:
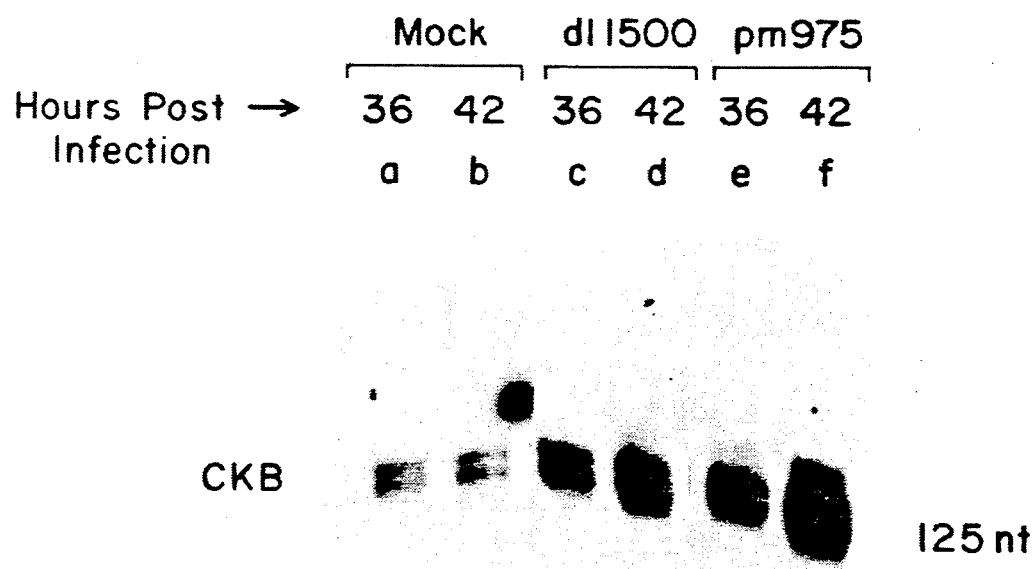
FIG. 4 is a Northern blot detecting CKB RNA from HeLa cells either mock infected (lanes a and b), infected with the 12S expressing virus dl 1500 (lanes c and d) or infected with the 13S expressing virus pm975 (lanes e and f). This fiture shows that the 12S product of E1a (which encodes the transforming protein) lacking the transactivation function activates expression of CKB.
Figure 5A:
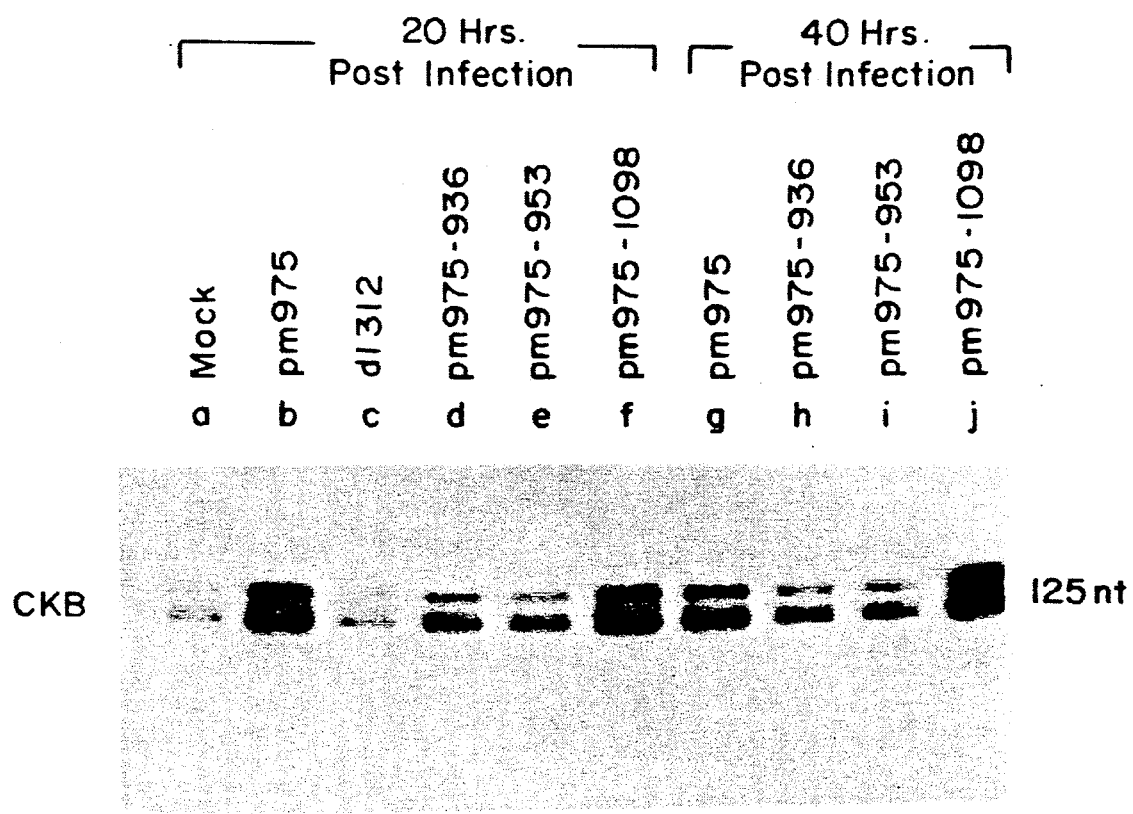
FIG. 5A is a Northern blot detecting CKB RNA from HeLa cells either mock infected (lane a) or infected with mutant viruses (lanes b-j). This figure shows that point mutations in domain 2 which disrupt transformation are impaired for E1a-induced expression of CKB.
Figure 5B:
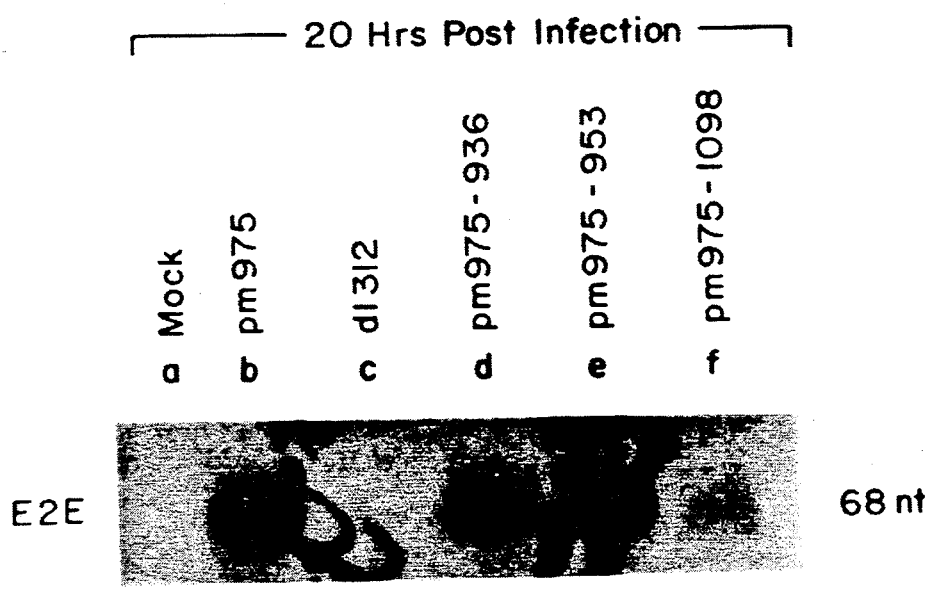
FIG. 5B is a Northern blot detecting adenovirus E2 RNA from the same HeLa cells as in FIG. 5A.
Figure 6A:
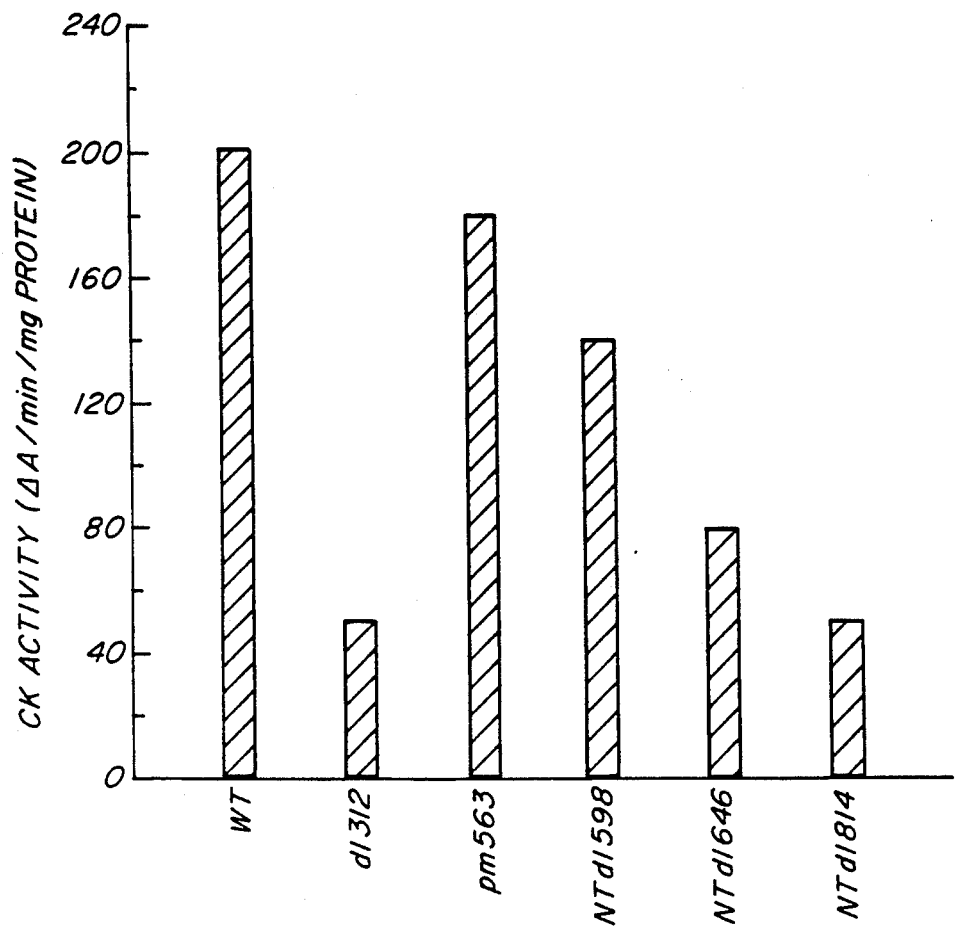
FIG. 6A is a bar graph depicting creatine kinase activity in HeLa cells infected with amino deleted viral constructs. This graph shows that amino terminal deletions of E1a which disrupt transformation also result in an inability to induce expression of CKB.
Figure 6B:
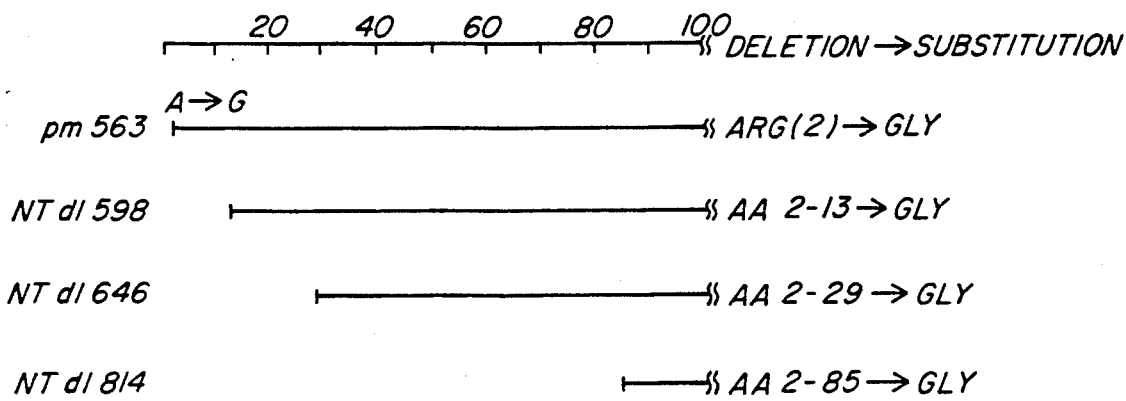

The expression of this gene is highly dependent on the adenovirus oncogenic products of the E1a region (Berk, A. J., *Ann. Rev. Genet.*, 20:45-79 (1986)). The unexpected relationship of the two promoters prompted an investigation of a possible functional relationship between the two. Infecting a variety of human cell lines (e.g., cervical cells, monocytic cells and small cell carcinoma) in tissue culture facilities has demonstrated that CKB expression is activated in every cell line tested that has already a detectable CKB level. The E1a proteins of the oncogenic region are important for the induction, as is shown by the fact that infection with a deletion virus mutant dl312, which does not include the E1a region, is defective for induction. What was striking was that domains one and two of the E1a molecule, which are associated with transformation and induction of DNA synthesis in host cells, are the same domains required for induction of CKB activity, as illustrated in FIGS. 4, 5 and 6. FIG. 4 shows that infecting HeLa cells with a mutant virus that expresses only the 12S product (associated with transformation) results in induction of CKB expression to an extent comparable to that seen when HeLa cells are infected with the 13S product, which encodes the entire protein with all three domains. Lanes a and b, mock infected plates probed with CKB probes; lanes c and d, RNA harvested from a dl 1500-infected plates (12 S product producer) and probed with CKB probes, lanes e and f, results of probing RNA harvested from cells infected with pm975 virus (expressing 13S product).

FIG. 5 shows that point mutations in transforming domain 2 are impaired for E1a-induced expression of CKB. HeLa cells were infected with different mutant viruses. In FIG. 5, the lanes are as follows: lane a, mock infection; lanes b, g, wild-type pm975 virus (13.5' product); lane c mutant dl 312 (an E1a deletion mutant); lanes d, e, h, i mutant viruses pm 975-936 and 953, each of which has a point mutation in domain 2 and disrupts the ability of E1a to transform. Lanes f, j mutant virus pm 975-1098, which has a point mutation in domain 3 and does not affect transformation functions. Panel B shows results of probing the same RNA with adenovirus E2 probes.

FIG. 6 shows that amino terminal deletions of E1a obliterate the induced expression of CKB. HeLa cells were infected with amino terminal deleted viral constructs. Panel a shows creatine kinase activity, represented by bars. Panel b shows amino acids deleted in each mutant (right) and names given by Whyte and co-workers. Whyte, P. et al., *J. Virol.*, 62:257-265 (1988). The same observation is seen when RNA harvested from cells is probed with CKB specific primers (data not shown). Hence, the induction of CKB, which is a major enzyme in energy metabolism, regulation of nucleotide levels and purine pathways associates well with the ability of E1a to transform. This leads to the conclusion that CKB induction must be part of the mechanism by which cells are transformed by at least one DNA tumor virus (adenovirus type 5).

In addition, as described above, the papillomaviruses (e.g., type 16) which are associated with malignancies in the cervix encode a protein (the E7-encoded protein) which is very similar in sequence and function to that of the E1a-encoded protein in the transforming region. In particular, several key similarities have been identified: 1) the E7-encoded protein has amino acid sequence homology to the E1a-encoded protein in the important transformation domain; 2) the E7-encoded protein, like the E1a-encoded protein can act to turn on the adenovirus E2 promoter; 3) both proteins interact with similar host proteins, such as the retinoblastoma gene product; and 4) the E7-encoded protein can replace the E1a-encoded protein in transformation assays in which complementation with ras is tested.

It is also important to note that the sequence of the adenovirus E2 promoter, which controls the replication of adenovirus, is very similar to that of the cellular CKB promoter. Either E1a of adenovirus or E7 of papillomavirus virus can induce the E2 promoter and they both require the first 90 bases of the promoter for induction. EIA turns on CKB expression and because the first 90 bp of the CKB promoter sequence are very similar to those of the E2 promoter, it is reasonable to expect that E7 acts similarly (i.e., turns on CKB expression). In addition, the fact that the transformation domains 1 and 2 of E1a are required for CKB induction by the adenovirus and the fact that the same sequences of the two domains are conserved in the E7 protein of papillomavirus strongly suggest that GKB will be induced by E7 and would require the transformation domains of E7. Mutations which disrupt the ability of E1a to transform are dysfunctional for CKB expression. These crucial amino acids are conserved in the transforming part of E7. It is likely that these two DNA tumor viruses cause some similar modifications in the host cell metabolism and hence work at least partially via common mechanisms to cause transformation. It has been shown that CKB associates with the ability of E1a to transform cells. It is reasonable, based on experimental proof and the literature, to predict that creatine kinase or the metabolic pathway is similarly affected in epithelial cells of the cervix which are infected by papillomaviruses associated with malignancies. After infection of the cervix by such a virus and expression by the virus of the encoded transforming proteins, increased expression of CKB and the enzymes working in conjunction with it (e.g., adenylate kinase and cyclase) occurs. Detection of some or all of these enzymes can serve as the basis for determining whether the virus is present and, if necessary, the extent to which it occurs.

Inhibition of Growth Factors Induced in Transformed or Virally Infected Epithelial Cells For non-transformed mammalian cells to grow in vitro, they require the presence of appropriate polypeptide growth factor(s) that exert their effects through specific plasma membrane receptors. Primary epithelial cells are hard to grow in culture. This has hindered the study of epithelial cell transformation in vitro, and explains why most in vitro transformation experiments have been done with fibroblasts, although malignant tumors of non-epithelial cell origin account for only 10-20% of human neoplasms. However, human and rodent primary epithelial cells can be transformed with adenovirus, a DNA tumor virus (Houweling, A. P. et al., *Virology* 105:537-550 (1980); Vander Elsen, P. J. et al., *Virology* 131:242-246 (1983); Whittaker, J. L. et al., *Mol. Cell. Biol.* 4:110-116 (1984)).

Adenoviruses normally infect quiescent epithelial cells and the expression of the adenovirus type 5, E1a 12S gene product enables primary rodent epithelial cells to proliferate in the presence or absence of serum (Quinlan, M. P. and T. Grodzicker, *J. Virol.* 61:673-682 (1987)). Thus, the 12S gene product provides a means of studying the changes involved in the immortalization and transformation of primary epithelial cells. The 12S gene is a member of the adenovirus E1a transcription unit. At early times, after infection, and in transformed cells, two E1a transcripts designated 13S', 12S' mRNAs are produced. These mRNAs are translated into proteins of 289 and 243 amino acids, respectively, that differ only by the presence of an additional internal 46 amino acids in the 289 amino acid protein.

The products of the E1a region can immortalize primary cells (Moran, E. et al., *J. Virol.* 57:765-775 (1986)) and can cooperate with other viral genes and cellular oncogenes to transform primary rat cells (Ruley, H. E., *Nature* 304:602-606 (1983)). The E1a 12S protein seems to play a major role in the stimulation of cell proliferation responses. The 12S gene product is required for optimal virus production in growth arrested permissive cells, but not in actively growing cells (Spindler, K. R. et al., *J. Virol.* 53:742-750 (1985)).

It induces cellular DNA synthesis and cell cycle progression in quiescent cells (Quinlan, M. P. and T. Grodzicker, *J. Virol.* 61:673-682 (1987); Spindler, K. R. et al., ibid); Stabel, S. P. et al., *EMBO J.* 4:2329-2336 (1985)). It can immortalize primary epithelial cells so that they retain many of their differential characteristics. The 12S product has been shown to cause/trigger the production of a growth factor, when introduced into primary kidney quiescent cells. Such a DNA tumor virus factor is a substance produced by or associated with a DNA tumor virus in a transformed or tumor cell and is capable of inducing immortalization in the absence of the DNA tumor virus itself. For example, recently Quinlan et al. (Quinlan, M. P. et al., *PNAS* 84:3283-3287 (1987)), found that infection of primary baby rat kidney cells with an adenovirus variant that encodes only the 12S product results in production of a growth factor that stimulates primary epithelial cells to proliferate. Media from cells that were infected with this variant virus, was filtered (to remove intact virus) and fed to cells which never saw the virus. Results showed that this conditioned media was able to induce epithelial cell DNA synthesis and proliferation between 24 and 36 hours after addition. A growth factor seems to be secreted from the epithelial cells upon infection with the 12S virus. The factor can act in an autocrine fashion and has a large molecular weight. The growth factor appears to be a unique mitogen for epithelial cells. Although it has been shown that the 12S product of adenovirus can induce DNA synthesis, proliferation, immortalization or transformation of its host cell, it is unclear how induction occurs. Other DNA tumor viruses associated with malignancies show sequence similarity to the 12S protein of adenovirus and most probably secrete similar factors.

It appears that the growth factor released by 12S adenovirus infection might be mediating the observed effects of the 12S product (immortalization, induction of DNA synthesis). As described previously, the 12S product is capable of inducing the expression of CKB. The regions required to induce CKB expression or the production of the viral factor are similar. This suggests that the virus might be affecting the host cell genes via the secreted factor. Hence, the factor which is the hormone might be the real inducer of CKB and other enzymes. Adjacent epithelial cells contacted by these factors may be stimulated to elevate purine metabolic enzyme activity, while undergoing DNA synthesis and proliferation. These cells may become transformed ultimately, or may secrete factors, enzymes or metabolites that are used by the original transformed cell. This model is further favored by the fact that the kinetics of induction of CKB and the factor are similar. It is reasonable to expect that this factor (or derivatives thereof) is secreted by many tumors in which CKB (and adenosine metabolic enzymes) is highly activated. Further support for this idea is the fact that many DNA tumor viruses, such as polyoma and papilloma virus encode transforming products with amino acid sequences similar to the amino acid sequence of the adenovirus 12S products. Thus, cells infected with such viruses are very likely going to express this DNA tumor virus factor or transforming factor and cause induction of purine metabolic pathway enzymes in much the same manner as the 12S factor causes induction.

The CKB gene is known to be very responsive to multihormonal signals, implying it is indeed active in signalling or is along a metabolic path that mediates these effects. Thus, this adenovirus factor might be a new hormone which also regulates CKB. Most of these hormones, in spite of being different and having different receptors, might pass by or affect a common event which CKB is part of.

A seemingly unrelated virus, the cytomegalovirus, which induces CKB expression (Colberg-Poley, A. M. et al., *Virology*, 166(1):217-228 (1988)), also appears to induce production of a factor capable of stimulating DNA synthesis and modifying cell growth (Gonczol, E. and S. A. Plotkin, *J. Gen. Virol.*, 65:1833-1834 (1984). This factor appears to function, at least partially, by modifying microtubule structure. Creatine kinase is thought to associate with the microtubule structure (Eckert, B. S. et al., *J. Cell. Biol.* 86:1-5 (1980)). This factor might be the inducer of CKB expression.

Interruption of the autocrine loop which links this growth factor and its induction of enzymes, using selected drugs (e.g., competitive factor antagonists) can be carried out, using competitive antagonists which interfere with effects of the factor. Drugs may also interfere with the ability of the factor to act on cells, blocking autocrine stimulation or stimulation of adjacent cells. In addition, antibodies against the factor or receptor it interacts with can be used to block the factor's effect. Such compounds can be used for the treatment of virally infected cells and tumors of epithelial origin.

USES OF THE PRESENT METHOD

Because of the increased levels of CKB and other cooperative enzymes, simple enzyme assays can be used to detect a DNA tumor virus in cells in which one is thought to be present. Such assays can also be used for diagnostic purposes or for monitoring treatment provided to an individual in which the presence of transformed cells has been detected. Enzyme assays may also be used together with other methods of diagnosis. For example, the sensitivity of cytologic examination (Papanicolaou smear test) carried out in conjunction with detection of human papillomavirus (HPV) may be superior to the use of either cytologic studies or HPV detection alone in evaluating patients with cervical lesions (Ritter, D. B. et al., *Am. J. Obst. Gynecol.*, 159(6): 1517–1525 (1988)). However, presently-available methods for detection of HPV, such as Southern blots which use labelled probes from the virus, are often technically difficult, time consuming, or costly. In contrast, enzyme assays are practical, rapid (e.g., in this case, approximately 25 minutes), inexpensive and easy to carry out in clinical settings. The detection of infection with HPV, through the method of the present invention, can be substituted for Southern blotting or other technically difficult, time consuming or costly methods, as a routine assay to complement the Papanicolaou smear test.

For example, a diagnostic assay can be carried out as follows: proteins can be extracted from cervical scrapings, such as those obtained for cytologic evaluation and extracted (e.g., by freeze-thawing). The supernatant can be assayed for enzymes of interest (e.g., creatine kinase, adenylate kinase). Two or more enzymes can be assessed simultaneously. Such enzyme assays can measure, for example, CKB activity, as well as activity of one or two additional enzymes along the purine metabolic pathway.

A drug or compound suitable for use in the method of the present invention is one which: 1) is able to affect cells in which a DNA tumor virus, DNA tumor virus factor, or other factor which has an equivalent effect on cells has acted to cause, directly or indirectly, an elevation of the activity of a purine metabolic enzyme(s) and 2) is able to prevent the transforming domain of the oncogenic virus, tumor virus factor or other factor which has an equivalent effect on cells from inducing the purine metabolic activity or is able to inhibit the activity of the purine metabolic enzyme, directly or indirectly. The drugs can act outside of the cell, (e.g., by blocking the effect of a secreted factor or enzyme, by influencing uptake of creatine), or can enter the cell to act within the cell in one or more of the above-described ways. A drug having these characteristics can be a protein, peptide, a nucleic acid sequence, or an agent which acts, directly or indirectly, to reduce the velocity of a purine metabolic enzyme. For example, inhibitors, substrate analogs, or slow substrates of a purine metabolic enzyme will, when present with the natural substrate(s), reduce the velocity of the enzymatic reaction catalyzed by a purine metabolic enzyme on the natural substrate(s). Note that preventing induction of a purine metabolic enzyme(s) in a cell in which its activity is elevated will also reduce the velocity of reaction. Drugs useful in the present method can be selected or designed to act in one or more of the above-described ways.

The drug(s) is administered to an individual in whom a DNA tumor virus or virus factor has acted, resulting in a cellular abnormality or a tumor. The drug is administered in sufficient quantity to reduce or eliminate the effect of the DNA tumor virus, virus factor, or other factor on cells.

For example, a drug which is an antisense construct (oligonucleotide sequence) which binds selectively to a region of the RNA necessary for translation can be used. In the case of CKB, the oligonucleotide sequence is one which binds selectively to a region of CKB RNA, as represented in FIG. 7, which is needed for translation. The effects of the transforming viral DNA are, as a result, reduced or prevented. That is, an oligonucleotide sequence capable of entering the cell nucleus and binding (hybridizing) to the specific activated message to block it can be introduced into cells. Hybridization to the nucleotide sequence renders it unavailable for further activity. In another approach, a drug which interferes with a transcription factor (e.g., by acting upon a promoter or blocking the ability of a transcription factor(s) to activate a promoter(s)) is administered in sufficient quantities to have the desired effect. Alternatively, a drug which inhibits interaction of the viral oncogenic product(s) (e.g., the E7 product, E1a product) with a cellular gene encoding a purine metabolic enzyme can be administered. Inactivation can occur, for example, by binding of the drug to the viral oncogenic product or by destruction of the viral oncogenic product by the drug.

Drugs which act to inhibit the activity of a purine metabolic enzyme(s) which is elevated in transformed cells may act directly or indirectly. Inhibition will result in a decrease in the activity of the purine metabolic enzyme(s), and of the velocity of the reaction in particular. For example, the drugs may act by interfering with the ability of purine metabolic enzymes to associate or interact with one another, or by altering the activity of an enzyme in the pathway resulting in decreased velocity of the purine metabolic enzyme whose activity is elevated.

The particular target is determined by the activity elevated in the cell. For example, the cellular gene encoding the purine metabolic enzyme adenosine deaminase has been shown to have a striking resemblance (sequence similarity) at the promoter level to brain creatine kinase. Preliminary data shows that the adenosine deaminase promoter, like the promoter of brain creatine kinase, is induced by the E1a products. This is of particular interest because adenosine deaminase is also a tumor antigen/thymus leukemia antigen, is involved in adenosine metabolism, and is vital for DNA synthesis. By use of the present invention, transformation, growth and/or metastasis of cells in which the activity of adenosine deaminase is elevated could be inhibited.

Adenylate kinase is another purine metabolic enzyme which can be inhibited by the present method and whose inhibition may result in inhibition of cellular transformation. Adenylate kinases (NTP: AMP phosphotransferases, N, adenine or guanine) are relatively small (21-27 kD), monomeric enzymes which catalyze the interconversion of nucleotides according to the equation: $Mg^{++}NTP+AMP \rightleftharpoons Mg^{++}NDP+ADP$. The enzyme is ubiquitous, is abundant in tissues where the turnover of energy from adenine nucleotides is high (Noda, L., *In: Enzymes*, (Boyer, P., ed.) Vol. 8, pp. 279–305, Academic Press, Orlando, Fla.), and has an important role in maintaining energy charge of the adenylate pool (Lipman, F., *Curr. Top Cell. Regul.*, 18:301-311 (1981); Atkinson, D. E., *Biochemistry*, 7:4030–4034 (1968)). The prokaryotic gene from *E. coli* has been cloned (Brune, M. et al., *Nucleic Acids Res.*, 13:7139-7151 (1985). This and previous studies (Glaser, M. et al., *J. Bacteriol.*, 123:128-136 (1975) have shown that adenylate kinase is a key enzyme in controlling the rate of cell growth. By the method of the present invention, the activity of adenylate kinase in tumor cells in which adenylate kinase is elevated may be inhibited. Furthermore, by virtue of its association with creatine kinase and/or because it can provide dinucleotide substrates for creatine kinase, inhibiting the activity of adenylate kinase is expected to decrease the velocity of creatine kinase.

The isozymes of creatine kinase catalyze the resynthesis of ATP for use by cellular ATPases, processes of contraction, macromolecular synthesis, and maintenance of ion gradients, for example (Bessman, S. P. and C. L. Carpenter, *Ann. Rev. Biochem.*, 54:831-62, 1985). Creatine, creatine phosphate and creatine kinase have been proposed to facilitate energy distribution in several tissues, such as muscle, heart and brain by means of the creatine phosphate shuttle.

Creatine is synthesized from the amino acids arginine, glycine and methionine in organs such as liver, pancreas, and kidney, and is transported via the blood for uptake and utilization by muscle and nerve tissues (Griffiths, G. R. and J. B. Walker, *J. Biol. Chem.*, 251:2049-2054 (1976)). The biosynthesis of creatine occurs in two steps as indicated below and is catalyzed by arginine:glycine amidinotransferase and guanidinoacetate N-methyltransferase, respectively.

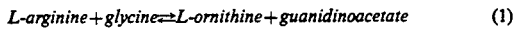

$$L\text{-}arginine + glycine \rightleftharpoons L\text{-}ornithine + guanidinoacetate \quad (1)$$

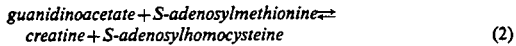

$$guanidinoacetate + S\text{-}adenosylmethionine \rightleftharpoons \\ creatine + S\text{-}adenosylhomocysteine \quad (2)$$

Due to the role of creatine and creatine phosphate in the cell as a reserve of high-energy phosphate for the rapid regeneration of ATP, creatine synthesis is intimately involved with regulating nucleotide availability. Walker and Hannan have reported that the availability of arginine and glycine is rate limiting for creatine biosynthesis during a major period of development of the chick embryo, and that analogs of creatine such as cyclocreatine and guanidinoacetate can suppress amidinotransferase levels in liver of chicks (*Biochemistry*, 15: 2519-2522, (1976)). Later studies showed that regulation was at the message level. Reducing the activity of creatine biosynthetic enzymes could affect the velocity of the reaction of creatine kinase by limiting substrates. Thus, creatine analogs and other drugs which act to interfere with the activity of creatine biosynthetic enzymes are useful in the present method.

There are many possible sites for the action of drugs that inhibit brain creatine kinase and/or other enzymes which participate in purine metabolism. Thus the effects of such drugs can be direct or indirect, operating by mechanisms including, but not limited to influencing the uptake or biosynthesis of creatine, the function of the creatine phosphate shuttle, inhibiting the enzyme activity, or the activity of associated enzymes, or altering the levels of substrates or products of a reaction, to alter the velocity of the reaction.

In the method of the present invention, at least one drug which is capable of inhibiting the induction or activity of a purine metabolic enzyme (e.g., adenylate kinase or creatine kinase) or another enzyme which participates in the purine metabolic pathway, or a cellular component which cooperates with a purine metabolic pathway enzyme is administered to an individual in a manner appropriate for introducing the drug into affected cells. A drug of the present invention may also be administered in combination with other drugs known to be effective in treatment or with one or more additional drugs of the present invention. One or more drugs affecting a single target or affecting one or more targets in the pathway may be administered to increase the effectiveness of inhibition. The form in which the drug(s) will be administered is determined by the type of drug used, as will the route of administration and the quantity given.

For example, in the case of an individual in whom cervical dysplasia or cervical carcinoma is present, a drug which is able to inhibit the activity of the HPV oncogenic products and, thus, inhibit modulation of the cellular gene (e.g., the CK gene, adenylate kinase gene) is administered in a therapeutically effective quantity. Such a drug can be, for example, a peptide which binds domains 1 and/or 2 of E1a or E7, to prevent them from inducing their transactivation activity. Alternatively or in addition, inhibitors of the activated cellular enzymes are administered. In this instance, as well as in other instances of epithelial tumors, the drug(s) can be administered topically or can be injected, infused or otherwise introduced, alone or in combination with other drugs of the present invention or other known therapies.

A further application of the work described herein is identification of existing compounds, analogues of such compounds or new drugs capable of inhibiting or counteracting the effects of DNA tumor viruses, tumor virus factors, or other factors with an equivalent effect on cells. For example, tumor cells which display an elevation of purine metabolic enzyme activity can be exposed in culture to a drug candidate, and then assayed for growth by the incorporation of tritiated thymidine into DNA. Drugs that cause a decrease in growth relative to the untreated control in such an assay or drug candidates which decrease the activity of purine metabolic enzymes in assays in vitro may be used to inhibit growth, transformation, or metastasis by the method of the present invention. A variety of presently-available drugs (described below) can be assessed for their ability to inhibit creatine kinase or adenylate kinase, which seems to work in conjunction with creatine kinase and can serve as models for design of additional drugs for creatine kinase inhibition.

Drugs useful in the present method can be existing substances, analogues of existing substances or substances designed specifically to interfere with the action or effects of DNA tumor viruses, DNA tumor virus factors, or other factors which have an equivalent effect on cells. The following is a description of existing substances known to inhibit creatine kinase, adenylate kinase or adenosine kinase. It will be possible to modify the substances described below to produce analogues which have enhanced characteristics, such as greater specificity for the enzyme or the oncogenic product, enhanced stability, enhanced uptake into cells, tighter binding to the enzyme or the oncogenic product or better inhibitory activity. In addition, based on knowledge of the structural and functional characteristics of the oncogenes and of the cellular genes upon which the oncogenic products act, it is possible to design other drugs useful in the present method.

COMPOSITIONS USEFUL IN THE PRESENT METHOD OF INHIBITING PURINE METABOLIC ENZYMES

Compounds which inhibit CKB and/or other enzymes which participate in purine metabolism, directly or indirectly (e.g., by interacting with enzymes in the pathway) to reduce the velocity of the enzyme will have great value in preventing and/or treating tumors characterized by elevated levels of these enzymes (e.g., cervical tumors). Such tumor cells may require elevated levels of CKB and/or other enzymes which participate in purine metabolism to meet their high energy demands for growth and metastasis. An advantage of drugs that target pathways that seem to be preferentially required by tumor cells, is that they may be specifically toxic to tumor tissues, and thus may lack the general toxicity associated with less specific drugs.

These drugs can be inhibitors, substrate analogs, and/or slow substrates of a purine metabolic enzyme, which when present, reduce the velocity of the enzymatic reaction catalyzed by a purine metabolic enzyme on the natural substrate(s). For example, a transition state analog covalent inhibitor can be applied locally (e.g., in the cervix). In addition, inhibitors of the enzymes that work in conjunction with CKB can now be designed and used, individually, in combination or in addition to other drugs, to make control of the effect on CKB tighter. For example, inhibitors of adenylate kinase, an enzyme that physically and functionally associates with creatine kinase, can be designed. Such drugs, alone or in combination, are useful as antiviral, antitumor agents.

The following are drugs which can be used, alone, in combination, or in combination with existing therapies in the method of the present invention in order to inhibit the purine metabolic enzyme indicated. These drugs, modifications of these drugs, and new drugs can also be used. Suggestions of specific modifications and strategies for designing analogs are presented. It is to be understood that these are just examples of drugs which can be used in the present method and that this is not intended to be limiting in any way.

INHIBITORS OF CREATINE KINASE Drugs
(antitumor, antiviral)

The pathways of biosynthesis and metabolism of creatine and creatine phosphate can be targeted in selecting and designing drugs which may reduce the velocity of the reaction catalyzed by creatine kinase. Drugs targeted to specific steps may rely on structural analogies with either creatine or its precursors. Novel creatine analogs differing from creatine by substitution, chain extension, and/or cyclization may be designed. The substrates of multisubstrate enzymes may be covalently linked, or analogs which mimic portions of the different substrates may be designed. Specifically, the inhibition of the creatine kinase reaction may be facilitated by a covalent link between adenosine 5'-triphosphate (ATP), adenosine 5'-diphosphate (ADP), or an analog of either, and creatine, or an analog, through the reactive terminii of the molecules or via a spacer, such as $(CH_2)_n$:

| a) Creatine-ADP | Creatine-ATP |
| b) Creatine-R-ADP | Creatine-R-ATP | where R is a spacer, such as $(CH_2)_n$.

Replacement of the phosphate backbone or portions of the backbone with methylene groups may facilitate uptake by cells or increase stability. Variations which reduce the net charge of such an analog may also facilitate uptake by cells.

The inhibition of the arginine:glycine amidinotransferase reaction or the guanidinoacetate N-methyl transferase reaction may be possible through a similar strategy. For example, substituents of a drug may mimic the functioanality of the cosubstrate of the N-methyl transferase, S-adenosyl-methionine.

ADDITIONAL EXAMPLES

1. Inhibitors of creatine kinase and analogs of creatine described by Kenyon and co-workers (Rowley, G. L. et al., *J. Am. Chem. Soc.*, 93:5542–5551, (1971); McLaughlin, A. C. and M. Cohn, *J. Biol. Chem.*, 247:4382–4388, (1972); Nguyen, A. C. K., "Synthesis and enzyme studies using creatine analogs", Thesis, Dept. of Pharmaceutical Chemistry, U.C.S.F., (1983)) and others (Lowe, G. and Sproat, B. S., *J. Biol. Chem.*, 255:3944–3951, (1980)); variants with appropriate modifications to enhance activity or uptake by cells.

EXAMPLES a) 1,3Dicarboxy-methyl-2-imino-imidazolidine

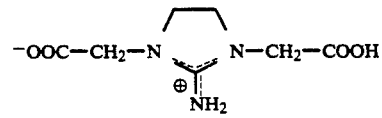

b) 2-Methyl-N,N'-dicarboxymethyl-imidazole

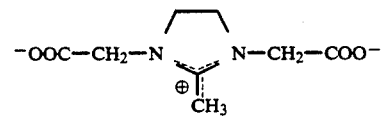

c) Epoxycreatine

2. Compounds described by Walker and co-workers to inhibit creatine kinase (Roberts, J. J. and Walker, J. B., *J. Biol. Chem.*, 260:13502–13508 (1985)).

3. Small organic molecules which inhibit the purine metabolic enzyme, such as:
cyclopropane
butanediones
   2,3-butanedione
-salicylate derivatives
   iodoacetamidosalicylate
iodoacetamide derivatives
   N-(iodoacetamidoethyl)amino naphthalene-1-sulphonate
   N-(4-iodoacetamidophenyl)amino naphthalene-2-sulphonate
benzene derivatives
   e.g., fluorodinitrobenzenes
      1-fluoro-2,4-dinitrobenzene
      5,5'-dithiobis(2-nitrobenzoic acid)
N-cyclohexyl-N-beta(4-methyl-morpholine)
Derivatives or analogues of these molecules which will make them specific to CKB by linking them covalently to the substrates of CKB (i.e., creatine or ADP/ATP).

4. derivatives of ADP, ATP, such as:
a) 2',3'-dialdehyde derivatives of ADP, ATP
b) ATP-V(N-(2-chloroethyl)-N-methyl) amide (a mustard derivative)
c) imidazolides of AMP, ADP, ATP 5. A natural inhibitor in the serum of some patients, such as those with muscular dystrophy (which is a small dialyzable molecule of still unidentified origin).

6. Compounds which uncouple of creatine kinase from the complex: adenylate kinase/translocase/creatine kinase 7. Some of the blockers used in resolving a myocardial infarct are thought to inhibit creatine kinase.

8. Drugs of the general formula:

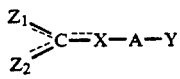

and pharmaceutically acceptable salts thereof.

a) Y is selected from the group consisting of:
—$CO_2H$; —NHOH; —$NO_2$; —$SO_3H$; —C(=O)NHSO$_2$J and —P(=O)(OH)(OJ). In the latter cases, J is hydrogen, $C_1$-$C_6$ straight or branched chain alkyl, $C_2$-$C_6$ straight or branched alkenyl, or aryl group.

b) A is a $C_1$-$C_5$ alkyl, $C_1$-$C_5$ alkenyl, $C_1$-$C_5$ alkynyl, or $C_1$-$C_5$ alkoyl chain. The chain may have 0-2 bulky and/or hydrophobic substituents that are intended to enhance the effectiveness of the compound or to prevent its decomposition by pathways such as that in which creatine is cyclized to creatinine. The substituents are selected independently from the following:

(1) K, where K is a $C_1$-$C_6$ straight or branched alkyl or alkoyl, $C_1$-$C_6$ straight or branched alkenyl. K may also have 0-2 substituents, selected to be reactive with an enzymic nucleophile. A halogen, such as Br or Cl, or an epoxy or acetoxy group are examples of such reactive groups.

(2) An aryl group containing a 1-2 carbocyclic (such as phenyl or naphthyl) or heterocyclic ring (such as indolyl or adeninyl). The aryl group contains 0-2 substituents that could react with an enzymic nucleophile, such as —$CH_2L$ or —$COCH_2L$, in which L is a leaving group such as bromo, chloro, epoxy or acetoxy; and (3) —NH—M, wherein M is hydrogen, $C_1$-$C_4$ straight or branched alkyl or alkoyl, or $C_2$-$C_4$ straight or branched alkenyl.

(c) X is selected from the group consisting of:
$NR_1$, $CHR_1$, $C_1$ alkenyl with an $R_1$ substituent, O and S, wherein $R_1$ is selected from the group consisting of:
(1) Hydrogen;
(2) K as described in (b);
(3) An aryl group as described in (b);
(4) $C_5$-$C_0$ α-amino-w-methyl-ω-adenosylcarboxylic acid attached via the ω-methyl carbon;
(5) $C_5$-$C_9$ α-amino-ω-aza-ω-methyl-ω-adenosylcarboxylic acid attached via the ω-methyl carbon; and
(6) $C_5$-$C_9$ α-amino-ω-thia-ω-methyl-ω-adenosylcarboxylic acid attached via the ω-methyl carbon.

(d) If A is chosen as a $C_1$ alkenyl group, then X must also be chosen as an alkenyl group, and if X is chosen as a $C_1$ alkenyl group, then A must be an alkenyl group, wherein A and X are connected by a double bond.

(e) $Z_1$ and $Z_2$ are chosen independently from the group consisting of: =O, —$NHR_2$, —$CH_2 R_2$, —$NR_2OH$; wherein, $Z_1$ and $Z_2$ may not both be =O and wherein R is selected from the group consisting of:
(1) Hydrogen;
(2) K as described in (b);
(3) An aryl group as described in (b);
(4) $C_4$-$C_8$ α-amino-carboxylic acid attached via the ω-carbon;
(5) B, wherein B is selected from the group consisting of: —$CO_2H$, —NHOH, —$SO_3H$, —$NO_2$, —OP(=O)(OH)(OJ) and —P(=O)(OH)(OJ). As above, J is either hydrogen, $C_1$-$C_6$ straight or branched alkyl, $C_2$-$C_6$ straight or branched alkenyl, or aryl. B is optionally connected via a linker, such as a $C_1$-$C_6$ alkyl, $C_2$ alkenyl, or $C_1$-$C_2$ alkoyl;

(6) —D—E, wherein D is selected from the group consisting of: $C_1$-$C_3$ straight or branched alkyl, $C_2$-$C_3$ straight or branched alkenyl, $C_1$-$C_3$ straight alkoyl, aryl, and aroyl. E is selected from the group consisting of: —(PO$_3$)$_n$NMP, where n is 0-2 and NMP is a ribonucleotide monophosphate connected via the 5'-phosphate, 3'-phosphate or the aromatic ring of the base; —[P(=O)(OCH)(O)]$_m$—Q, where m is 0-3 and Q is a ribonucleoside connected via the ribose or the aromatic ring of the base; —[P(=O)(OH)(CH)]$_m$—Q, where m is 0-3 and Q is a ribonucleoside connected via the ribose or the aromatic ring of the base; and an aryl group containing 0-3 substituents, such as a halogen (Cl, Br) or a group represented by the formula: —OG, —C(=O)G, or —$CO_2G$, in which G is a $C_1$-$C_6$ straight or branched alkyl, $C_2$-$C_6$ straight or branched alkenyl, or $C_1$-$C_6$ straight or branched alkoyl. E maybe attached at any point to D.

If D is an alkyl or alkenyl group, it may be connected at either or both ends by an amide linkage. An amide linkage can be in either orientation (—CONH— or —NHCO—), and if two amide linkages are present their orientations may be the same or different.

(7) —E, wherein E is as described above in (6) and if E is aryl, E may be linked by an amide linkage, which can be in either orientation.

(f) If $R_1$ and at least one $R_2$ group are present, $R_1$ may be connected by a single or double bond to an $R_2$ group to form a cycle of 5 to 7 members.

(g) If two $R_2$ groups are present, they may be connected by a single or double bond to form a cycle of 5-7 members.

The following drugs, which are examples of those represented by the general formula, can be used in the present method. The identifying numbers are those found in the Chemical Abstracts Registry Database (accessible through STN/CAS online). The structure of creatine is shown also, for comparison.

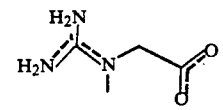

Creatine
57-00-1

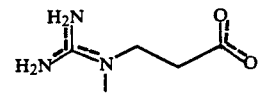

Homocreatine

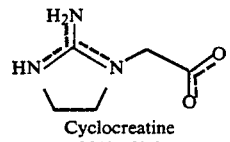

Cyclocreatine
35404-50-3

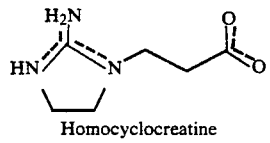

Homocyclocreatine
84714-46-5

-continued

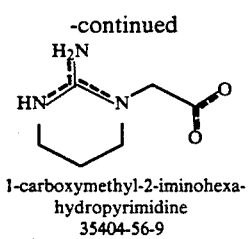
1-carboxymethyl-2-iminohexa-
hydropyrimidine
35404-56-9

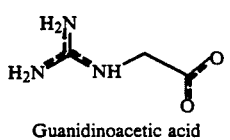
Guanidinoacetic acid

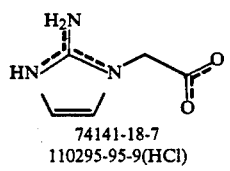
74141-18-7
110295-95-9(HCl)

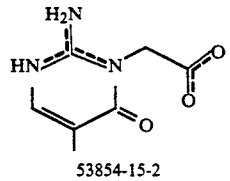
53854-15-2

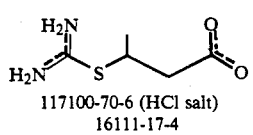
117100-70-6 (HCl salt)
16111-17-4

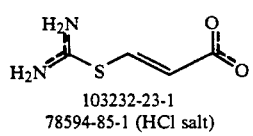
103232-23-1
78594-85-1 (HCl salt)

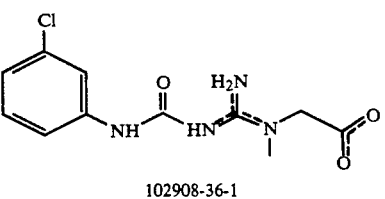
102908-36-1

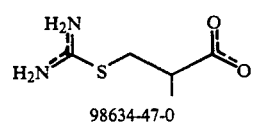
98634-47-0

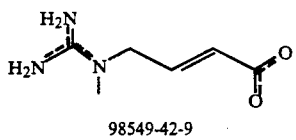
98549-42-9

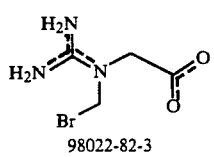
98022-82-3

-continued

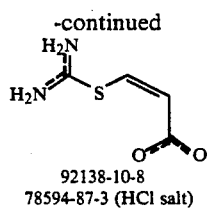
92138-10-8
78594-87-3 (HCl salt)

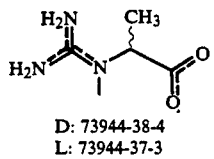
D: 73944-38-4
L: 73944-37-3

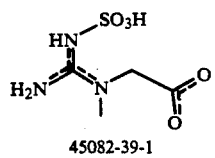
45082-39-1

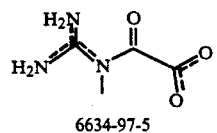
6634-97-5

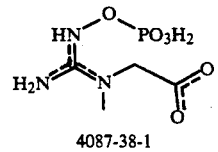
4087-38-1

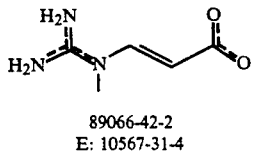
89066-42-2
E: 10567-31-4
Z: 10567-30-3

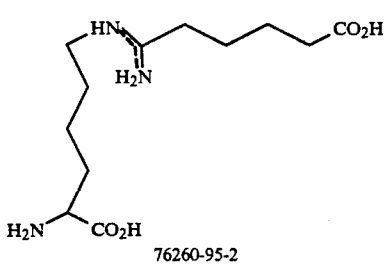
76260-95-2

INHIBITORS OF ADENYLATE KINASE

1. Multi-substrate inhibitors (Valentine, N., et al., *Am. J. Hematol.*, 32(2):143–145 (1989); Gustav, E., et al., *JBC*, 248:1121–1123 (1973)).

a) $p^1,p^5$-Di(adenosine-5')pentaphosphate b) The above compound in which methylene groups replace some or all of the phosphate groups, to facilitate uptake by cells.

c) $AP_4A$ $P_1,P_4$-(diadenosine-5')tetraphosphate and its methylene substitutions.

2. Elemental sulfur and its derivatives (Conner, J. and P. J. Russel, *Research Communications*, 113(1):348–352 (1983)).

3. Adriablastin (Toleikis, A. I, et al., *Biokhimiya*, 53(4):649–654 (1988)).

4. 5,5'-dithiobis-2(nitrobenzoate) (Declerck, P. J. and M. Muller, *Comp. Biochem. & Physio.*, 88(2):575-586 (1987)).

5. Adenosine, di-, tri-, tetraphosphopyridoxals (Yasami, T., et al., *FEBS Lett.*, 229(2):261-264 (1988)).

6. Potassium ferrate (Crivellone, M. D., et al., *J. Biol. Chem.*, 260(5):2657-2661 (1985)).

7. 8-Azido-2 –0-dansyl-ATP (Chuan, H., et al., *J. Bio. Chem.*, 264(14):7981-7988 (1989)).

INHIBITORS OF ADENOSINE KINASE 1. 5-iodotubercidin (from sponge of genus Echinodictyum) (Weinberg, J. M., et al., *Am. J. Physiol.*, 254(3p+2) pF311-322, (1988)).

2. Two very potent inhibitors from marine sources
   4-Amino-5-bromo-pyrrolo[2,3-d]pyrimidine
   5'-Deoxy-5-iodotubercidin (from red alga *Hypnea Valentiae*) (Davies, L. P., et al., *Biochem. Pharm.*, 33(3):347-355 (1984)).

3. Clitocine and its derivatives (Moss, R. J., et al., *J. Med. Chem.*, 31(4):786-790 (1988)).

A link between transformation by DNA tumor viruses and the increased activity and expression of the brain isozyme of creatine kinase has been demonstrated, suggesting that high levels of CKB are needed for the biochemical events triggered during oncogenesis. Alterations in energy metabolism seem to be playing an active role in these malignancies. Therefore, 14 creatine analogs or guanidino compounds (including inhibitors of creatine kinase and/or slow substrates, which, in the presence of the natural substrate(s), act to reduce the velocity of the reaction catalyzed by creatine kinase on its natural substrate) were synthesized or purchased and studied for their effects on the growth of several tumor cell lines, especially on those which have high levels of CKB. Under the conditions used in the assay, and on the specific cell lines tested, the ten compounds in Table 4 showed little or no activity (see Example 6).

In contrast, as shown in Examples 2-5, four of the creatine analogs inhibited the growth of tumor cell lines in culture. The drugs, homocyclocreatine, cyclocreatine, 1-carboxymethyl-2-iminohexahydropyrimidine, and guanidinoacetate, which are slow substrates for creatine, showed different patterns of activity against a panel of cell lines. However, the patterns for homocyclocreatine and 1-carboxymethyl-2-iminohexahydropyrimidine were similar in that the cell lines affected were the same and the degrees of inhibition by either drug were similar. The latter two drugs preferentially inhibited the growth of the prostate and cervical cell lines which are metastatic in origin as compared with nonmetastatic prostate and cervical cell lines. Furthermore, two non-transformed cell lines, MRC-5 and Vero, which are tissue culture versions of "normal" cell lines, were largely unaffected by these two drugs, suggesting that they may spare normal cells and may have a low toxicity in vivo.

Cyclocreatine and guanidinoacetic acid each showed a different pattern of activity against the panel of cell lines. Cyclocreatine and guanidinoacetate both strongly inhibited the growth of three colon tumor cell lines tested. In addition to the colon cell lines, cyclocreatine affected many of the other cell lines tested. In contrast, the only other line strongly affected by guanidinoacetate was the BALB/C 3T3 line. (The data for guanidinoacetic acid is from two separate experiments and as such is not as extensive as that for the other three drugs.) The specificity of the drugs for certain cell lines suggests that these drugs lack the indiscriminate toxicity observed with other anti-tumor therapies.

The present invention will be further illustrated by the following examples, which are not intended to be limiting in any way. The Materials and Methods following immediately were used in Examples 1-6.

Materials and Methods

Compounds

The compounds used in these studies were homocyclocreatine (1-carboxyethyl-2-iminoimidazolidine), cyclocreatine (1-carboxymethyl-2-iminoimidazolidine), 1-carboxymethyl-2-iminohexahydropyrimidine and guanidinoacetate (glycocyamine). The synthesis of homocyclocreatine was carried out as described by Roberts and Walker (Roberts, J. J. and J. B. Walker, *Arch. Biochem. Biophys.*, 220:563-571 (1983)). The syntheses of cyclocreatine and 1-carboxymethyl-2-iminohexahydropyrimidine were carried out as described by Griffiths and Walker (Griffiths, G. G. and J. B. Walker, *J. Biol. Chem.*, 251:2049-2054 (1976)). Guanidinoacetate was obtained from Sigma Chemical Corp. (St. Louis, Mo.).

Tumor Cell Lines

A variety of tumor cell lines were obtained from the American Type Culture Collection (ATCC, Rockville, Md.). The neuroendocrine-derived tumor cell lines, such as the small cell lung carcinoma cell line, were grown as cell suspensions in flasks and were replated and fed twice a week. The other cell lines were grown attached on plastic plates and were replated at 90% confluency. All cell lines were grown in media supplemented with fetal bovine serum.

The properties of the cell lines used in these studies have been described (ATCC Catalogue of Cell Lines and Hybridomas, 6th edition, Hay et al., Eds., 1988). Some of the the properties of the cell lines, including the origin, tumorigenicity, and markers, are summarized below.

Prostate Cell Lines

DU145: Prostate carcinoma, metastasis to brain, Human

Eagle's MEM, 90%; Fetal Bovine Serum (FBS), 10%

Isolated from a lesion in the brain of a patient with widespread metastatic carcinoma of the prostate and a three year history of lymphocytic leukemia. The cells have an epithelial-like morphology, are weakly positive for acid phosphatase, are not hormone sensitive, and form colonies in soft agar. Tumorigenic in nude mice. (Mickey, D. C. et al., *Cancer Res.*, 37: 4049-4058 (1977); Stone, K. R. et al., *Int. J. Cancer*, 21:274-281 (1978)).

LNCaP.FGC: Prostate adenocarcinoma, metastasis to lymph node, Human

RPMI 1640, 90%; FBS, 10%

Isolated from a needle aspiration biopsy of the left supraclavicular lymph node of a 50 year-old male with metastatic carcinoma of the prostate. The cell line produces prostatic acid phosphatase and prostate specific antigen, and has androgen receptors. Tumorigenic in nude mice. (*Models of Prostate Cancer*, G. P. Murphy (ed.), pp. 115-132, Alan R. Liss, Inc., New York, 1980; *Cancer Res.*, 43:1809-1818, 1983; *Cancer Genet. Cytogenet.*, 11:399-404 (1984)).

PC-3: Prostate adenocarcinoma, Human Eagle's MEM, 90%; FBS, 10%

Isolated from a grade IV prostatic adenocarcinoma from a 62 year-old male. The cell line has low acid phosphatase activity, grows in soft agar, and can grow in suspension. Tumorigenic in nude mice. (*Invest. Urology* 17:16-23, 1979: *Cancer Res.*, 40:524-534, 1980).

Colon Cell Lines

SW48: Colon adenocarcinoma, Human
Leibovitz's L-15 Medium, 90%; FBS, 10%

Isolated from a grade IV colorectal adenocarcinoma, which encircled the bowel of an 82 year-old female. The cells have an epithelial-like morphology, and low levels of CEA. Tumorigenic in nude mice. (Leibovitz, A. et al., *Cancer Res.*, 36:4562-4569, 1976; J. et al., *J. Natl. Cancer Inst.*, 59: 221-226, 1977).

SW403: Colon adenocarcinoma, Human
Leibovitz's L-15 Medium, 90%; FBS, 10%

Isolated from a grade III colorectal adenocarcinoma, which almost encircled the bowel of a 51 year-old female. The cells have an epithelial-like morphology, and produce carcinoembryonic antigen (CEA). Tumorigenic in nude mice. (Leibovitz, A. et al., *Cancer Res.* 36:4562-4569, 1976; Fogh, J. et al., *J. Nat. Cancer Inst.*, 59:221-226 (1977)0.

SW1116: Colon adenocarcinoma, Human
Leibovitz's L-15 Medium, 90%; FBS, 10%

Isolated from a grade II adenocarcinoma of the colon, which extended into the muscularis of a 75 year-old male. Melanosis was observed. The cells have an epithelial-like morphology, show brush borders, and produce high levels of CEA. (Leibovitz, A. et al., *Cancer Res.*, 36:4562-4569, 1976)

Cervical Cell lines

C-33A: Cervical carcinoma, Human
Eagle's MEM (with non-essential amino acids and sodium pyruvate), 90%; FBS, 10%

Isolated from a cervical cancer biopsy from a 66 year-old female. The cells have an epithelial-like morphology. Tumorigenic in nude mice. (Auersperg, N., *J. Natl. Cancer Inst.*, 32:135-148, 1964)

CaSki: Cervical epidermoid carcinoma, Human
RPMI 1640, 90%; FBS, 10%

Isolated from an epidermoid carcinoma of the cervix metastatic to the mesentery of the small bowel of a 40 year-old patient. The cells express tumor-associated antigen and produce the beta subunit of human chorionic gonadotropin. (Pattillo, R. A. et al., *Science* 196:1456-1458, 1977).

SiHa: Cervical squamous carcinoma, Human
Eagle's MEM (with non-essential amino acids and sodium pyruvate), 90%; FBS, 10%

Isolated from a primary tissue surgical sample from a 55 year-old patient. Epithelial-like morphology. Forms tumors in nude mice. (Friedl, F. et al., *Proc. Soc. Exp. Biol. Med.*, 135:543-545, 1979).

HeLa: Cervical epitheloid carcinoma, Human
Eagle's MEM with non-essential amino acids and Earle's BSS, 90%; FBS, 10%

Isolated from a cervical carcinoma of a 31 year-old (*Cancer Res.*, 12:264, 1952). Epithelial-like morphology.

ME-180: Cervical epidermoid carcinoma, Human
McCoy's 5a medium, 90%; FBS, 10%

Isolated from an omental metastasis of a rapidly spreading cervical carcinoma from a 66 year-old (Sykes, et al., *J. Nat. Cancer Inst.*, 45:107-122, 1970). The tumor was a highly invasive squamous cell carcinoma and shows epithelial-like morphology in culture. Tumorigenic in nude mice.

Lung Cell Lines

NCI-H$_{69}$: Small cell carcinoma of the lung, Human
RPMI 1640, 90%; FBS, 10%

Isolated from the pleural fluid of a 55 year-old male with small cell carcinoma of the lung. Forms colonies in soft agar and grows in suspension. Has small cell carcinoma morphology and APUD characteristics. Tumorigenic in nude mice. (Gazdar, A. et al., *Cancer Res.* 40:3502-3507, 1980).

MRC-5: Diploid non-transformed lung cell line, Human

Eagle's Basal Medium with Hanks' BSS, 90%; FBS, 10% Derived from normal lung tissue of a 14 week-old fetus. Fibroblast-like morphology. (*Nature* 277:168-170, 1970).

Bone Cell Lines

U-2 OS: Primary osteogenic sarcoma, Human McCoy's 5a medium, 85%; FBS, 15% Derived from a sarcoma from the tibia of a 15 year-old. Epithelial-like morphology (*Int. J. Cancer*, 2:434-447, 1967).

Saos-2: Primary osteogenic sarcoma, Human
McCoy's 5a medium, 85%; FBS 15%

Isolated from an 11 year-old. This line has an epithelial-like morphology consistent with osteogenic sarcoma. The cells do not form tumors in nude mice. (In: Human Tumor Cell In Vitro, pp. 115-159, J. Fogh, (ed.), Plenum Press, New York, 1975)

Kidney Cell Lines

293: Transformed primary embryonal kidney, Human
Eagle's MEM, 90%; horse serum, 10%

The 293 cell line was derived from primary human embryonal kidney cells transformed with sheared DNA from human adenovirus type 5. (*J. Gen. Virol.*, 36:59-72, 1977)

Vero: Normal kidney, African Green Monkey Medium 199, 95%; FBS, 5%

Initiated from the kidney of a normal adult African Green Monkey (Yasumura, Y. and Kawakita, Y., *Nippon Rinsho*, 21:1209, 1963). Fibroblast-like morphology.

Embryonal Cell Lines

BALB/3T3: Embryonal tissue, Mouse
Dulbecco's modified Eagle's medium, 90%; calf serum, 10%

Isolated from disaggregated mouse embryos. The line is non-tumorigenic, and shows contact inhibition. (Aaronson, S. A. and Todaro, G. T., *J. Cell Physiol.*, 72:141-148, 1968).

F9: Embryonal carcinoma, Mouse
Dulbecco's modified Eagle's medium with 4.5 g/L glucose, 85%; FBS, 15%

Initiated from a testicular teratocarcinoma of a mouse (Bernstine et al., *Proc. Natl. Acad. Sci. U.S.A.*, 70:3899-3903, 1973). The cell line can be induced to differentiate into parietal endoderm under certain culture conditions.

Growth Assays

The rate of incorporation of thymidine into DNA was adopted as a measure of cell growth. To test the effect of several creatine analogs (inhibitors of creatine kinase and/or slow substrates, referred to here as drugs), on the growth of cell lines, the cells were harvested and replated at an appropriate density. The next day, drugs were added at the indicated concentration. Tritiated thymidine ($^3$H-thymidine) was added to a final concentration of 2 $\mu$Ci/ml either one hour or twenty-four hours before the cells were harvested, depending on the length of the experiment. Treated cells were harvested by one of two methods. In the first method, cells were lysed by the addition of 10% trichloroacetic acid or 10% sodium dodecylsulfate. Precipitated proteins were removed by centrifugation and the DNA was blotted onto 3MM filter paper. Filters were washed sequentially with methanol and acetone, then dried and counted in a liquid scintillant. In the second method, media was removed by aspiration and the cells were incubated for five minutes in 100 $\mu$l of trypsin (0.25%) to detach the cells. Cells were harvested with a Skatron cell harvester, collected on 3MM filter paper, and counted in a liquid scintillant to determine the associated radioactivity. All samples for each time point were taken in duplicate or triplicate, and each experiment was repeated at least twice. To obtain values for growth as a percent of control for drug treated cultures, the incorporation of $^3$H-thymidine in the presence of drug was divided by the incorporation of $^3$H-thymidine in the absence of drug and was then multiplied by a factor of 100.

Protein Extracts from Tumor Cells

Treated or untreated cell lines were washed three times with phosphate buffered saline (PBS). Cells were then scraped from the plates and lysed by three cycles of freeze-thawing. Particulate matter was removed by centrifugation and the supernatant was used as the protein extract.

Creatine Kinase Activity

Total creatine kinase activity was determined in a coupled reaction, where the production of ATP by creatine kinase is coupled to the reduction of nicotinamide adenine dinucleotide phosphate (NADP). The progress of the reaction is monitored spectrophotometrically at 340nm. The coupled reactions are:

$$\text{Creatine phosphate} + \text{ADP} \xrightleftharpoons{CK} \text{Creatine} + \text{ATP}$$

$$\text{ATP} + \text{Glucose} \xrightleftharpoons{HK} \text{Glucose-6-phosphate} + \text{ADP}$$

$$\text{Glucose-6-phosphate} + \text{NADP} \xrightleftharpoons{G6PD} \text{6-phosphogluconate} + \text{NADPH}$$

CK = Creatine kinase
HK = Hexokinase
G6PD = Glucose-6-phosphate dehydrogenase

The coupled reactions were carried out so that the reaction catalyzed by creatine kinase was the rate limiting reaction. Hexokinase and G6PD were in excess. Therefore, the rate of reduction of NADP to NADPH was proportional to creatine kinase activity.

Another test was adopted to assess the proportion of total creatine kinase activity attributable to the brain isoenzyme. The enzyme mixture or cell extract was fractionated by electrophoresis on a 0.8% agarose gel at 90 volts/hr. The gel was then immersed in the constituents of the coupled reaction described above, with appropriate salts. A colored visible band is generated in the gel at the locations of enzyme activity (Creatine Kinase Kit #715AM, Sigma Chemical Corp.). The migration of each CK isozyme is different, allowing the bands and the activities associated with each isozyme to be distinguished from one another. One can locate the brain isozyme in the gel by running a sample of pure CKBB as a marker.

EXAMPLE 1

Level of Creatine Kinase Brain Isozyme Activity in Different Tumor Cell Lines

Cell lines were grown in tissue culture, were harvested at confluency, and protein extracts were made. To determine total creatine kinase (CK) activity, the protein extracts were assayed spectrophotometrically using coupled reactions (Sigma Kit #49 UV). The extracts were also fractionated on 0.8-1.0% agarose gels, to separate the CK isoenzymes, and were assayed for CK activity directly in the gel, using Sigma Kit #715 AM. The values determined for total creatine kinase activity ($\Delta A_{340}/\text{min}/A_{590} \times 100$, corrected for protein concentration) for the above tumor lines are listed in Table 1. The CK isozyme patterns generated in an agarose gel by the coupled reaction and staining procedure described above, were determined for extracts from several tumor cell lines, including small cell lung carcinoma line NCI-H69, prostate carcinoma lines LNCaP.FGC and DU 145, and cervical carcinoma line C-33A. Pure CKBB (brain isozyme), CKMM (muscle isozyme), and CKMB (cardiac isozyme) were run on the gel as controls to indicate the locations of each isozyme in the gel. It was clear from this analysis (data not shown) that brain creatine kinase is the predominant isozyme and thus represents the majority of the creatine kinase activity of these tumor cell lines. Although most normal cells express no detectable CKB activity, CKB levels are elevated in many patients with malignancies, including lung, prostate and cervical cancers, and CKB is used as a marker for small cell lung carcinoma.

TABLE I

| Creatine Kinase Activity in Different Tumor Cell Lines | | |
|---|---|---|
| Tissue | Cell Line | $\Delta A_{340}/\text{min}/A_{590} \times 100$ |
| Lung | MRC.5 | 3 |
|  | NCI-H69 | 50 |
| Cervical | C-33A | 10 |
|  | CaSki | 0.5 |
|  | SiHa | 2 |
|  | HeLa | 10 |
|  | ME180 | 38 |
| Bone | U-2 OS | 1 |
|  | Saos-2 | 2 |
| Kidney | Vero | <1 |
|  | 293 | 27 |
| Prostate | PC-3 | 1 |
|  | LNCaP.FGC | 30 |
|  | DU 145 | 15 |
| Colon | SW1116 | 2 |
|  | SW403 | 6 |
|  | SW48 | 3 |
| Embryonal | BALB/c3T3 | 2 |
|  | F9 | <1 |

EXAMPLE 2

Effect of Homocyclocreatine on Tumor Cell Lines

Homocyclocreatine is a cyclic derivative of creatine

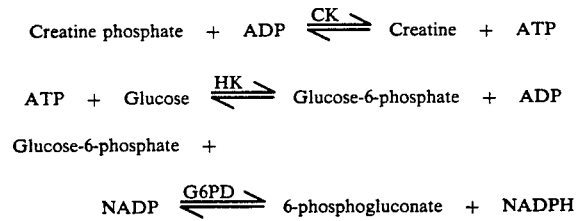

Creatine

-continued

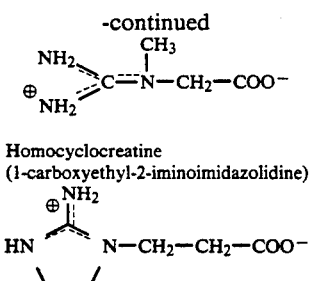

Homocyclocreatine
(1-carboxyethyl-2-iminoimidazolidine)

Homocyclocreatine was shown to be a poor substrate for rabbit muscle creatine kinase, and was reported to react with creatine kinase 10,000-fold more slowly than creatine. In the reverse reaction, at pH 7.0, homocyclo-creatine-phosphate (0.2 mM homocyclocreatine—P) was 200,000-fold less active than creatine phosphate as a substrate for rabbit muscle creatine kinase. (Roberts, J. J. and J. B. Walker, Arch. Biochem. Biophys., 220:563-571 (1983)) Roberts and Walker also reported that mice fed 2% homocyclocreatine accumulated homocyclocreatine—P in skeletal muscle, brain, and heart. Rats fed a diet of 5% homocyclocreatine accumulated larger amounts of homocyclocreatine-P in the same tissues. Chicks fed a diet containing 5% homocyclocreatine for 16 days similarly accumulated homocyclocreatine—P in muscle, heart and brain tissue, possibly due to the stability of the phosphorylated form. In muscle samples from homocyclocreatine-fed chicks, homocyclocreatine-P regenerated ATP very slowly.

Effect of Homocyclocreatine on Prostate Tumor Cell Line DU 145

Figure 8:
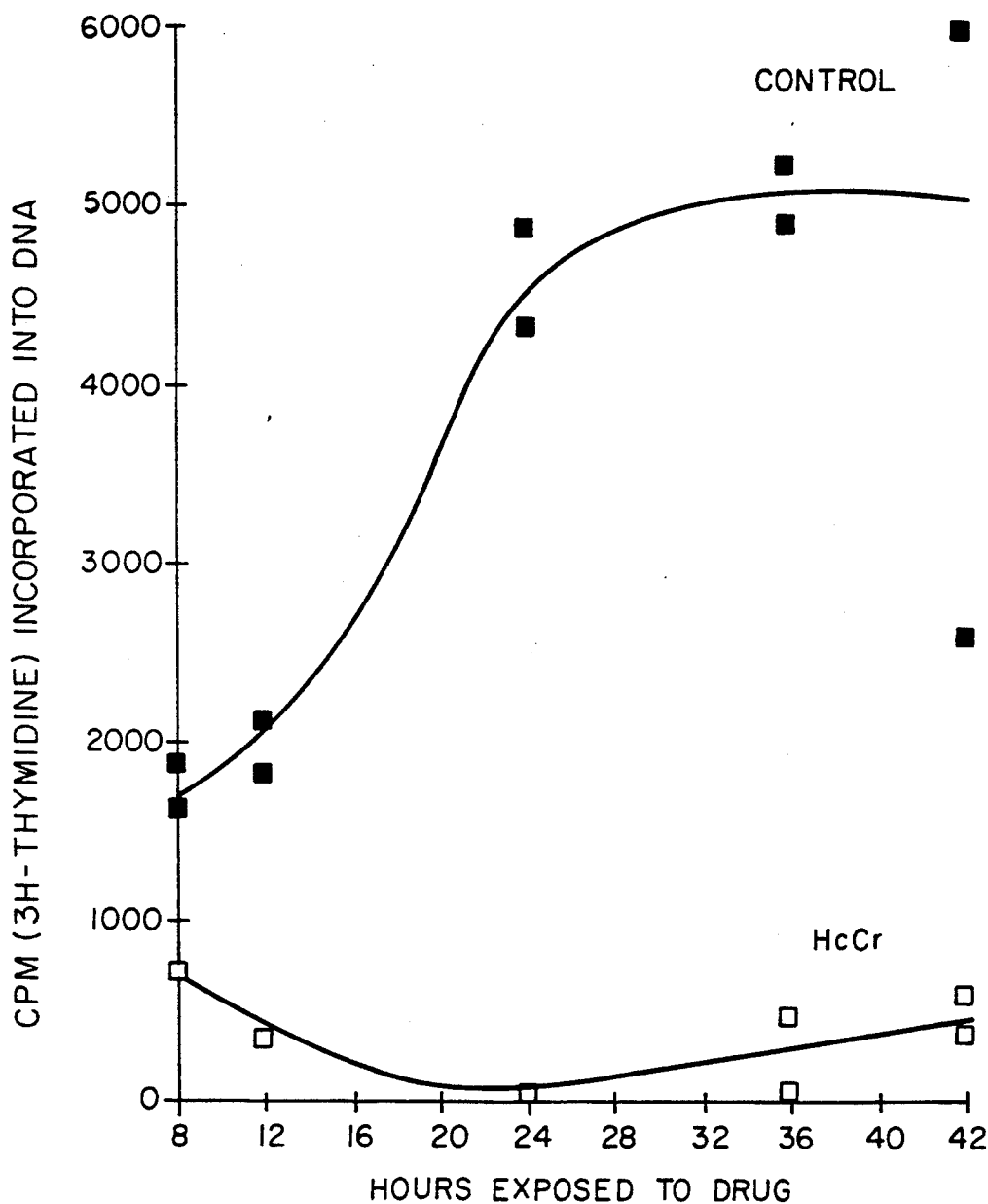
FIG. 8 is a graph depicting the effect of 30 mM homocyclocreatine exposure for 8 to 42 hours on the rate of DNA synthesis in prostate tumor cell line DU 145.

As discussed above, prostate tumor cell line DU 145, derived from a brain metastasis of a patient with prostate cancer, shows a high level of creatine kinase activity, which is predominantly due to the B isozyme. Homocyclocreatine was synthesized as indicated above, and tested for its effect on growth of DU 145 tumor cells. DU 145 cell were replated at a 1:8 dilution, and were treated with 30 mM homocyclocreatine for 8, 12, 24, 36, or 42 hours. The cells were incubated with labeled thymidine ($^3$H-thymidine) for one hour prior to harvesting and counting for incorporation of thymidine into DNA. FIG. 8 shows the incorporation of thymidine into DNA over time in cells treated with homocyclocreatine and in untreated control cells.

In control experiments, tritiated leucine was used to test for incorporation of amino acids as an independent determination of growth. In cells treated with drug, incorporation of tritiated leucine was also decreased. A clonogenicity assay was done as an additional assay of survival and proliferative capacity of homocyclocreatine treated DU 145 cells. DU 145 cells were diluted and plated onto tissue culture-treated plastic dishes and were allowed to grow and form colonies (*Animal Cell Culture, A Practical Approach*, R. I. Freshney, Ed., IRL Press, Oxford-Washington, D. C.). Drug treated cultures were exposed to drug throughout the clonal growth period. Both colony number and size (cells per colony) were strongly reduced in the presence of homocyclocreatine as compared to untreated controls. These independent measures of growth inhibition suggest that the reduction of thymidine incorporation is not due to an artifact related to the assay such as an uptake problem. Furthermore, homocyclocreatine treated cells showed no staining of the mitotic spindle in immunofluorescence studies, although the mitotic spindle was visible in control cells.

Effect of Homocyclocreatine Concentration on Growth of Prostate Tumor Cell Line DU 145 ($ID_{50}$)

Figure 9A:
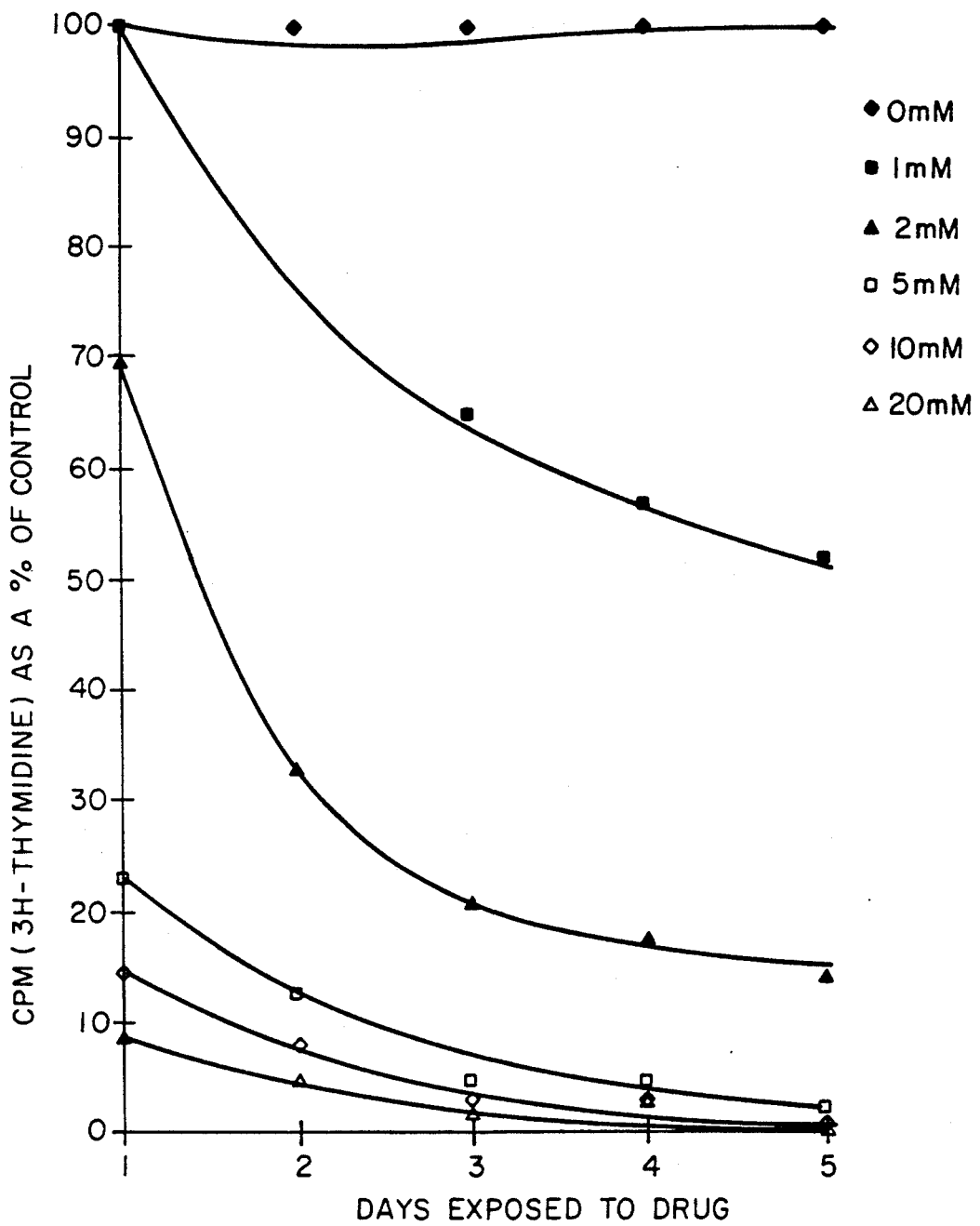
FIG. 9A is a graph depicting the time dependence of the inhibitory effect of different concentrations of homocyclocreatine on DNA synthesis in prostate tumor cell line DU145.

In an attempt to find the minimum effective inhibitory concentration of homocyclocreatine on prostate tumor growth, the concentration of drug added was varied from 0 to 20 mM and monitored DNA synthesis under each regimen by incorporation of $^3$H-thymidine over a period of five days. The drugs were added and each day the media was changed and the drug was replenished. Control cells received new media with no drug addition. FIG. 9A shows an inhibitory effect of 2 mM homocyclocreatine on tumor growth. A concentration of 1 mM homocyclocreatine was observed to have a moderate effect on growth. At this concentration, a longer period of exposure may be required to observe a comparable effect on cell growth.

Figure 9B:
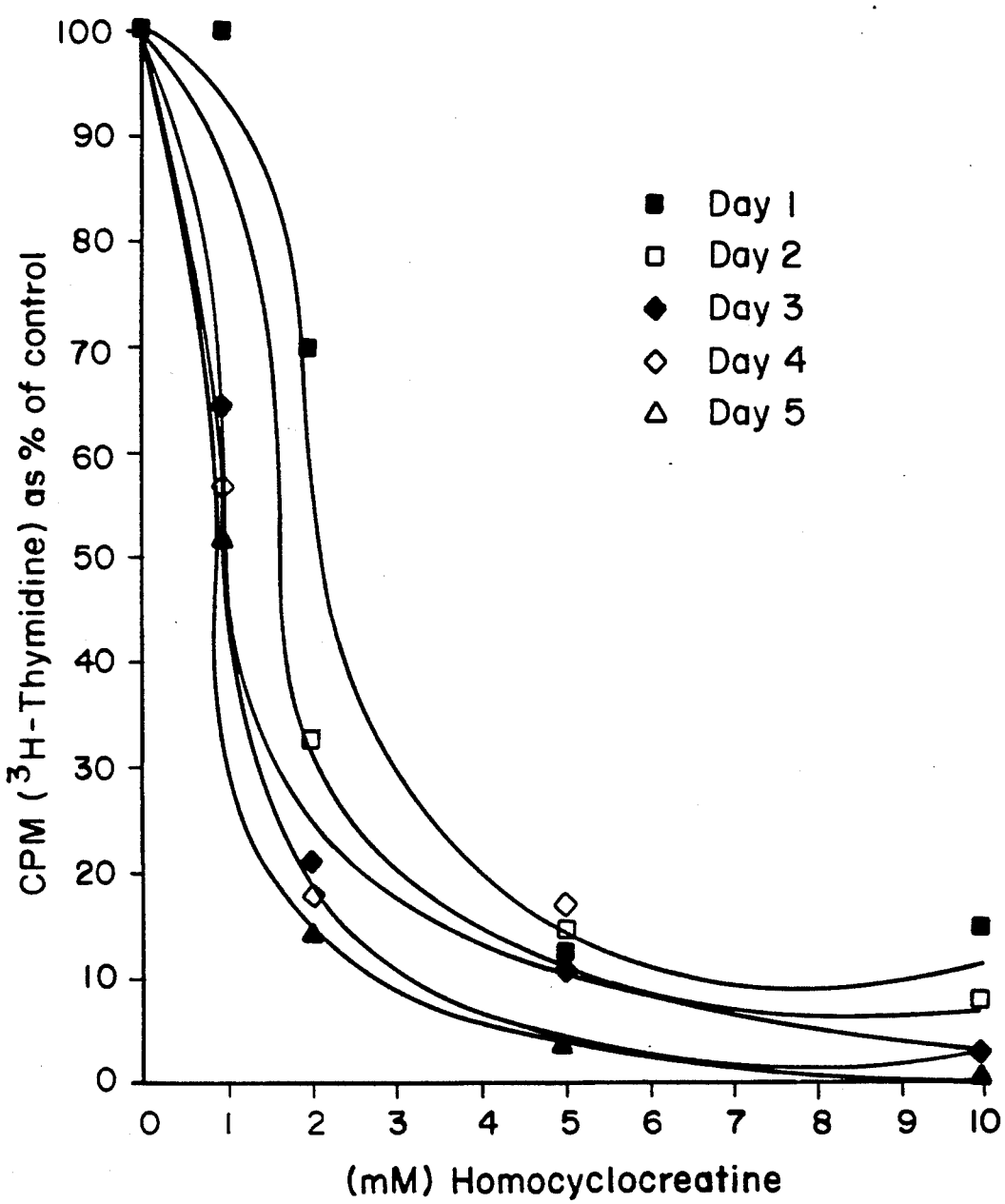
FIG. 9B is a plot of growth as a percent of the untreated control versus the concentration of homocyclocreatine in prostate tumor cell line DU145.
Figure 9C:
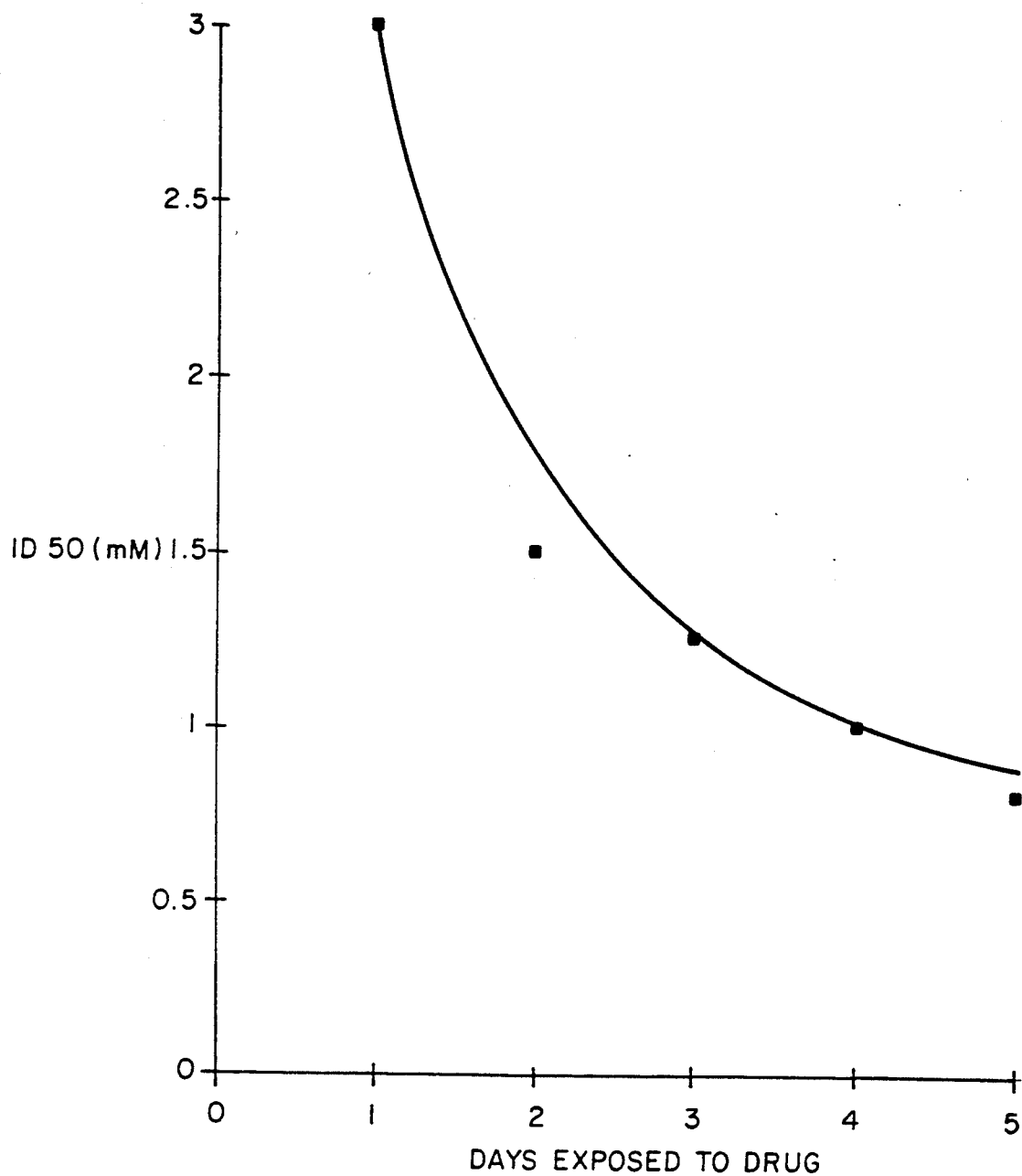
FIG. 9C is a graph depicting the $ID_{50}$ (Mm) For homocyclocreatine in prostate tumor cell line DU 145 as a function of the length of exposure to drug.

FIG. 9B shows a plot of growth as a percent of the untreated control versus the concentration of homocyclocreatine for 1, 2, 3, 4, or 5 days of exposure to the drug. From this curve, the $ID_{50}$ or the concentration at which 50% inhibition of growth is reached for each period of treatment (1-5 days) was determined. FIG. 9C shows a plot of $ID_{50}$ against the number of days of exposure to drug. The values for the $ID_{50}$ range from 3.0 mM homocyclocreatine for one day of treatment to 0.7 mM homocyclocreatine for five days of treatment. Thus, a 50% inhibition of growth of prostate tumor cell line DU 145 was achieved by exposure to 1.0 mM homocyclocreatine for a period of five days.

Homocyclocreatine(20 mM) Irreversibly Arrests Growth of Prostate Tumor Cell Line DU 145

Figure 10A:
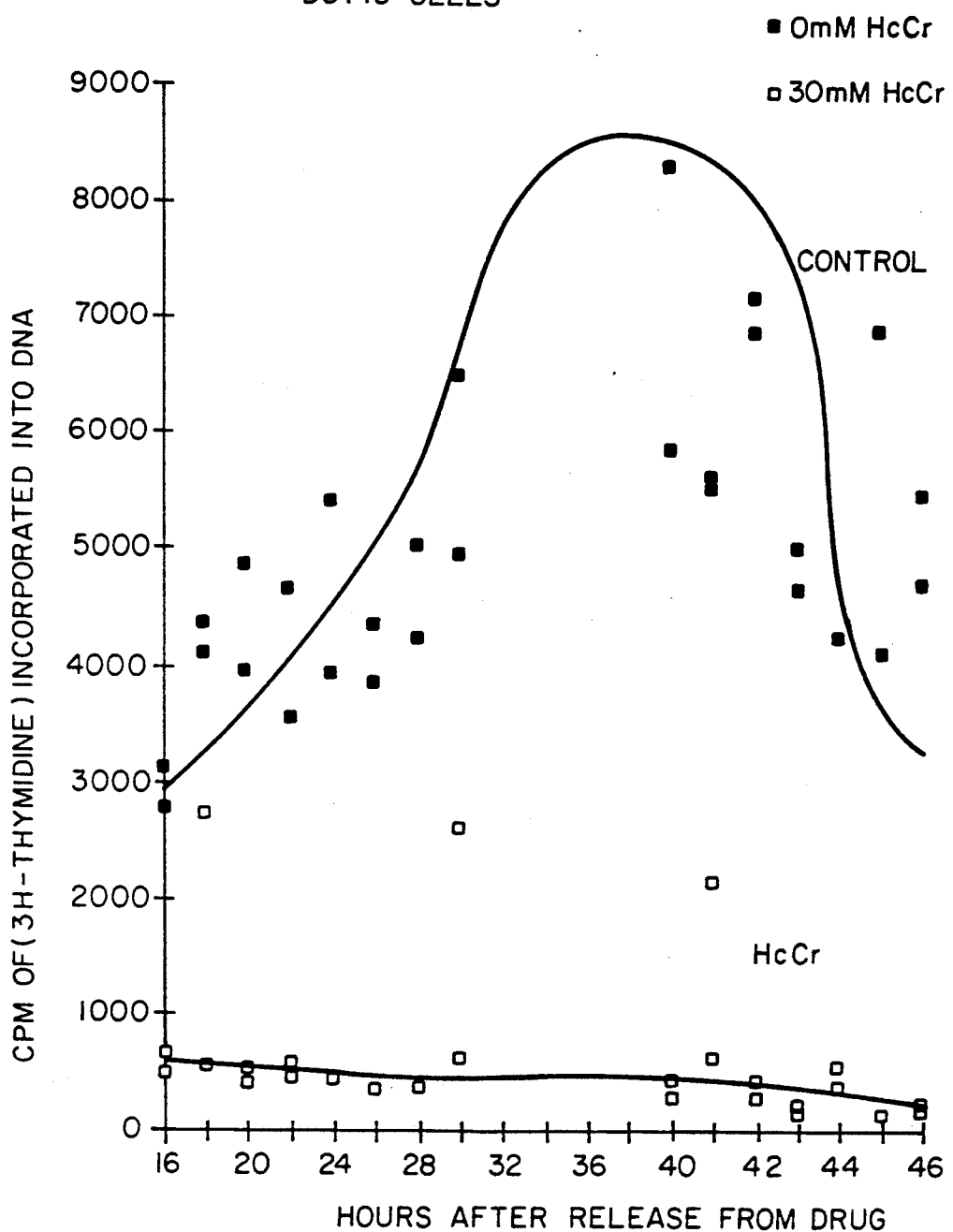
FIG. 10A shows the effect of 0–30 mM drug 16–46 hours after release from drug.

DU 145 cells were grown as described above. Cells were treated with 0 or 30.0 mM homocyclocreatine for 24 hours. The cells were then released from drug exposure and allowed to recover for up to 46 hours. At each hour post-release, a portion of cells was removed from culture, washed, exposed to $^3$H-thymidine, and assayed for DNA synthesis. FIG. 10A shows that cells treated with 30 mM homocyclocreatine were unable to reinitiate DNA synthesis within the time period assayed.

Figure 10B:
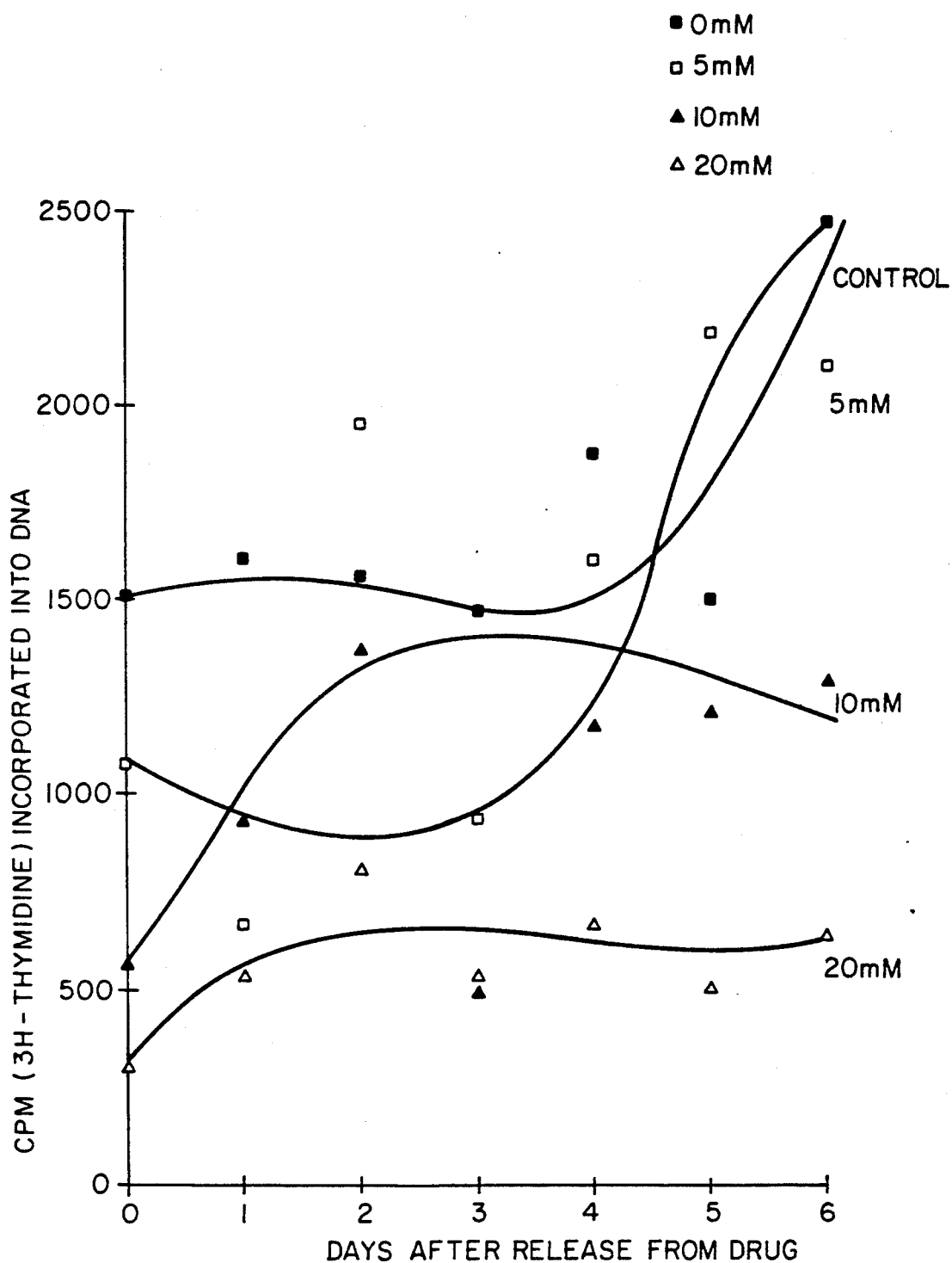
FIG. 10B shows the effects of 0.0, 5.0, 10.0 and 20 mM drug 1/14 6 days after release from drug.

FIG. 10B shows the same type of experiment at concentrations of 0, 5 mM, 10 mM, and 20 mM homocyclocreatine. However, the cells were monitored for a period of six days. Cells were treated with drug for a period of 24 hours, and were washed and released from drug treatment. Samples of cells were removed after 1, 2, 3, 4, 5, and 6 days in culture following release from drug, and assayed for DNA synthesis by incorporation of $^3$H-thymidine into DNA. In this experiment, no reinitiation of DNA synthesis was observed in the tumor cells exposed to 20 mM homocyclocreatine, even six days after release from the drug.

Creatine Does Not Reverse the Inhibitory Effect of Homocyclocreatine on Prostate Tumor Cell Line DU 145

Prostate tumor line DU 145 cells were treated with 10 mM homocyclocreatine alone or with 10 mM homocyclocreatine and creatine (up to 40 mN). The goal of this experiment was to determine whether creatine can compete with homocyclocreatine to prevent the inhibitory effects of the latter compound. The following concentrations (mM) of each compound were used in these experiments:

| Homocyclocreatine | Creatine |
|---|---|
| 0.0 | 0.0 |
| 10.0 | 0.0 |
| 10.0 | 5.0 |
| 10.0 | 10.0 |
| 10.0 | 20.0 |
| 10.0 | 40.0 |

Figure 11:
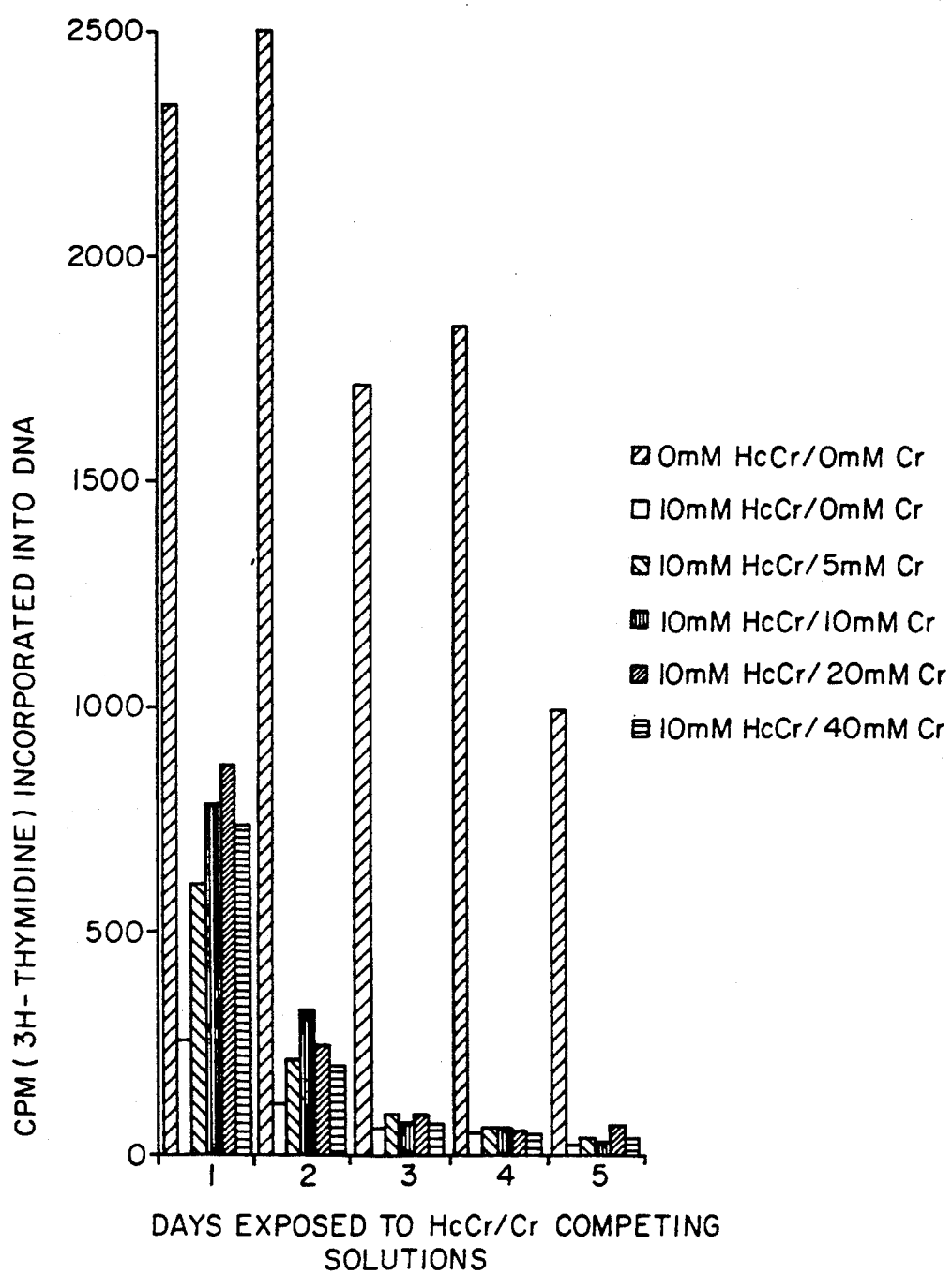
FIG. 11 is a bar graph depicting the time and concentration dependence for the reversal, by creatine addition, of the inhibition of DNA synthesis by homocyclocreatine in prostate tumor cell line DU 145.

At days 1, 2, 3, 4, and 5, a portion of cells was labeled with $^3$H-thymidine and assayed for DNA synthesis. FIG. 11 shows the effect of drug combinations on DNA synthesis after different lengths of exposure to the drug combination. On day one, creatine was able to partly counteract the inhibition of DNA synthesis by homocyclocreatine. By day 2, the reversal of growth inhibition by creatine (5-20 mill) was modest, and creatine failed to reverse the inhibitory effect of homocyclocreatine after 3, 4, or 5 days of exposure to the drug combination. Thus, endogenous creatine is not expected to counteract the inhibitory effect of the drug.

Homocyclocreatine Has No Effect on the Non-transformed Lung Fibroblast Cell Line MRC-5

Figure 12A:
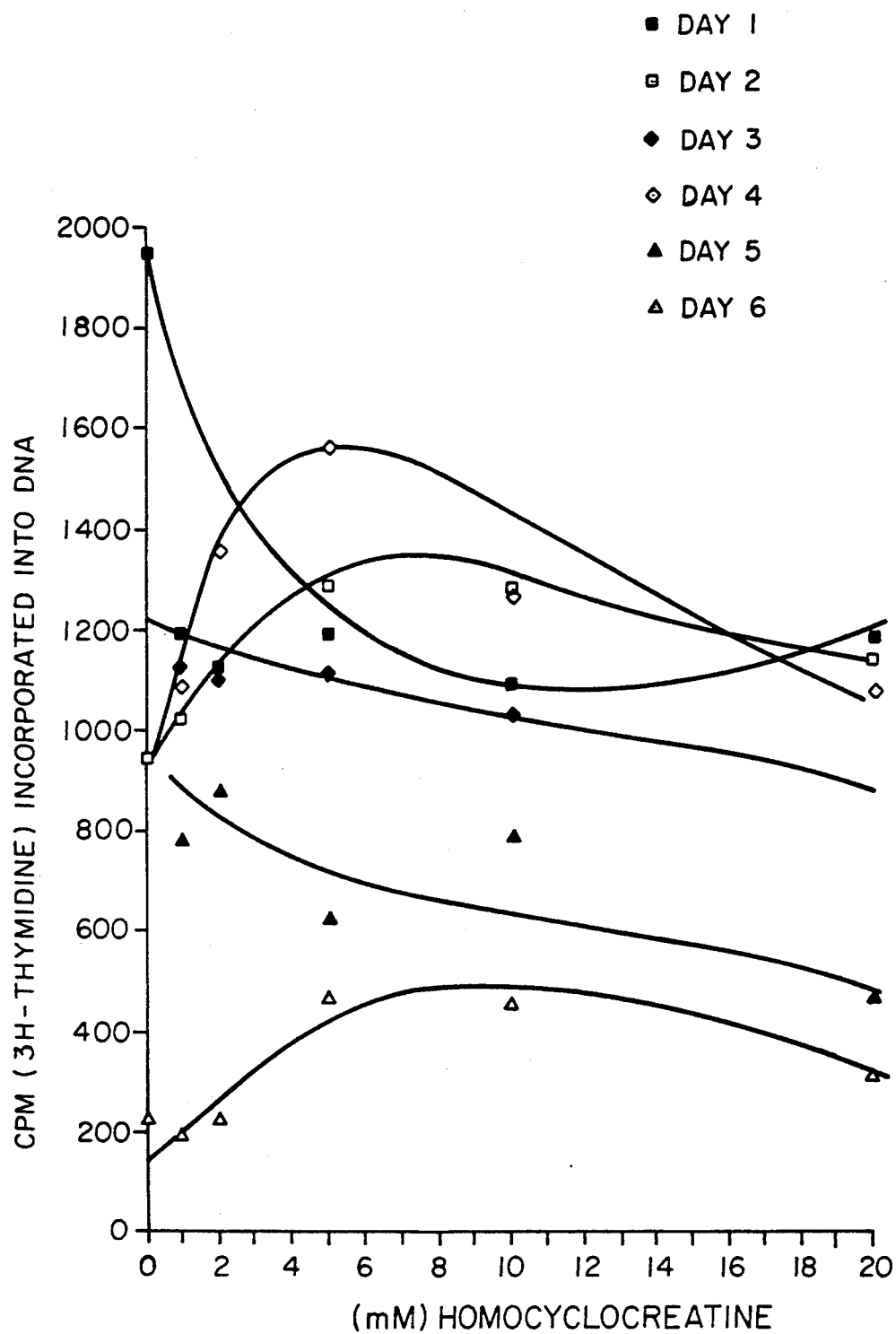
FIG. 12A is a graphic representation of DNA synthesis in non-transformed fibroblast cell line MRC-5 in the presence of 1–20 mM homocyclocreatine after 1–6 days of exposure to drug.
Figure 12B:
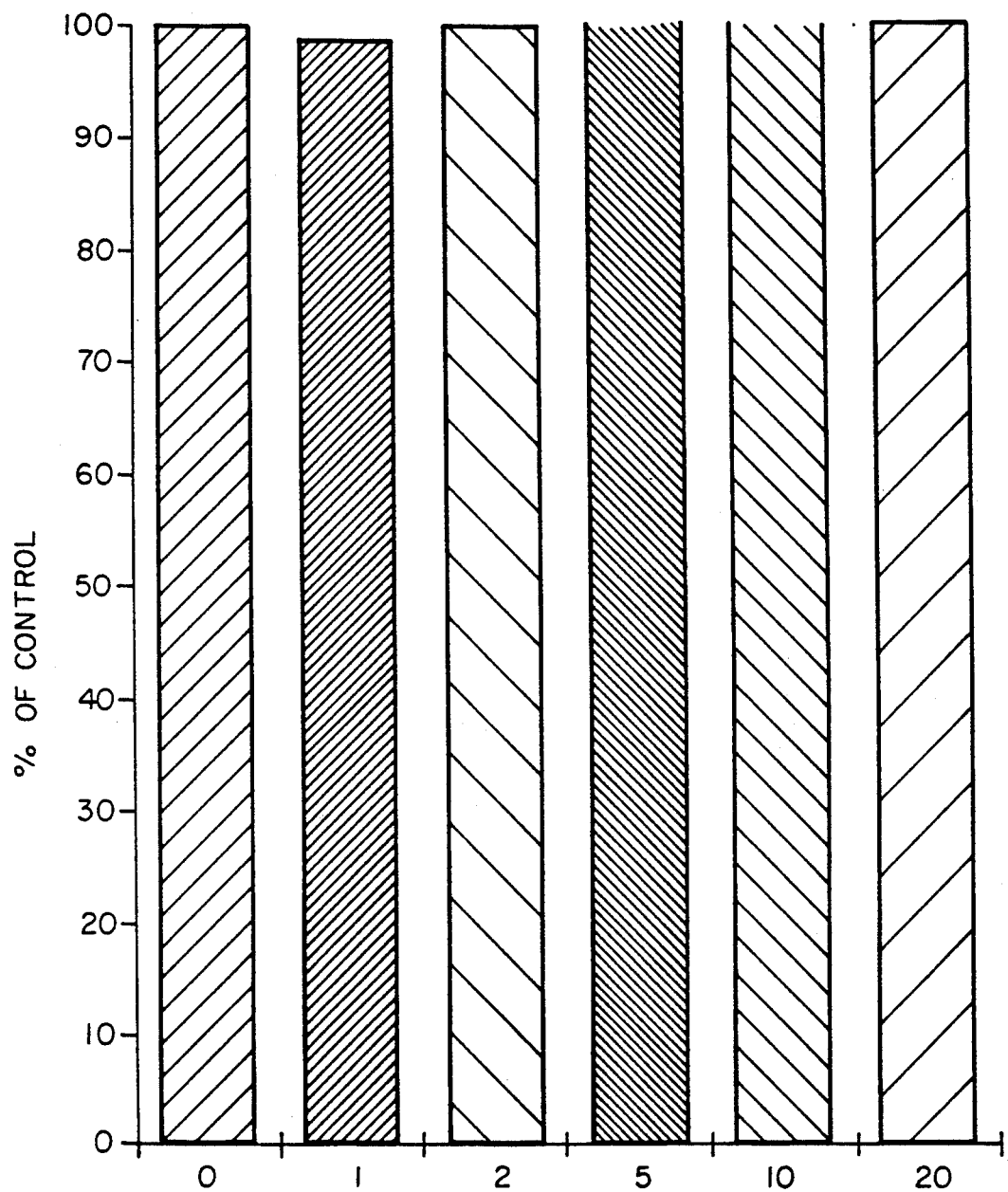
FIG. 12B is a bar graph depicting growth of MRC-5 after 24 hour exposure to 1–20 mM homocyclocreatine as a percent of the untreated control cells.

The MRC-5 lung fibroblast non-transformed cell line was treated with homocyclocreatine (0-20 mill) for up to six days to determine if homocyclocreatine also affects non-transformed cells. Cells were grown attached to plates, and were treated in a similar fashion to the DU 145 cells. $^3$H-thymidine was added to the cells one hour before harvesting. As can be seen in FIGS. 12A and 12B, there was little effect of homocyclocreatine on the DNA synthesis of the non-transformed cell line, even in the presence of 20 mM homocyclocreatine. In FIG. 12A, for a 6 day exposure to drug, the radioactivity incorporated in the presence of drug, up to 20 mM, is similar to the radioactivity incorporated in the absence of drug. FIG. 12B shows growth as a percent of control in bar graph form for cells exposed to drug for 24 hours. Again, even at 20 mM homocyclocreatine, there was no effect on growth of the non-transformed cell line. These results suggest that normal tissues may not be adversely affected by homocyclocreatine, and that the specificity of the drug for tumor tissue may be high.

Effect of Homocyclocreatine on Other Prostate Tumor Cell Lines

Figure 13A:
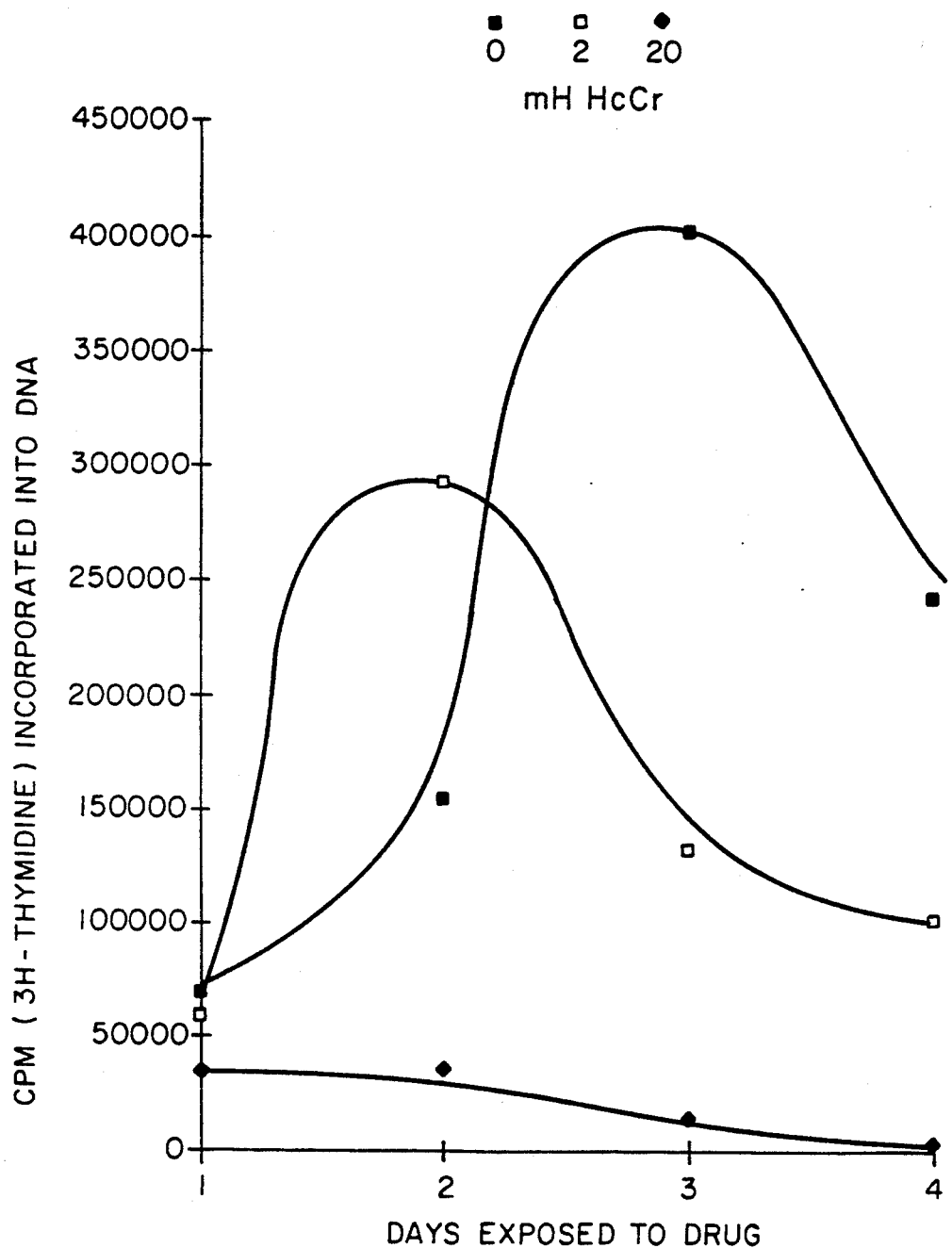
FIG. 13A is a graph depicting effects of 0, 2, and 20 mM homocyclocreatine on growth of DU 145 prostate tumor cell ine.
Figure 13B:
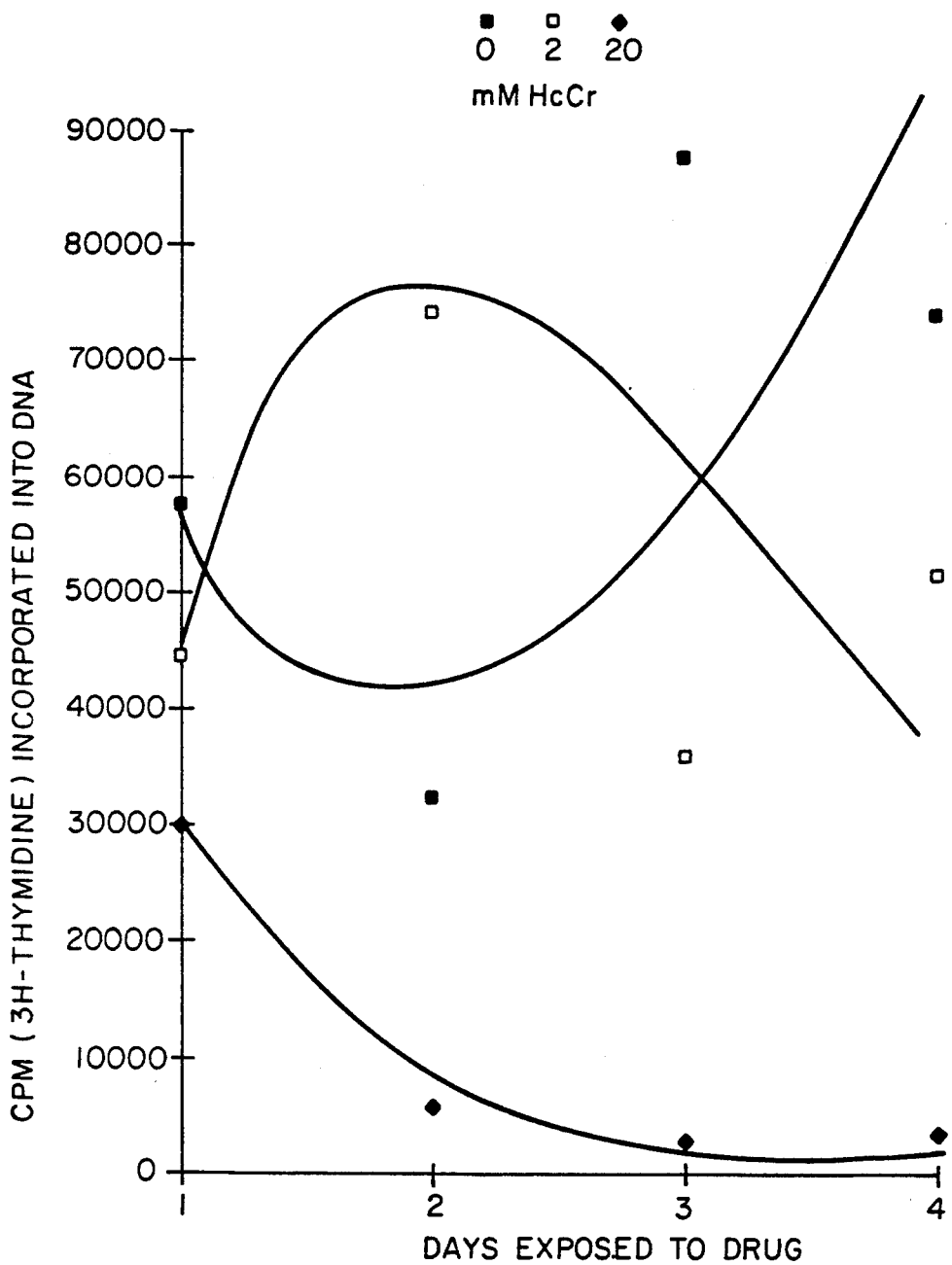
FIG. 13B is a graph depicting effects of 0, 2, and 20 mM homocyclocreatine on growth of LNCaP.FGC prostate tumor cell line.
Figure 13C:
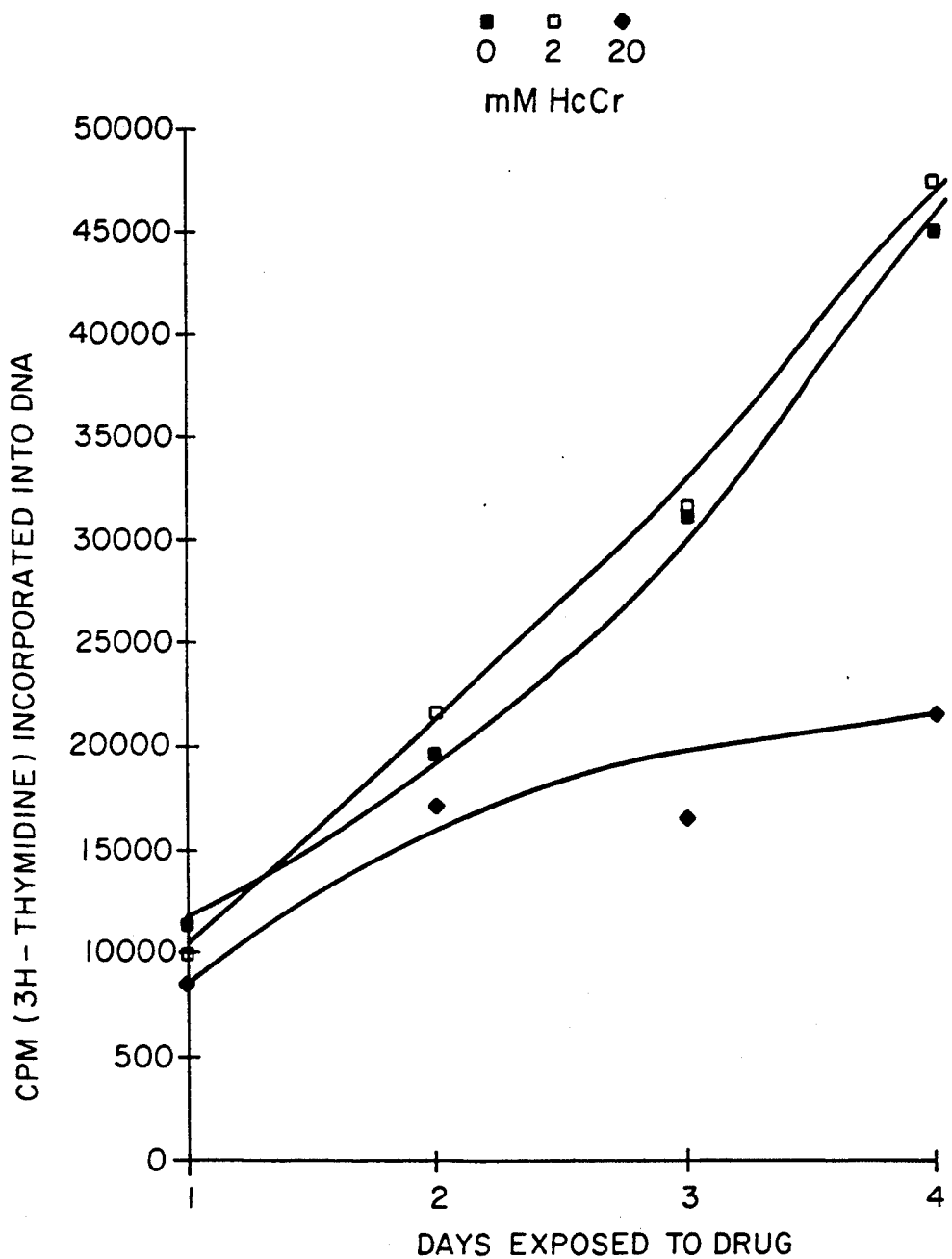
FIG. 13C is a graph depicting effects of 0, 2, and 20 mM homocyclocreatine on growth of PG-3 prostate tumorcell line.
Figure 13D:
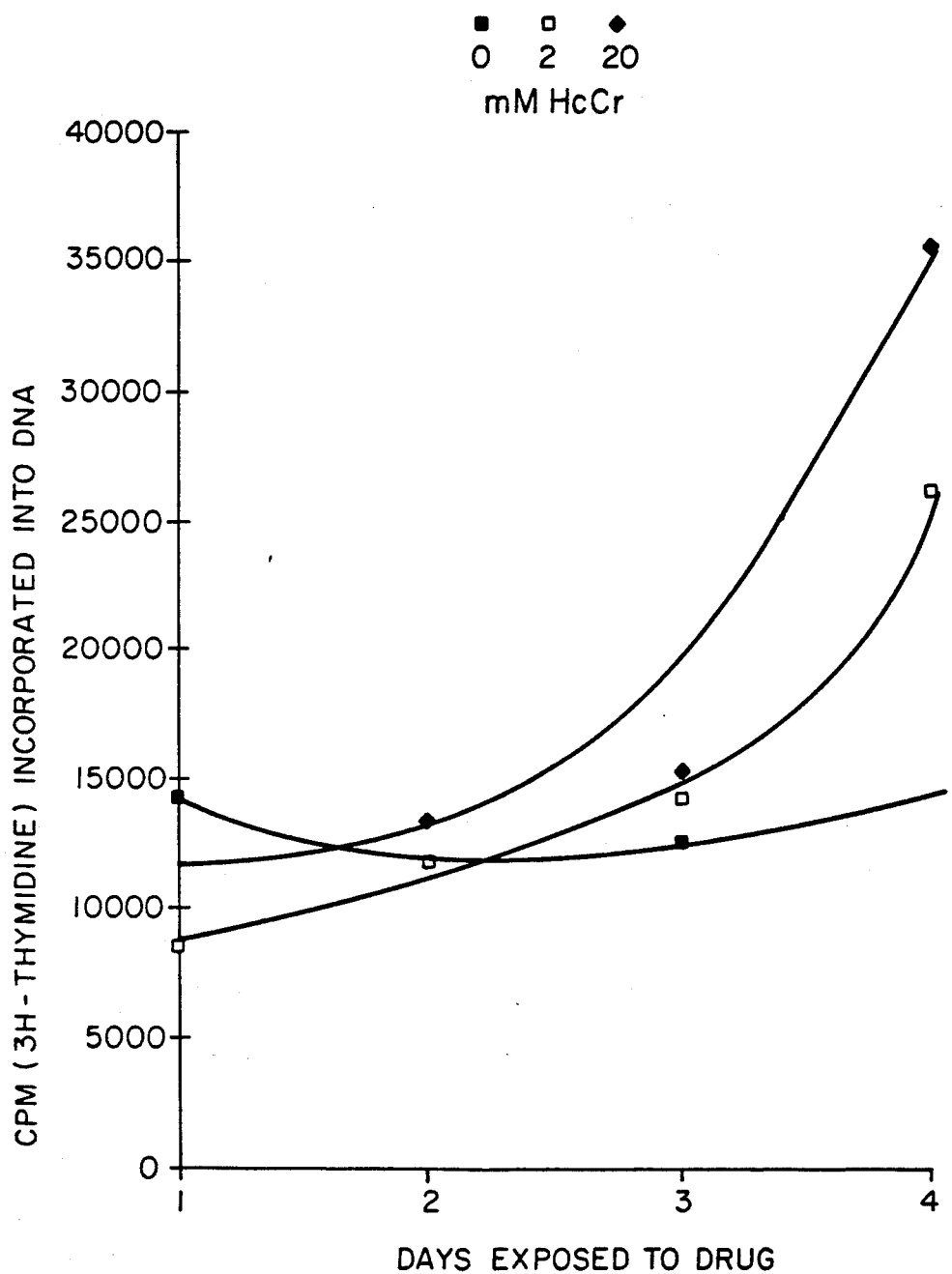

The effect of homocyclocreatine on different prostate tumor cell lines was determined. Three prostate tumor lines of different origin were analyzed, including the DU 145 cell line, derived from a brain metastasis, LNCaP.FGC, derived from a lymph node metastasis, and PC-3, derived from a prostate tumor with no evident metastasis. The cell lines were grown as described above, and were treated with 0, 2, or 20 mM homocyclocreatine. At days 1, 2, 3 and 4 after the initial exposure to the drug, cells were assayed for DNA synthesis by incorporation of $^3$H-thymidine. After one day of exposure to 20 mM homocyclocreatine, there was no additional incorporation of $^3$H-thymidine by the DU 145 cell line (FIG. 13A) or the LNCaP.FGC cell line (FIG. 13B). In contrast, after 4 days exposure to 20 mM homocyclocreatine, $^3$H-thymidine incorporation by the PC-3 cell line, which is derived from a tumor with no apparent metastasis, was only inhibited by half (FIG. 13C). The non-transformed MRC-5 cell line was analyzed in parallel (FIG. 13D). In the presence of 20 mM homocyclocreatine, MRC-5 cells showed no reduction in DNA synthesis relative to the control, confirming earlier findings (cf. FIG. 12). The inhibitory effect on tumor cell growth was more pronounced in the strongly metastatic cell lines, suggesting that homocyclocreatine may be a particularly effective treatment for late stage disease.

Effect of Homocyclocreatine on Growth of Colon Tumor Cell Lines

Figure 14A:
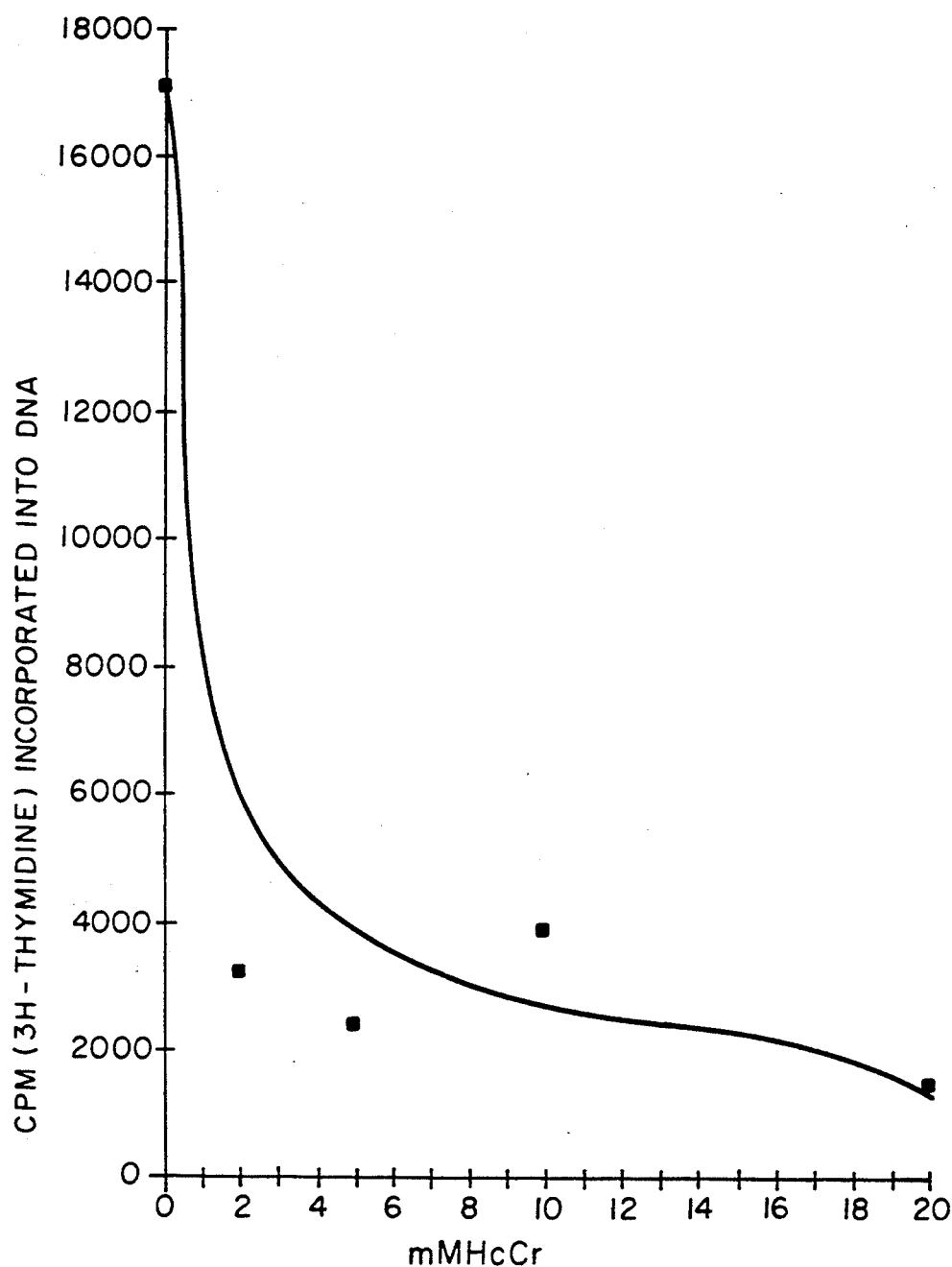
FIG. 14A is a graph depicting the effect of various cncentrations of homocyclocreatine on growth of SW1116 colon tumor cell line.
Figure 14B:
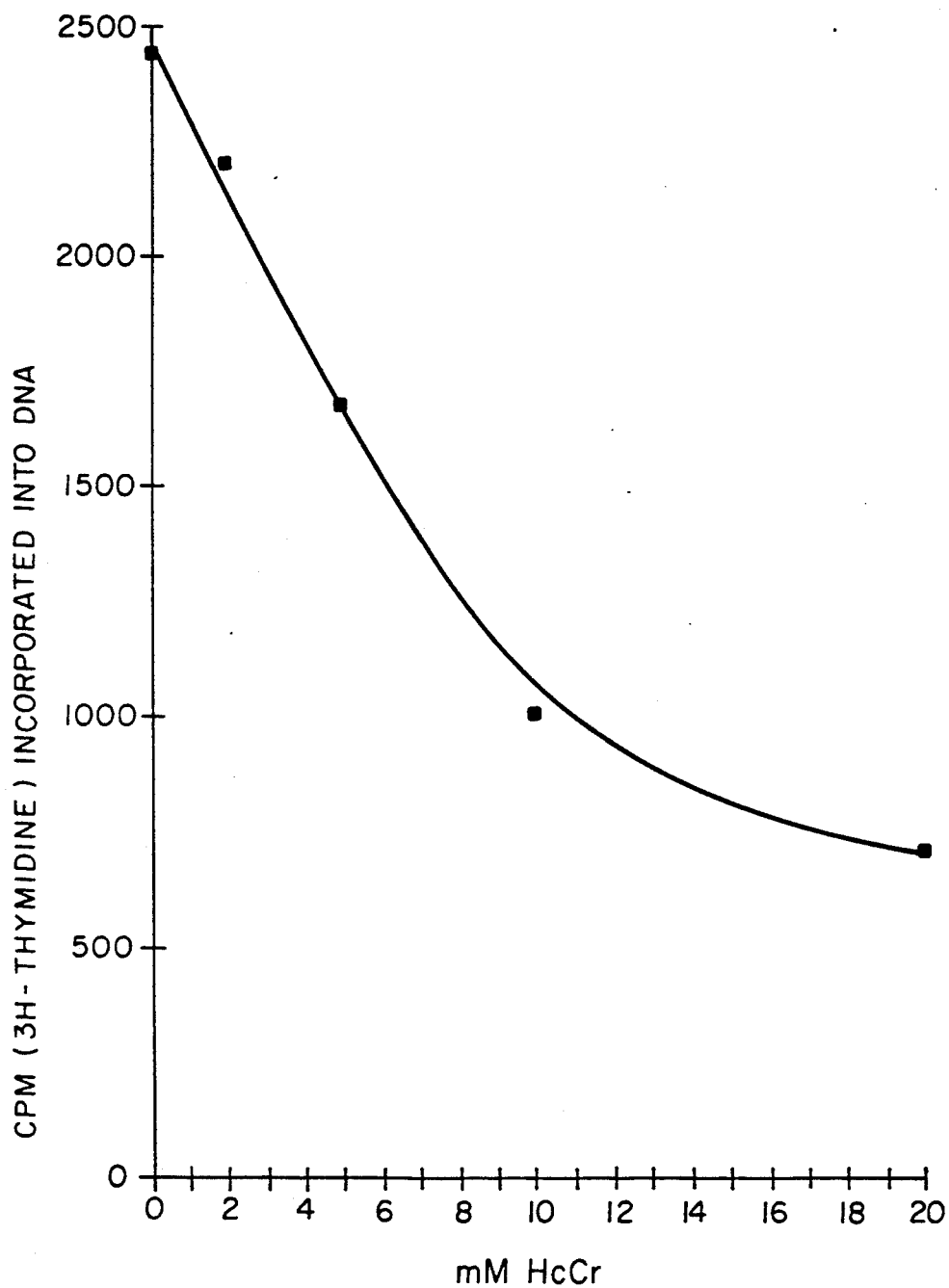
FIG. 14B is a graph depicting the effect of various concentrations of homocyclocreatine on growth of SW48 colon tumor cell line.
Figure 14C:
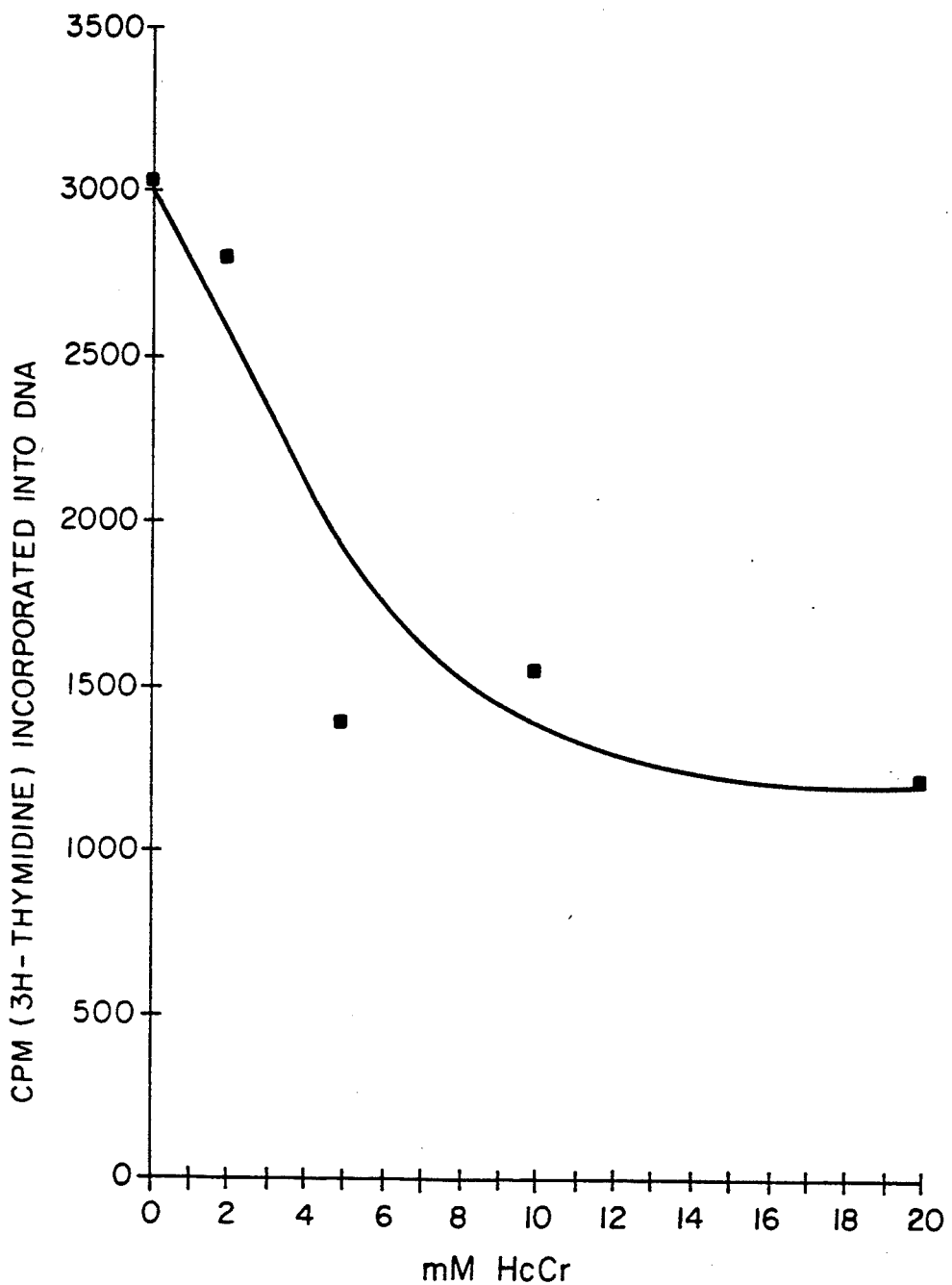
FIG. 14C is a graph depicting the effect of various concentrations of homocyclocreatine on growth of SW403 colon tumor cell line.

Three colon tumor cell lines, SW1116, SW48, and SW403 were grown in tissue culture and were tested for their response to different concentrations of homocyclocreatine. Cells were exposed to drug for 24 hours and incubated in $^3$H-thymidine for three hours. DNA synthesis was assayed by monitoring the incorporation of $^3$H-thymidine. The results of these assays for each cell line are shown in FIGS. 14 A-C, in which the incorporation of $^3$H-thymidine is plotted against the concentration of homocyclocreatine. Cell line SW1116 (FIG. 14A) showed the most dramatic effect, with almost complete inhibition of DNA synthesis at 20 mM homocyclocreatine. Prostate cell line DU 145 was treated with homocyclocreatine in parallel, and was again strongly inhibited by drug. Due to acidification of the medium, which cannot be detected under the culture conditions, these results should be interpreted with caution.

Effect of Homocyclocreatine on Growth of Cervical Tumor Cell Lines

Figure 15:
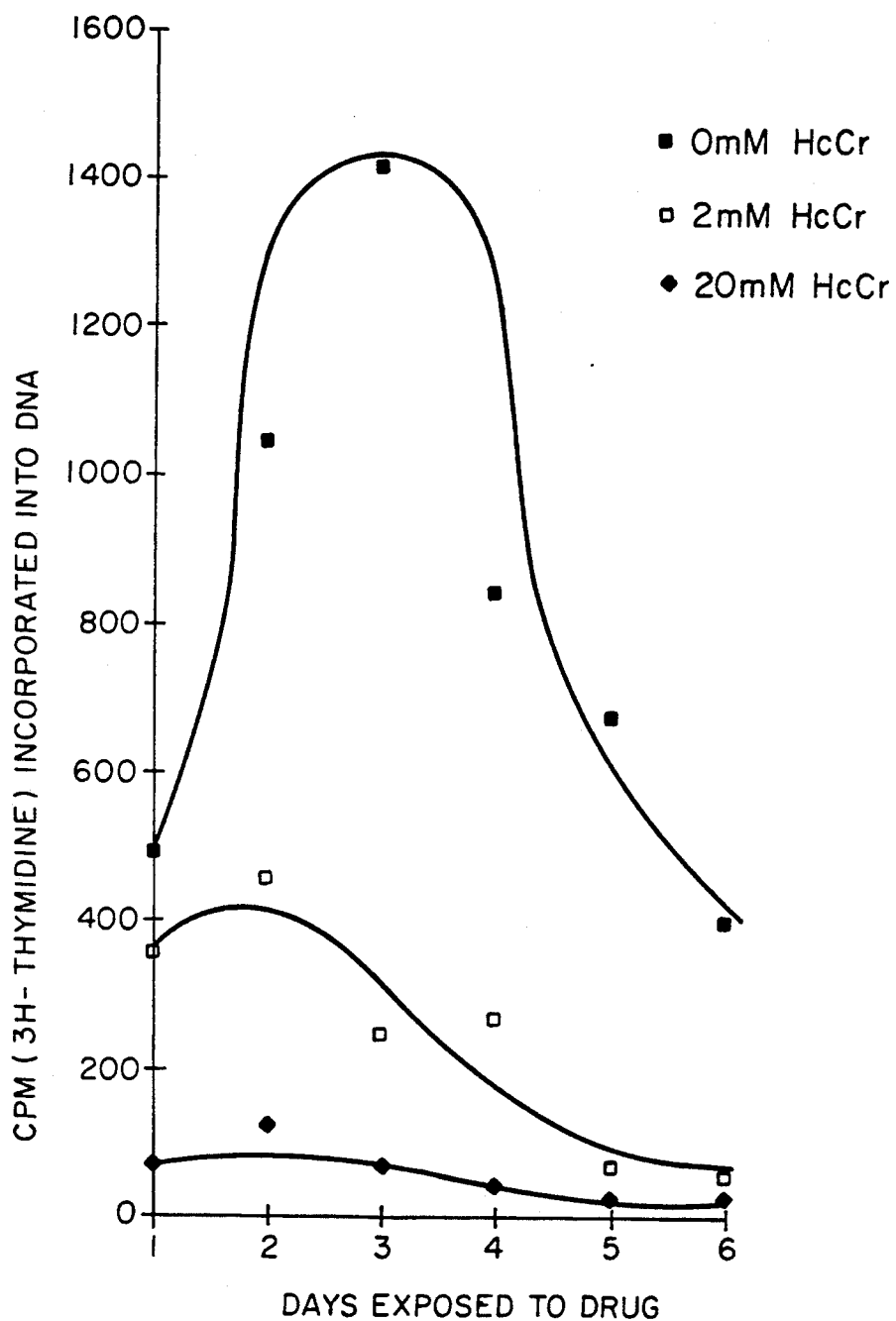
FIG. 15 is a graph depicting the effects of 0, 2, and 20 mM homocyclocreatine on growth of teh CaSki cervical tumor cell line.

The CaSki cervical tumor cell line was grown in tissue culture and tested for its response to homocyclocreatine. Cells were treated with drug and samples were collected for analysis of incorporation of $^3$H-thymidine at days 1, 2, 3, 4, 5, and 6. FIG. 15 shows that 2 mM homocyclocreatine had an inhibitory effect on DNA synthesis and that 20 mM homocyclocreatine completely inhibited DNA synthesis after 6 days of treatment, with a strong effect even after day one. Thus, homocyclocreatine appears to inhibit the growth of a variety of tumor cell types, including prostate carcinoma, colon adenocarcinoma and cervical carcinoma. The latter finding is of particular interest as sequences related to both HPV-16 and HPV-18 have been detected in the CaSki cervical carcinoma cell line (Yee, C. et al., *Am. J. Pathol.*, 119:361-366 (1985). Baker et al. reported the cloning of HPV-16 sequences from the CaSki cell line, and reported that the majority of the viral transcripts in the cell line were derived from the E6, E7 and E1 open reading frames (Baker, C. C. et al., *J. Virol.*, 61:962-971 (1987)).

EXAMPLE 3

Effect of Cyclocreatine on Tumor Cell Growth

Cyclocreatine is similar in structure to homocyclocreatine, differing only by the absence of one methylene group. The structures of both drugs are shown below.

Homocyclocreatine
(1-carboxyethyl-2-iminoimidazolidine)

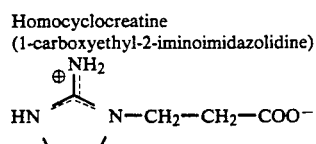

-continued

Cyclocreatine (1-carboxymethyl-2-iminoimidazolidine)

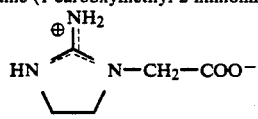

Cyclocreatine is a better substrate for creatine kinase in vitro than homocyclocreatine, and reacts 1500-fold faster. In the reverse direction, the rate of reaction with creatine kinase in vitro for cyclocreatine-phosphate (cyclocreatine-P) is about 1000-fold faster than that for homocyclocreatine-P (Roberts, J. J. and J. B. Walker, *Arch. Biochem. Biophus.*, 220:563-571 (1983)). McLaughlin et al. reported a relative maximal velocity for reaction of rabbit skeletal muscle creatine kinase with cyclocreatine that was 90% that observed with creatine, and a $K_m$ only 5-fold lower than that for creatine (McLaughlin, A. C. et al., *J. Biol. Chem.*, 247:4382-4388 (1972)). They also reported that cyclocreatine-P is a competitive inhibitor of the reverse reaction. However, in Ehrlich ascites tumor cells grown in vitro, the cyclocreatine-3-P pool was reported to be used at rates 50 to 100 times slower than the creatine-P pool (Annesley, T. M. and Walker, J. B., *J. Biol. Chem.*, 253:8120-8125 (1978). Cyclocreatine has also been reported to suppress liver amidinotransferase levels in chicks and chick embryos, suggesting the drug may inhibit the biosynthesis of creatine (Walker, J. B. and Hannan, J. K., *Biochemistry*, 15:2519-2522 (1976)).

Griffiths and Walker reported that chicks fed a diet containing 1% cyclcocreatine rapidly accumulated cyclocreatine-P in breast muscle. Heart and brain also accumulated cyclocreatine, although to a lesser extent. Chicks tolerated 1% cyclocreatine in the diet if an antibiotic (oxytetracycline) was also ingested, although these chicks grew more slowly than control chicks.

They also reported that cyclocreatine was taken up by rat muscle, heart and brain in rats fed a diet containing 1% cyclocreatine. (Griffiths, G. R. and J. B. Walker, *J. Biol. Chem.*, 251:2049-2054 (1976)) In another study, chicks were fed 1% cyclocreatine or 5% homocyclocreatine and were found to accumulate similar levels of the phosphorylated analog in muscle, brain, and heart. In contrast to homocyclocreatine-P, which was not readily used to regenerate ATP in ischemic muscle from chicks fed 5% homocyclocreatine, cyclocreatine-P was rapidly depleted in ischemic muscle from chicks fed 1% cyclocreatine (Roberts, J. J. and J. B. Walker, *Arch. Biochem. Biophys.*, 220:563-571 (1983)). Other studies have investigated the ability of cyclocreatine to sustain ATP levels or delay rigor during ischemic episodes in muscle, with the ultimate goal of enhancing the ability of tissues to withstand and recover from ischemia (Turner, D. M. and J. B. Walker, *J. Biol. Chem.*, 262:6605-6609 (1987); Annesley, T. M. and J. B. Walker, *J. Biol. Chem.*, 255:3924-3930 (1980)).

Effect of Cyclocreatine on Growth of Prostate Tumor Cell Line DU 145

Figure 16:
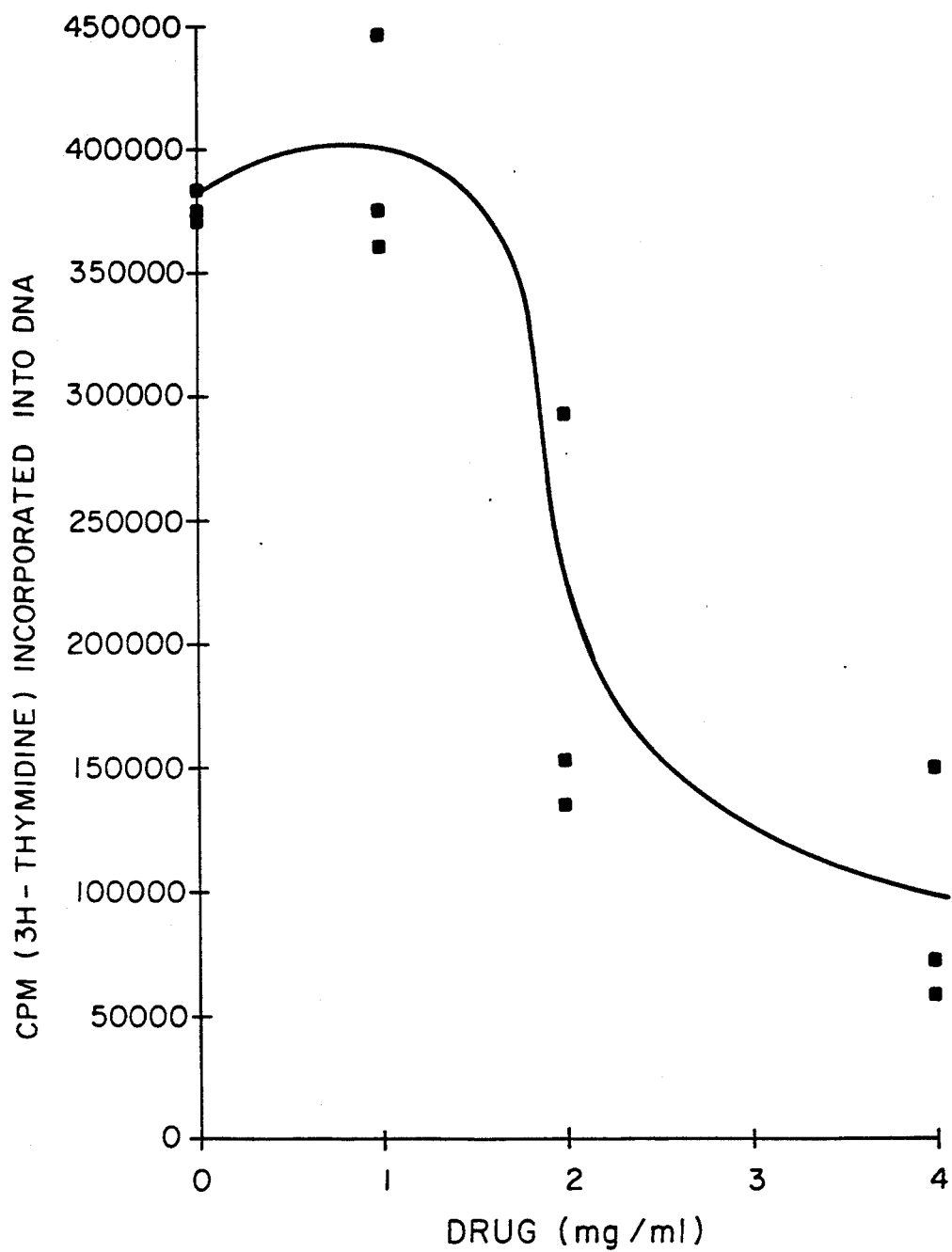
FIG. 16 is a graph depicting the effect of 0–4 mg/ml cyclocreatine on growth of prostate tumor cell line DU 145.

Prostate tumor cell line DU 145 was treated with cyclocreatine. Cells were exposed to cyclocreatine at concentrations from 1 to 4 mg/ml for 5 days, were washed to remove drug, and incubated with $^3$H-thymidine for 1 hour. DNA synthesis was monitored by incorporation of $^3$H-thymidine into DNA. Cyclocreatine strongly inhibited the growth of prostate tumor cell line DU 145 at a concentration of 4 mg/ml (FIG. 16). (4 mg/ml cyclocreatine is approximately 24 mM.)

Effect of Cyclocreatine on Colon Tumor Cell Growth

Figure 17A:
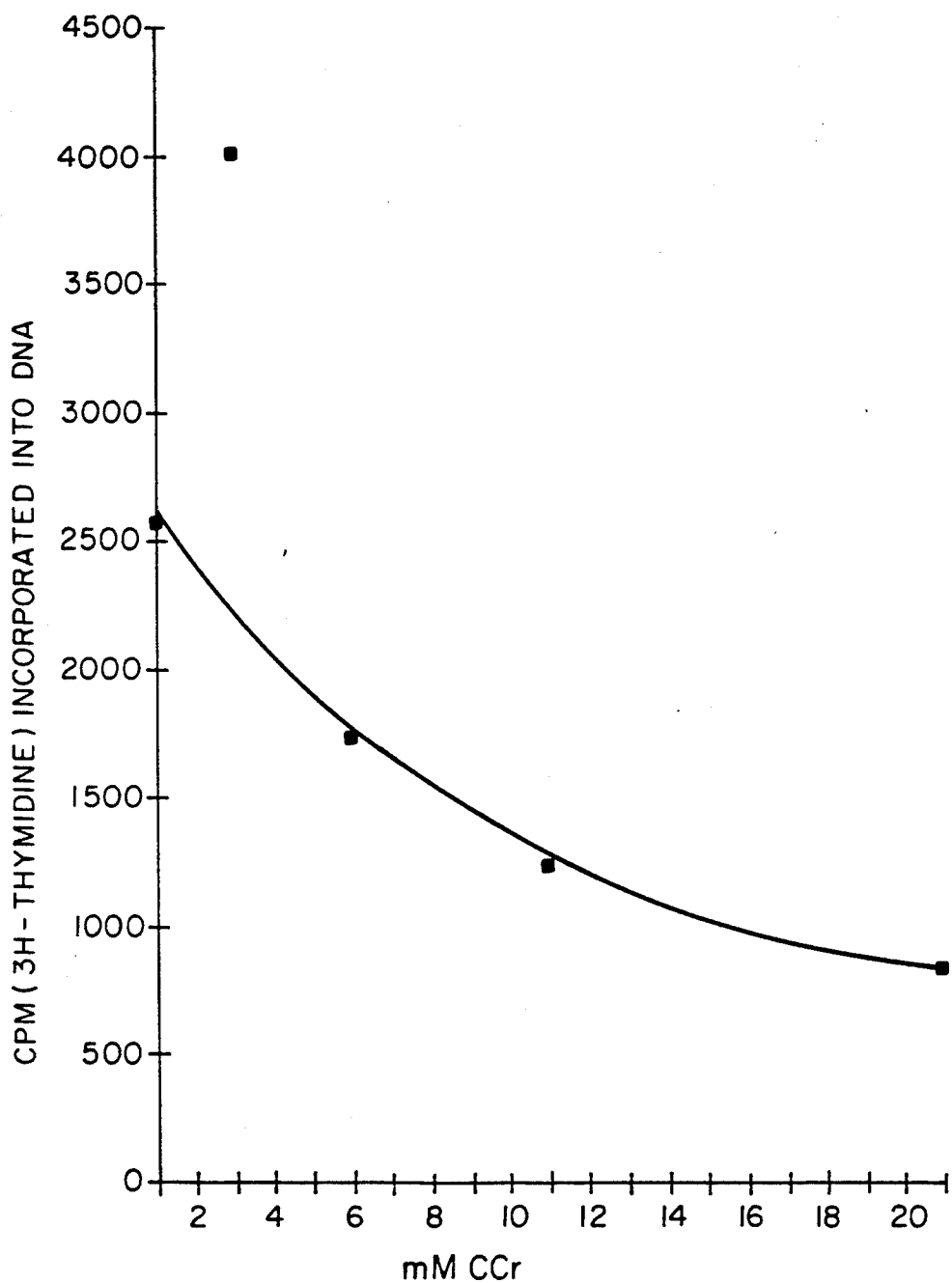
FIG. 17A is a graph depicting the effect of various concentrations of cyclocreatine on growth of SW1116 colon tumor cell line.
Figure 17B:
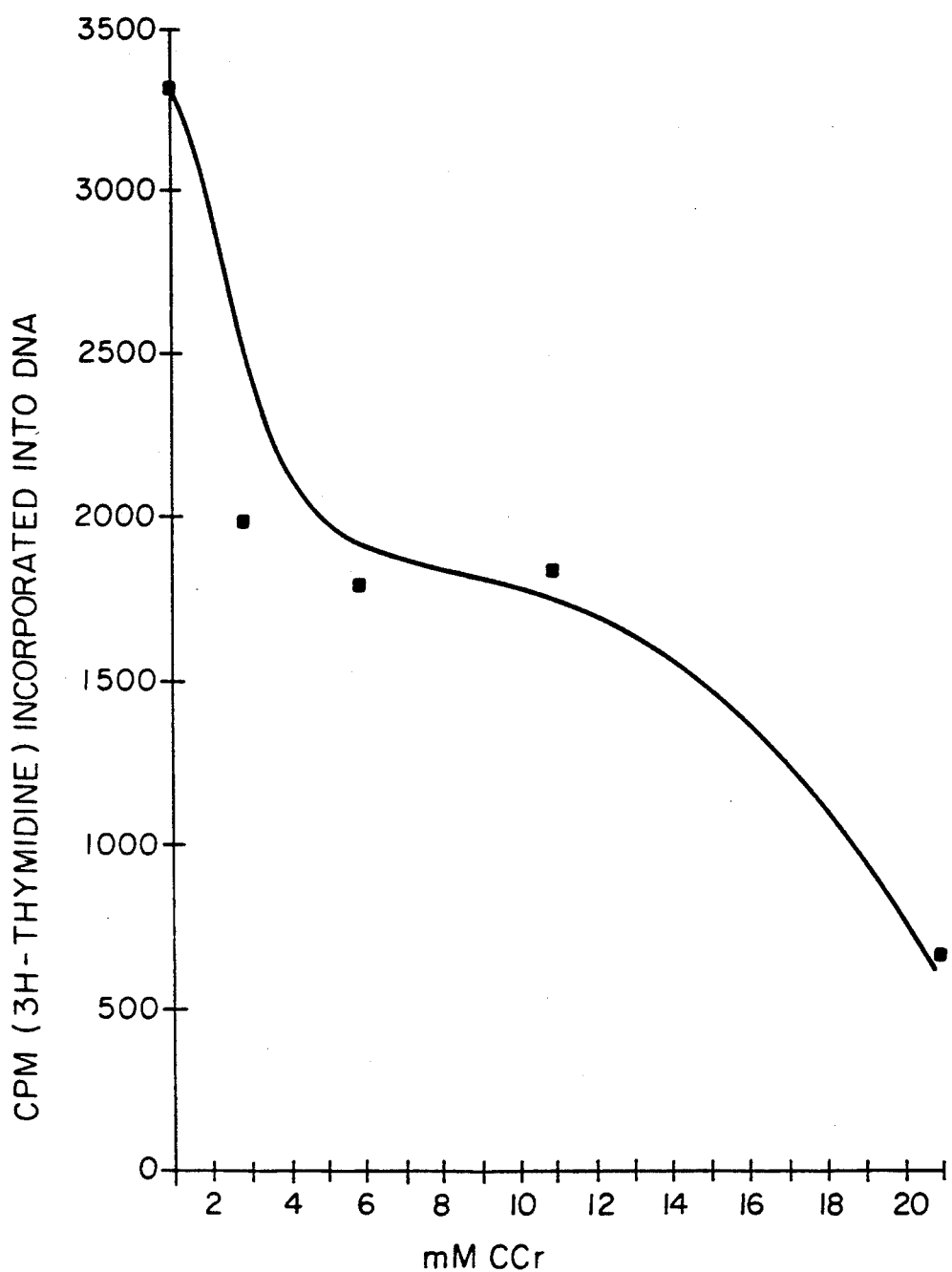
FIG. 17B is a graph depicting the effect of various concentrations of cyclocreatine on growth of SW48 colon tumor cell line.
Figure 17C:
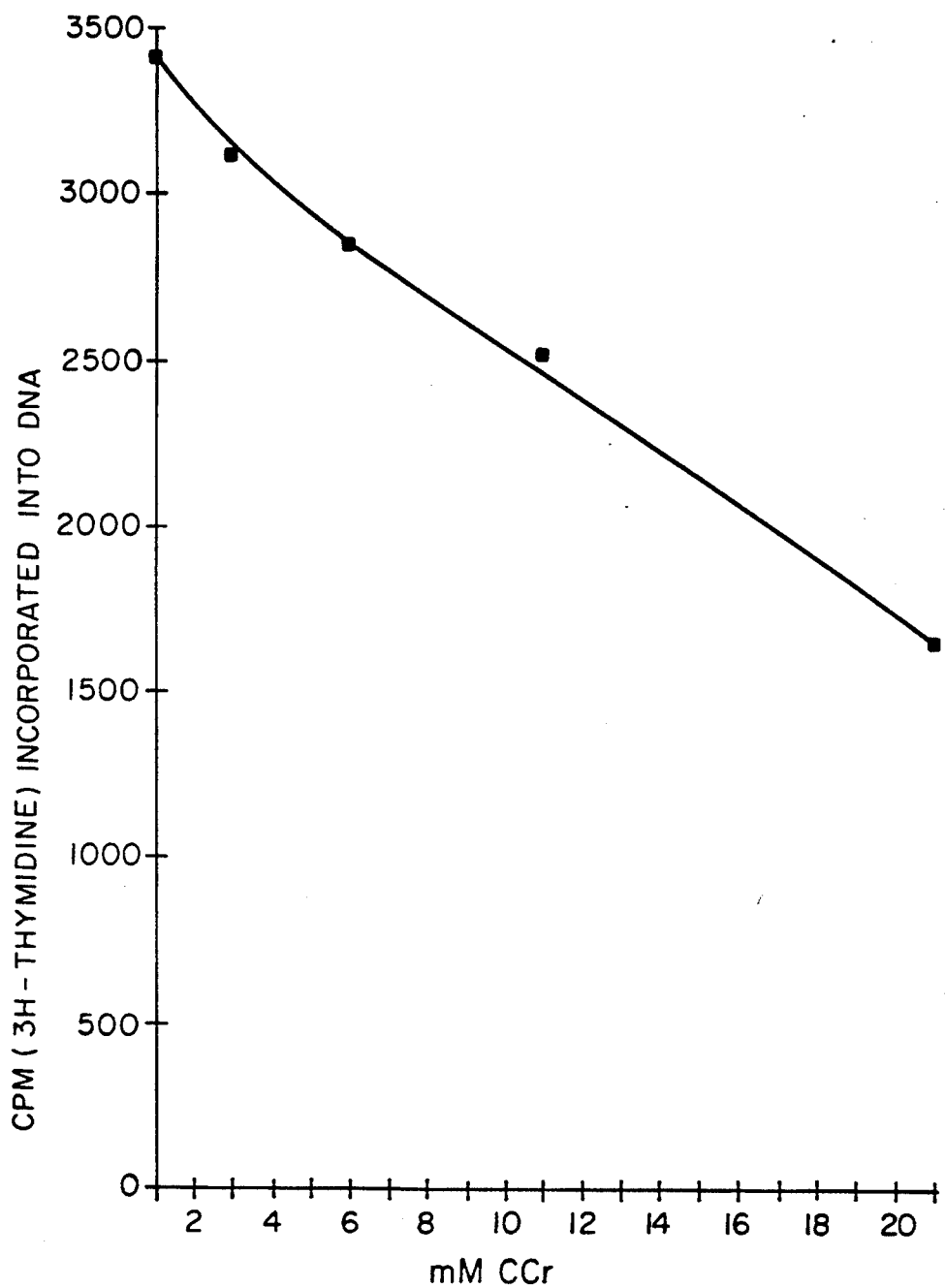
FIG. 17C is a graph depicting the effect of various concentrations of cyclocreatine on growth of SW403 colon tumor cell line.
Figure 17D:
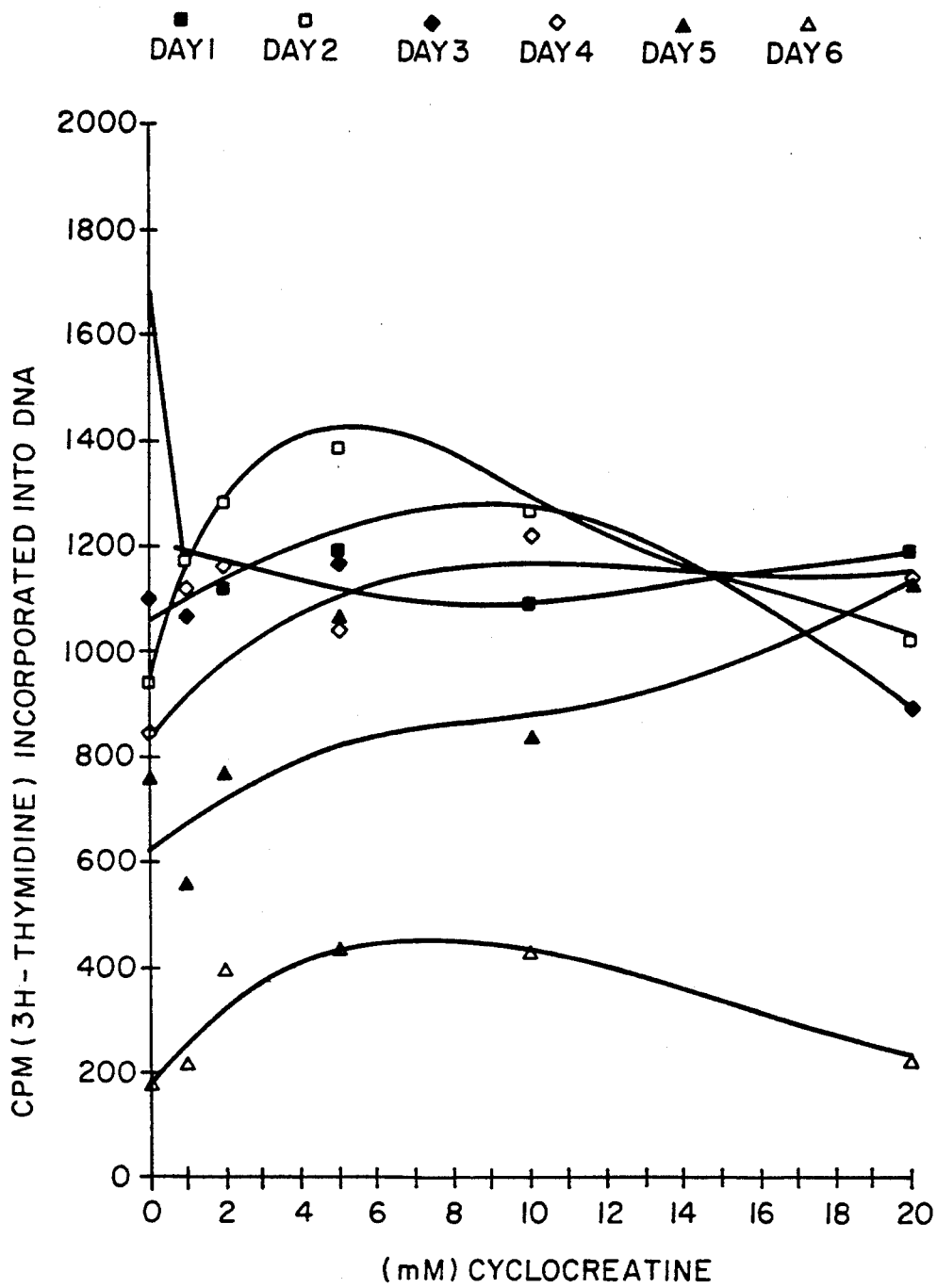
FIG. 17D is a graph depicting the effect of various concentrations of a cyclocreatine on growth of MRC-5 non-transformed cell line.

The effect of cyclocreatine on the growth of three colon tumor cell lines, SW1116, SW48, and SW403, was determined. The cells were treated with cyclocreatine (0-20 mill) using the same protocol as described for DU 145 cells. FIGS. 17A-C show that growth of the cell lines was moderately inhibited by cyclocreatine. FIG. 17D shows that, over the same concentration range, cyclocreatine did not dramatically inhibit the growth of the diploid non-transformed lung fibroblast line MRC-5, even after 6 days of exposure to drug.

EXAMPLE 4

Effect of 1-Carboxymethyl-2-iminohexahydropyrimidine On Growth of Prostate Tumor Cell Lines 1-Carboxymethyl-2-iminohexahydropyrimidine (6-CCr) is an analog of creatine, in which two of the nitrogens are joined to form a six-membered ring. 6-CCr differs from cyclocreatine in that the cyclic portion of the molecule has six members instead of five members. The structures of both drugs are shown below.

Cyclocreatine (1-carboxymethyl-2-iminoimidazolidine)

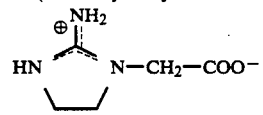

1-Carboxymethyl-2-iminohexahydropyrimidine (6-CCr)

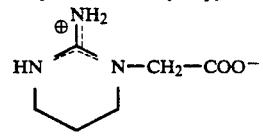

The initial rate of reaction with rabbit muscle creatine kinase of 6-CCr was reported to be 400 times slower than the initial rate of reaction of cyclocreatine (Rowley, G. L. et al., *J. Am. Chem. Soc.*, 93:5542-5551 (1971). Another group reported no measurable activity of creatine kinase for this compound (McLaughlin, A. C. et al., *J. Biol. Chem.*, 247:4382-4388 (1972). Thus 6-CCr is phosphorylated by creatine kinase very slowly, if at all. The drug was not toxic to chick embryos or growing chicks (Griffiths, G. R. and J. B. Walker, *J. Biol. Chem.*, 251:2049-2054 (1976)).

Figure 18A:
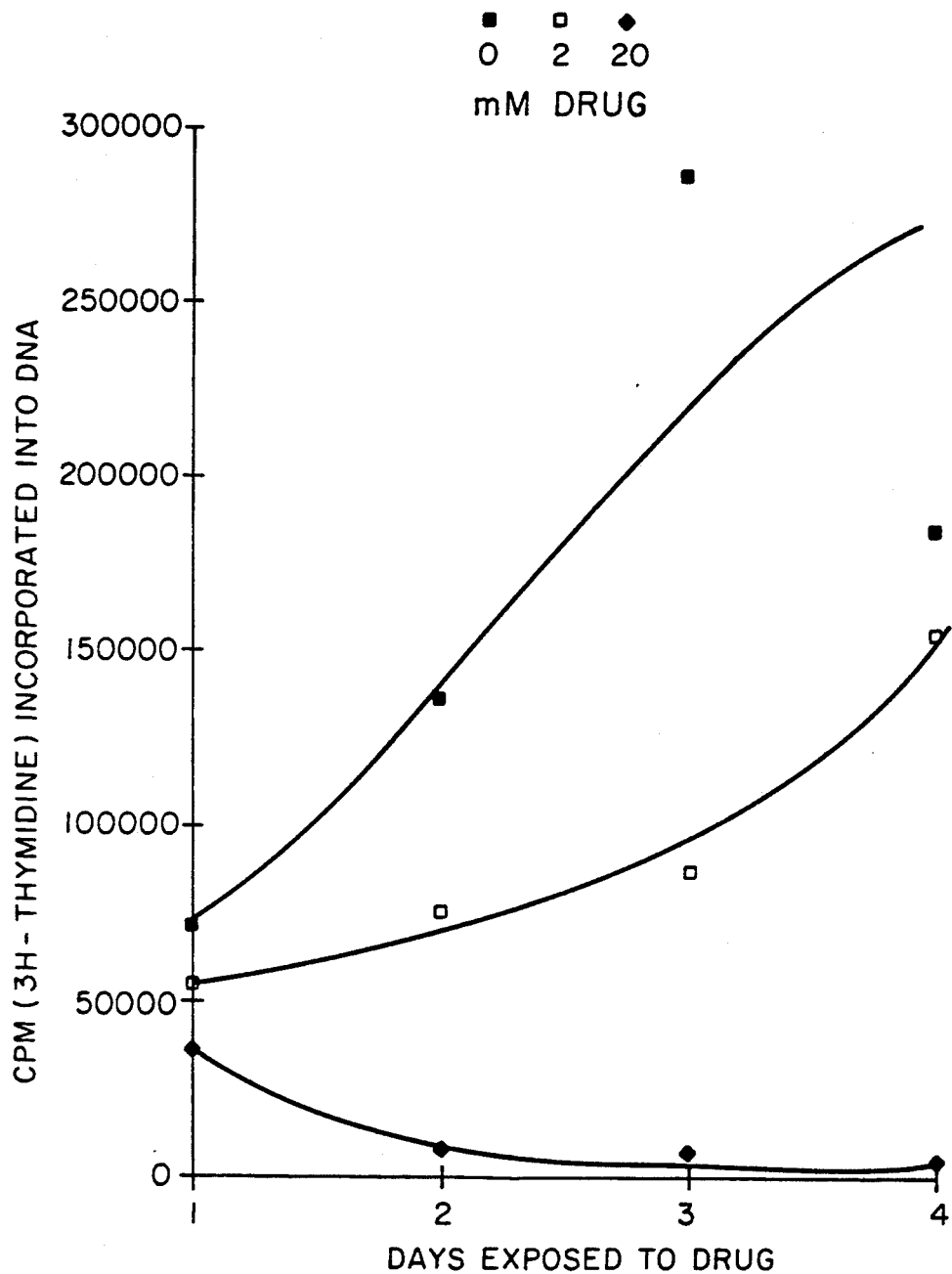
FIG. 18A is a graph depicting the effect of 0, 2, or 20 mM 1-carboxymethyl-2-iminohexahydropyrimidine (six-membered ring analog of cyclocreatein) on growth of DU 14 prostate tumor cell line.
Figure 18B:
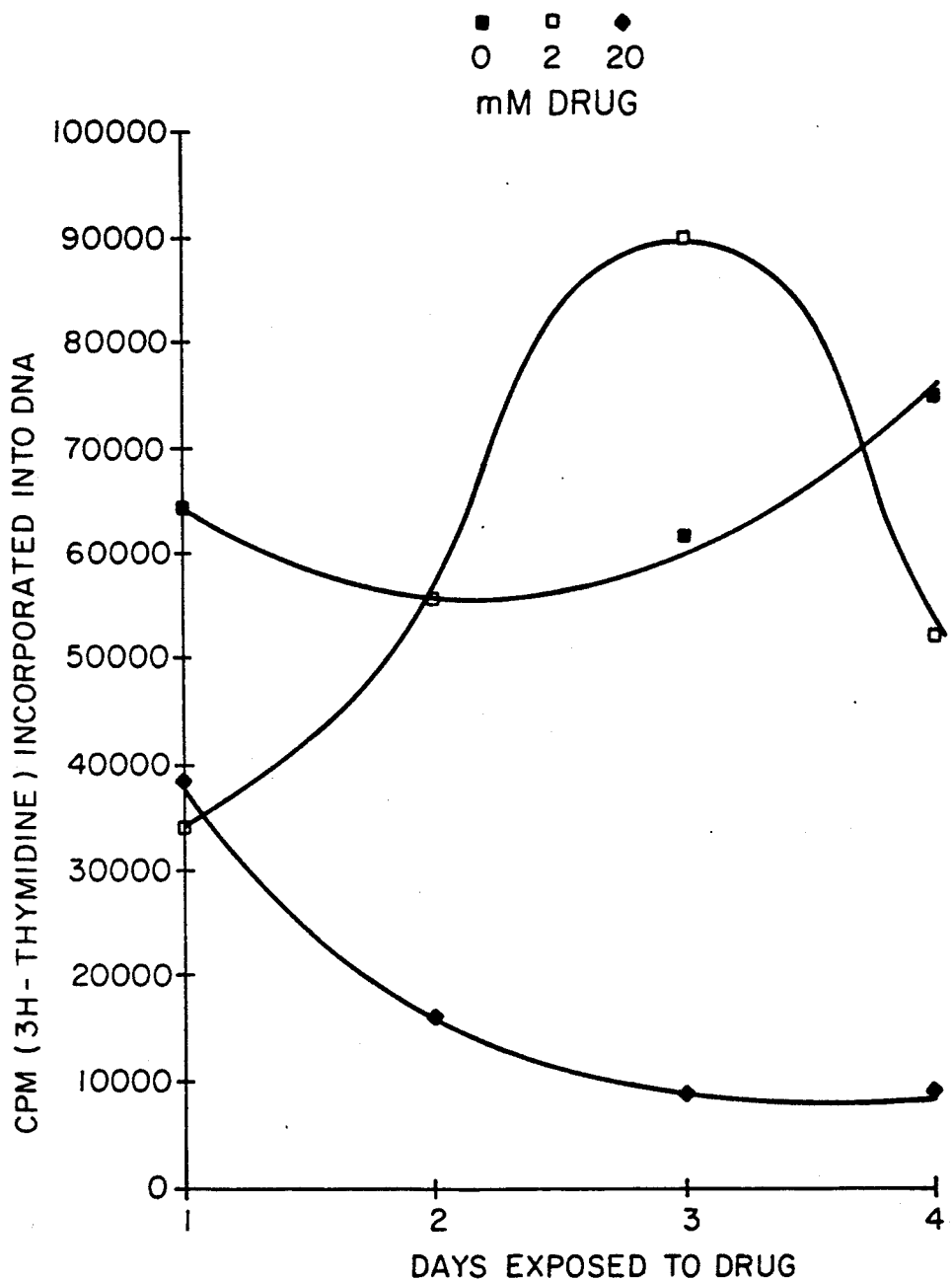
FIG. 18B is a graph depicting the effect of 0, 2, or 20 mM 1-carboxymethyl-2-iminohexahydropyrimidine (six-membered ring analog of cyclocreatine) on growth of LNCaP.FGC prostate tumor cell line.
Figure 18C:
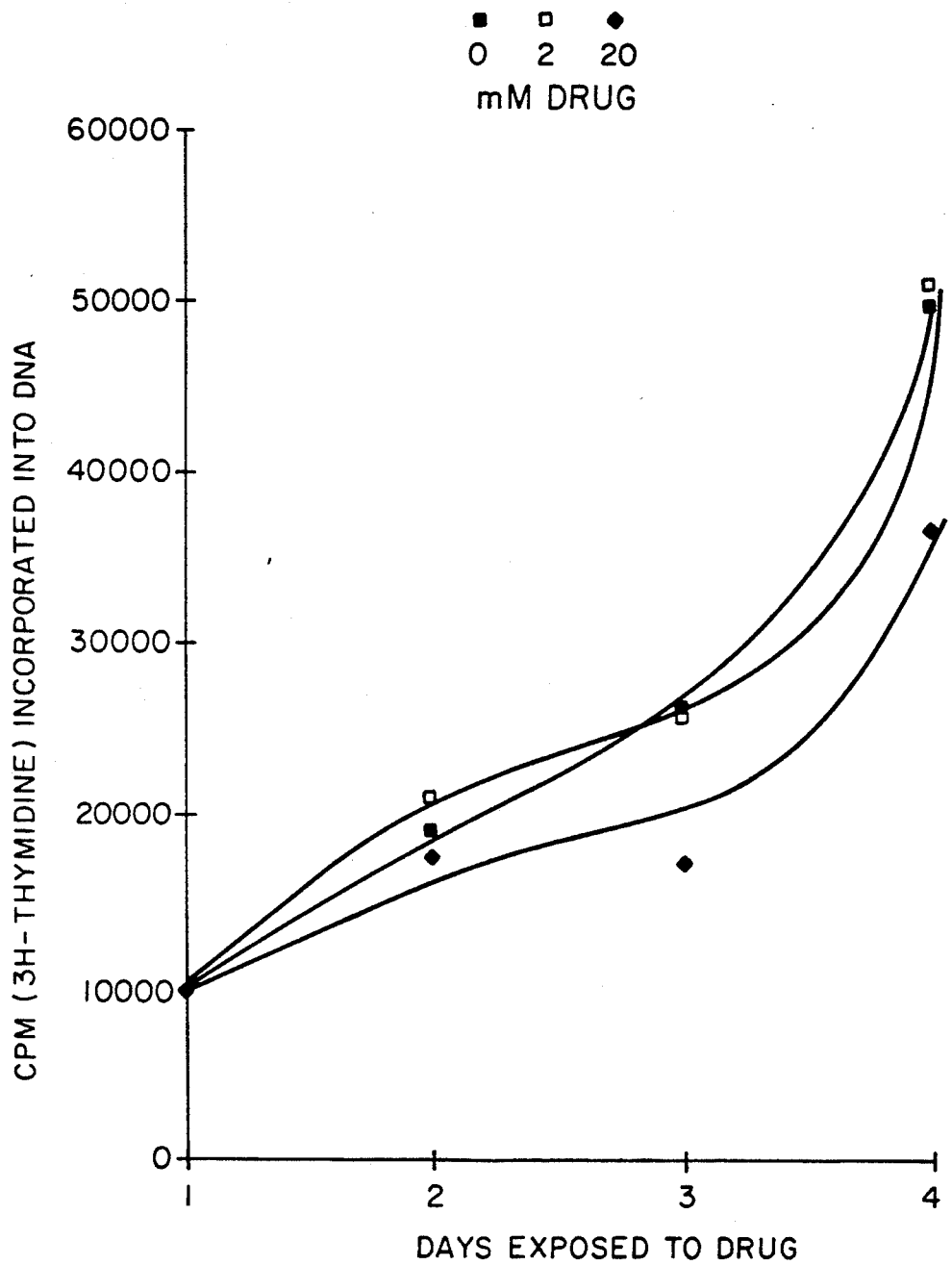
FIG. 18C is a graph depicting the effect of 0, 2, or 20 mM 1-carboxymethyl-2-iminohexahydropyrimidine (six-membered ring analog of cyclocreatine) on growth of PG-3 prostate tumor cell line.
Figure 18D:
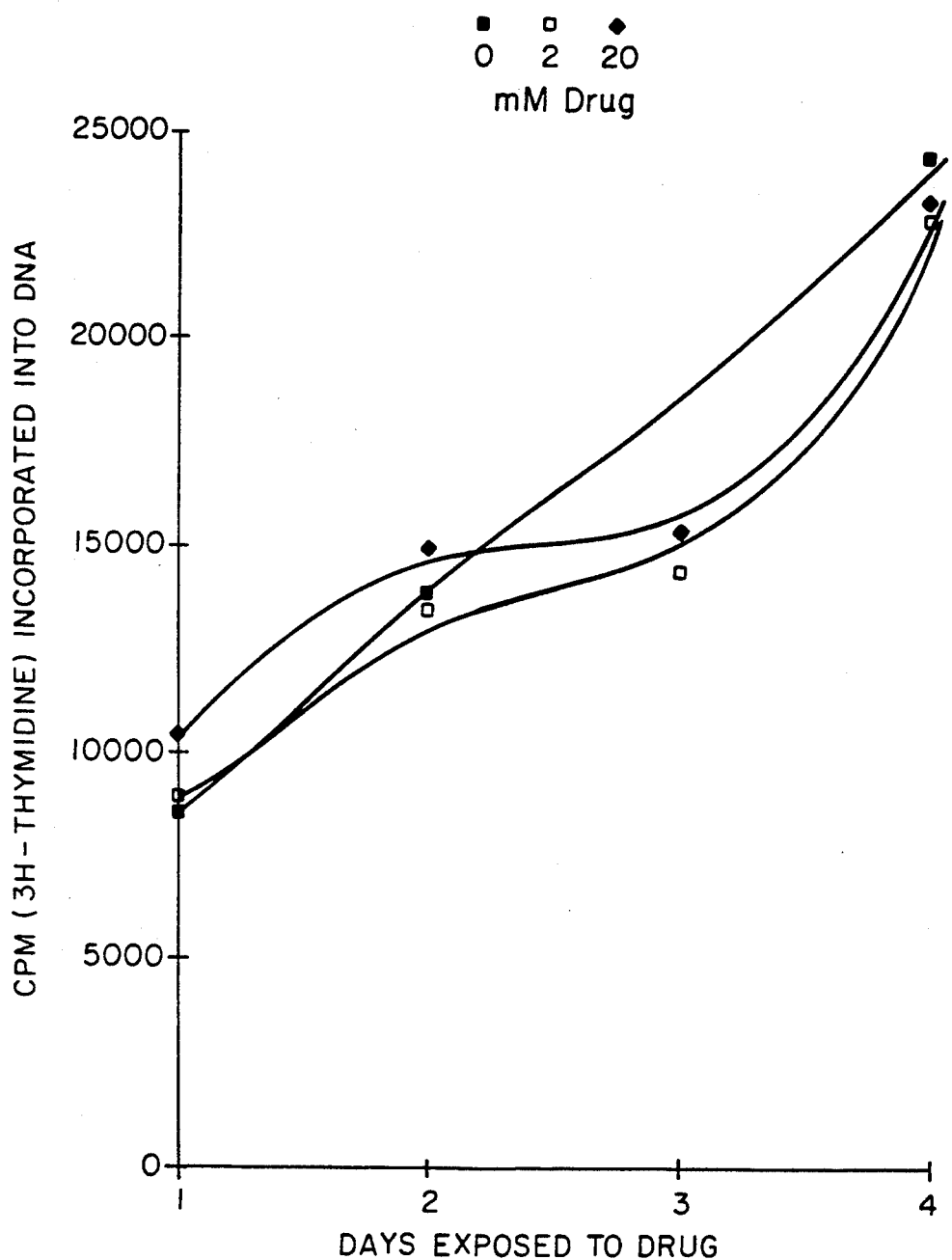
FIG. 18D is a graph depicting the effect of 0, 2, or 20 mM 1-carboxymethyl-2-iminohexahydropyrimidine (six-membered ring analog of cyclocreatine) on growth of MRC-5 non-transformed cell line.
Figure 19A:
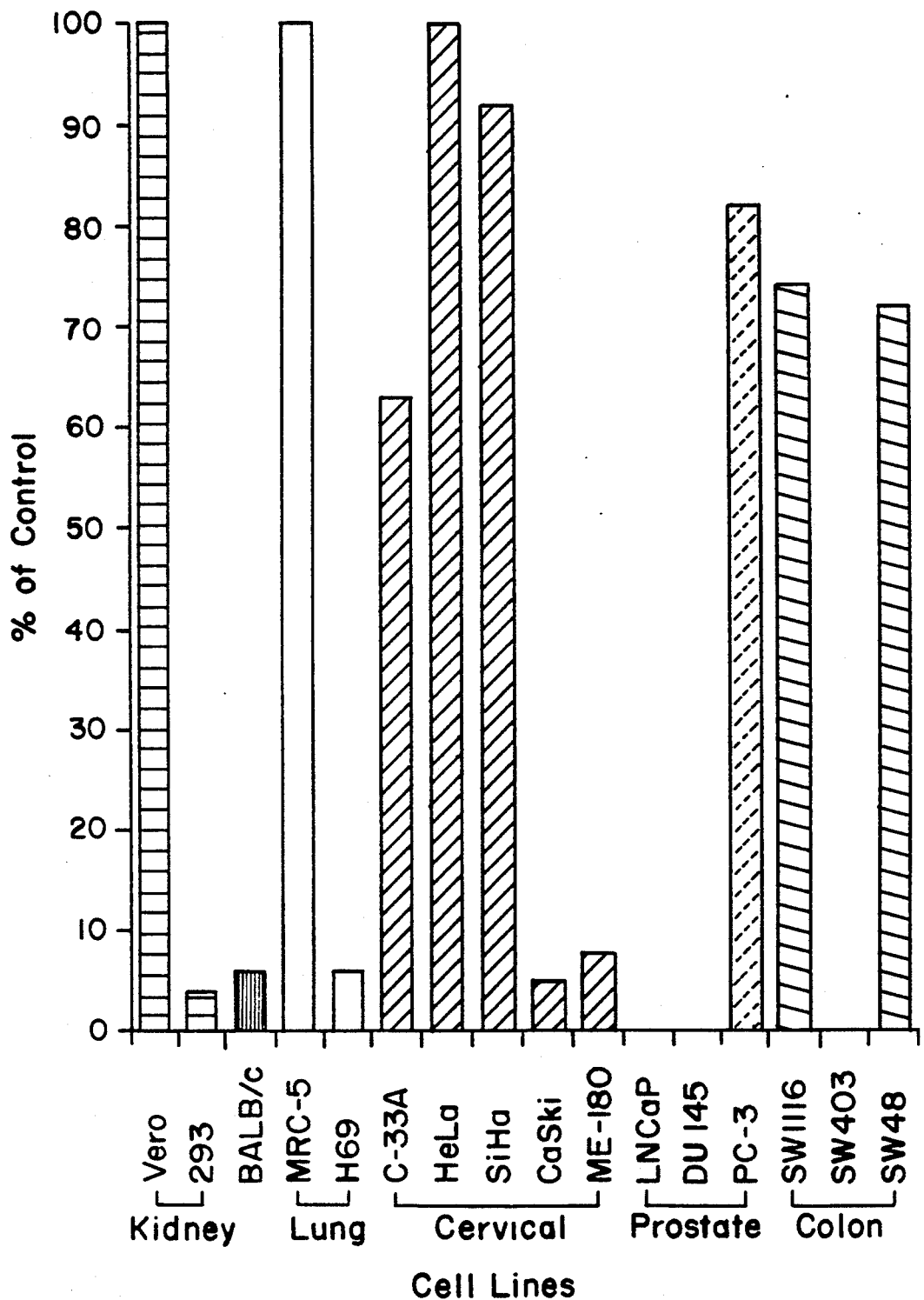
FIG. 19A is a bar graph depicting the growth of various cell lines in the presence of 4 mg/ml homocyclocreatine as a percent of the untreated control.
Figure 19A:
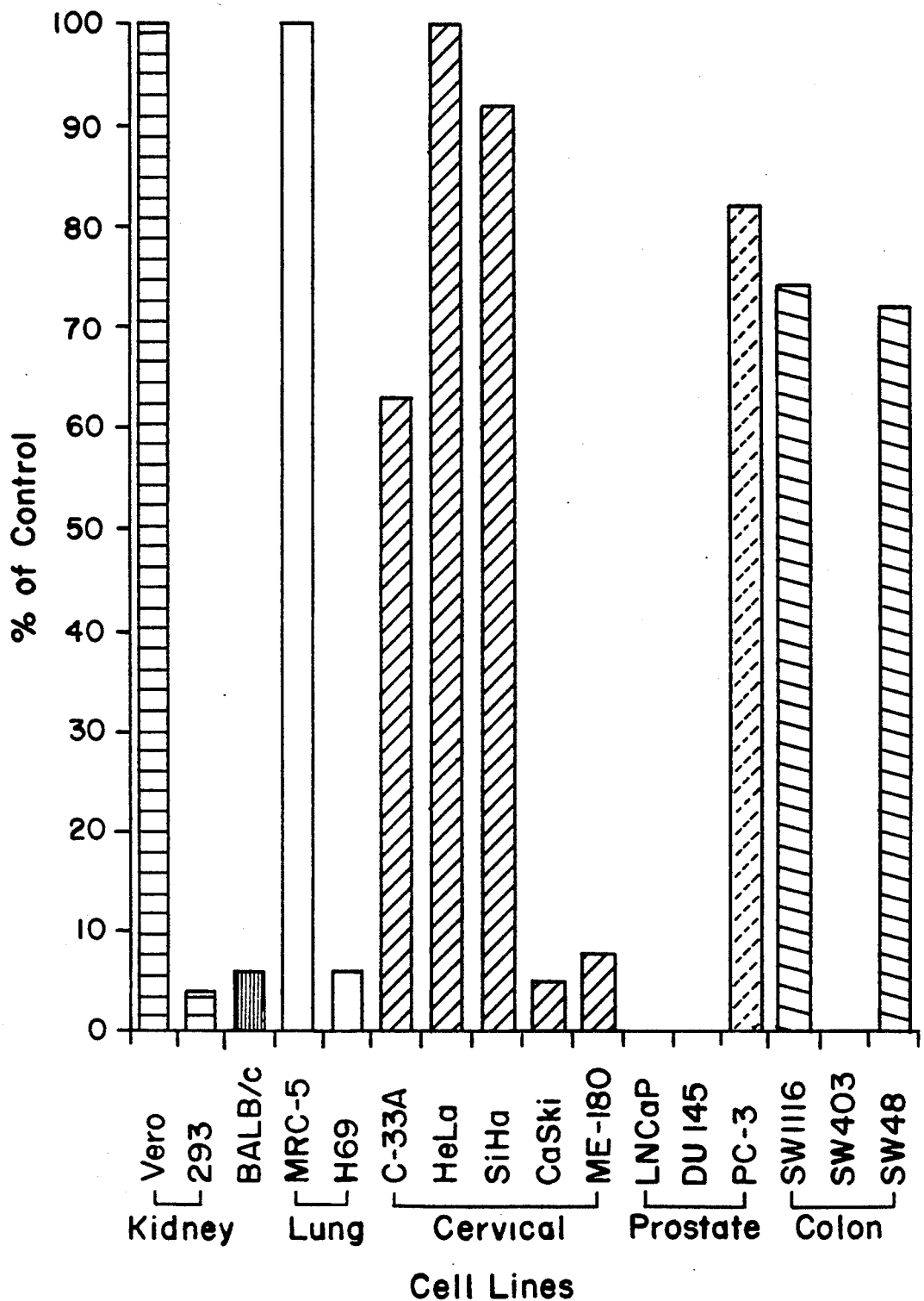
Figure 19B:
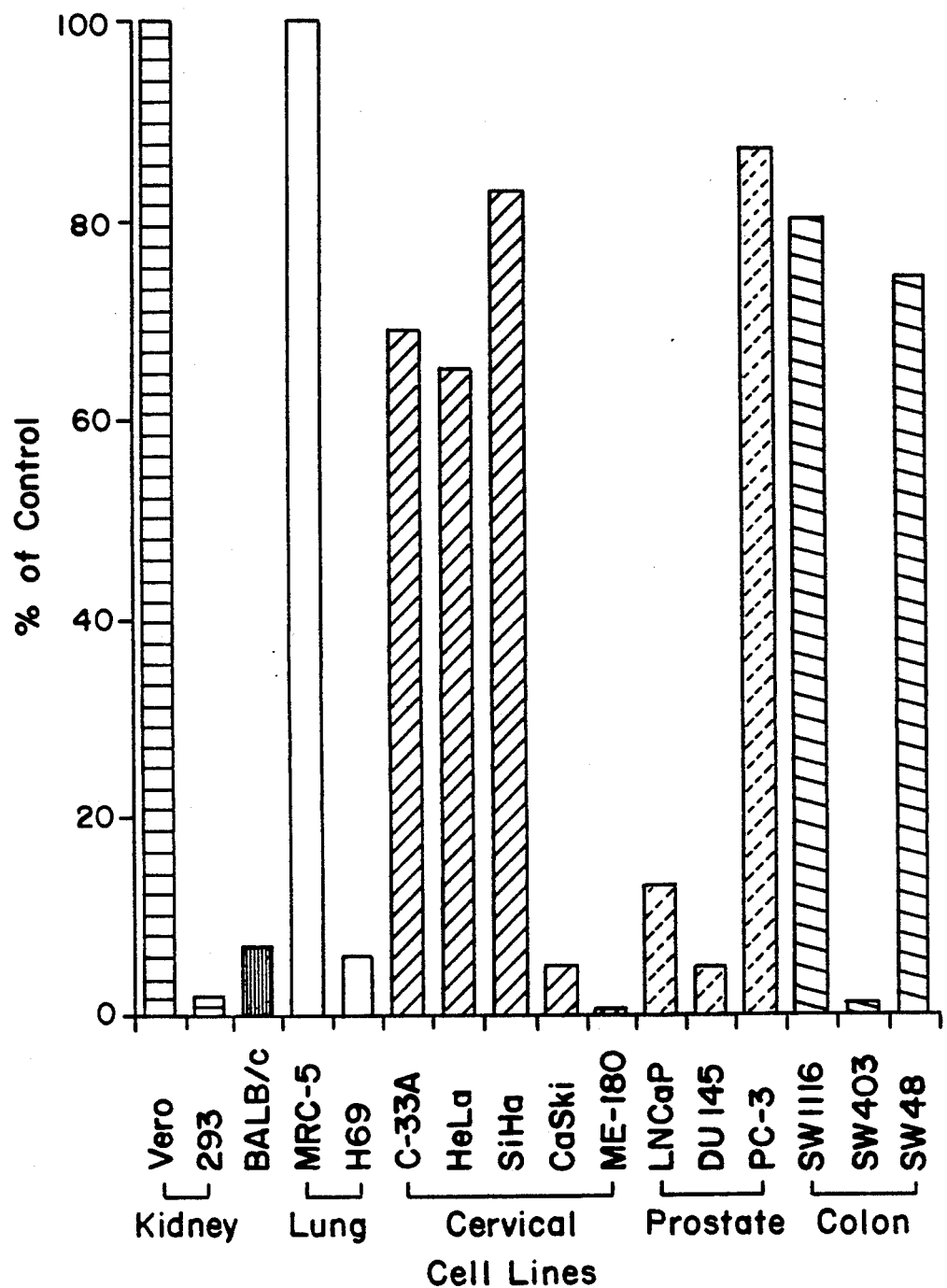
FIG. 19B is a bar graph depicting the growth of various cell lines in the presence of 4 mg/ml 1-carboxymethyl-2-iminohexahydropyrimidine as a percent of the untreated control
Figure 19C:
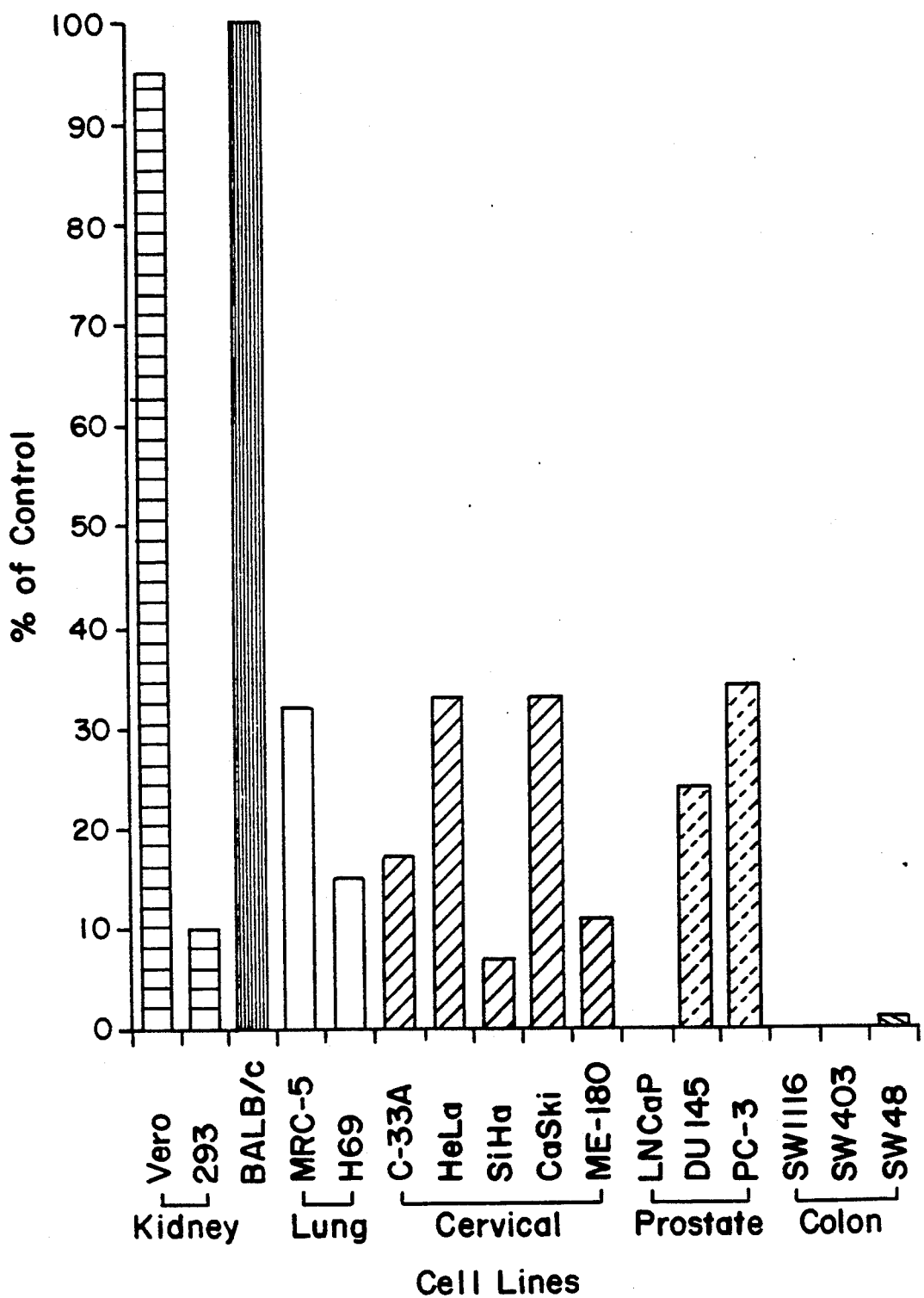
FIG. 19C is a bar graph depicting the grwoth of various cell lines in the presence of 4 mg/ml cyclocreatine as a percent of the untreated control.
Figure 19D:
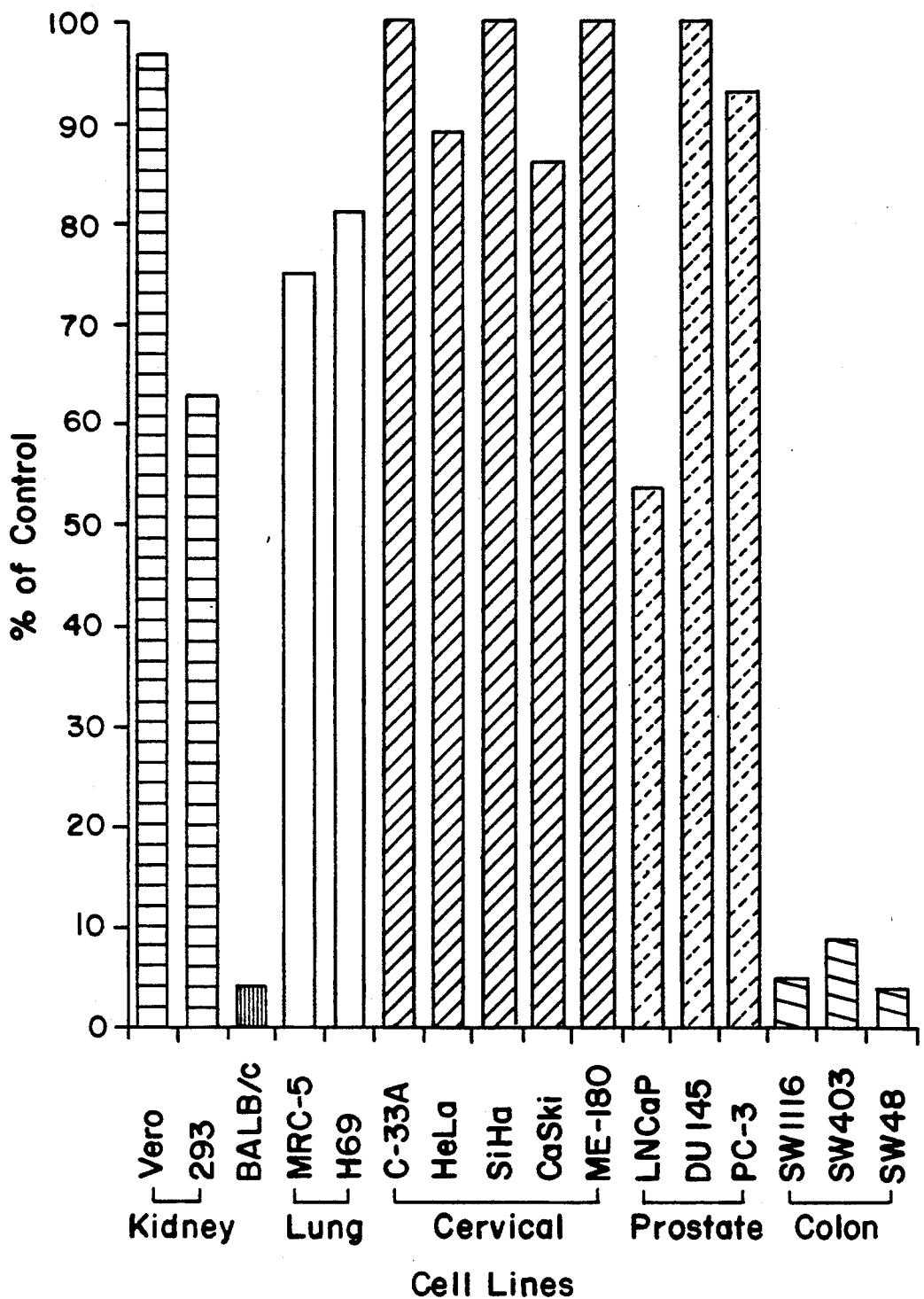
FIG. 19D is a bar graph depicting the grwoth of various cell lines in the presence of 4 mg/ml guanidinoacetate as a percent of the untreated control.

6-CCr was synthesized and tested for an effect on the growth of prostate tumor cell lines DU 145, LNCaP.FGC, and PC-3. As a control, the effect of the drug on MRC-5, a non-transformed lung embryo fibroblast cell line was tested. A strong inhibitory effect on growth of DU 145 (FIG. 18A) and LNCaP.FGC (FIG. 18B) cell lines by 20 mM 6-CCr was observed. Only a minor effect of the drug on PC-3 cells was observed (FIG. 18C), and the non-transformed MRC-5 cells were unaffected by the drug (FIG. 18D). Like homocyclocreatine, 6-CCr appears to have a stronger inhibitory effect on the metastatic cell lines, and an apparent specificity for transformed cells.

EXAMPLE 5

Comparison of the Effects of Homocyclocreatine Cyclocreatine, 1-Carboxymethyl-2-iminohexahydropyrimidine and Guanidinoacetate On Growth of Eighteen Tumor Cell Lines To confirm and extend the above analyses, eighteen different cell lines were treated with homocyclocreatine (HcCr), cyclocreatine (CCr), 1-carboxymethyl-2-iminohexahydropyrimidine (6-CCr), or guanidinoacetate (GA) in two separate experiments. Guanidinoacetate is an analog of creatine, which lacks a methyl substituent as shown below.

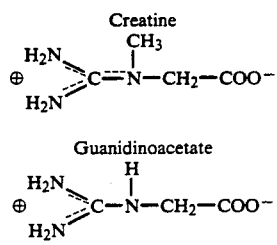

Guanidinoacetate is a biosynthetic precursor of creatine and is a moderately active substrate for creatine kinase. McLaughlin and colleagues reported a maximal velocity of reaction with rabbit muscle creatine kinase 10% that of creatine, and a $K_m$ about 14-fold below that for creatine (McLaughlin, A. C. et al., *J. Biol. Chem.*, 247:4382-4388)). Thus, while guanidinoacetate is a better substrate for the enzyme than homocyclocreatine or 6-CCr, it is a poorer substrate than cyclocreatine in the forward reaction. In addition, guanidinoacetate is reported to suppress the level of the arginine:glycine amidinotransferase in chick liver and chick embryos.

The cell lines examined in these experiments included the non-transformed lung fibroblast MRC-5 cell line, the immortal mouse embryo cell line BALB/c3T3, four human cervical carcinoma cell lines (C-33A, CaSki, SiHa, and HeLa), two human osteogenic sarcomas (U-2 OS and Saos-2), an African Green Monkey kidney cell line (Vero), an adenovirus (type 5) transformed human primary embryonal kidney call line (293), three human prostate carcinoma cell lines (PC-3, LNCAP.FGC, and DU 145), three human colon adenocarcinomas (SW1116, SW403, and SW48), a human small cell lung carcinoma cell line (NCI-H69), and the F9 mouse embryonal carcinoma cell line.

In the first set of experiments, the cell lines were treated with 0, 1, 2, or 4 mg/ml drug for five days, and were assayed for growth by incorporation of $^3$H-thymidine. In the second set of experiments, the same eighteen cell lines were treated with 4 mg/ml drug for five days before assaying for growth.

The data from both sets of experiments are summarized in Table 2. In some cases, values from a third experiment, using a similar protocol, are included in the table (in parentheses). For each of the eighteen cell lines in Table 2, the inhibition of growth by each drug at 4 mg/ml is recorded as a percent of the untreated control. (4 mg/ml 24 mM for HcCr, 6-CCr, and CCr)

TABLE 2

| Tissue | Tumor Type | (CK activity) | Cell Line | Effect of Drug on $^3$H-Thymidine Incorporation (Incorporation as a % of Untreated Control) | | | |
|---|---|---|---|---|---|---|---|
| | | | | #236 HcCr | #216 6-CCr | #229 CCr | #237 GA |
| Lung | Non-transformed (Human) | 3 | MRC-5 | 102<br>84<br>(112) | 116<br>118<br>(114) | 32<br>24 | 75<br>— |
| | Small Cell Carcinoma (Human) | 50 | NCI-H69 | 28 | 29 | 35 (1 mg/ml) | 81 |
| Cervical | Carcinoma (Human) | 10 | C-33A | 32<br>63 | 40<br>68 | 17<br>26 | 374<br>— |
| | Epidermoid Carcinoma (Human) | 0.5 | CaSki | 9<br>5<br>(4) | 25<br>5<br>(2) | 33<br>68 | 86<br>— |
| | Squamous Carcinoma (Human) | 2 | SiHa | 56<br>92 | 48<br>83 | 7<br>20 | 131<br>— |
| | Epitheloid Carcinoma (Human) | 10 | HeLa | 83<br>102 | 60<br>65 | 33<br>37 | 89<br>— |
| Bone | Osteogenic Sarcoma (Human) | 1 | U-2 OS | 101<br>0.06 | 55<br>10 | 69<br>0.02 | 147<br>— |
| | Osteogenic Sarcoma (Human) | 2 | Saos-2 | 64<br>0.03 | 825<br>27 | 7<br>0.02 | 49<br>— |
| Kidney | Normal Kidney (African Green Monkey) | 1 | Vero | 112<br>120 | 117<br>119 | —<br>79 | 97<br>— |
| | Ad 5 Transformed Embryonal (Human) | 27 | 293 | 9<br>4 | 19<br>2 | —<br>11 | 63<br>— |
| Prostate | Adenocarcinoma (Human) | 1 | PC-3 | 109<br>82 | 88<br>87 | 34<br>26 | 93<br>— |
| | Adenocarcinoma, Lymph node metastasis (Human) | 30 | LNCaP.FGC | 85<br>0.04 | 14<br>13 | 0.05<br>0.03 | 54<br>— |
| | Carcinoma, brain | | | | | | |

TABLE 2-continued

| Tissue | Tumor Type | (CK activity) | Cell Line | #236 HcCr | #216 6-CCr | #229 CCr | GA #237 |
|---|---|---|---|---|---|---|---|
| | metastasis (Human) | 15 | DU 145 | 7<br>0.03 | 12<br>5 | 24<br>0.02 | 108<br>— |
| Colon | Adenocarcinoma (Human) | 2 | SW1116 | 74<br>0.04 | 80<br>102 | 0.34<br>0.14 | 5<br>— |
| | Adenocarcinoma (Human) | 6 | SW403 | 1<br>0.47 | 91<br>0.5 | 0.12<br>0.17 | 9<br>— |
| | Adenocarcinoma (Human) | 3 | SW48 | 63<br>72 | 84<br>74 | 0.64<br>12 | 4<br>— |
| Embryonal | Embryo (Mouse) | 2 | BALB/c3T3 | 3<br>6<br>(9) | 11<br>7<br>(39) | 110<br>59 | 4<br>— |
| | Embryonal carcinoma (Mouse) | 1 | F9 | 11<br>217 | 21<br>431 | 57 (1 mg/ml)<br>7 | 204<br>— |

In some cases, the percent inhibition of growth of a cell line by a given drug appears to vary significantly. Variations in the culture conditions may explain these fluctuations. For example, in the second experiment with the Saos-2 osteogenic sarcoma line, the cells appeared to be dying independent of the administration of drug. The LNCaP.FGC prostate cells tended to grow in clumps and become nonadherent, leading to inconsistency in harvesting of the cells. Further, because healthy LNCaP.FGC cells are somewhat nonadherent, it is difficult to visually identify generally unhealthy cells and distinguish these from cells actually inhibited by drug. The F9 teratocarcinoma cells also show variation, possibly due to fluctuations in pH or to the fact that the cells are grown on a gelatin matrix and detach from the substratum easily. The incorporation of $^3$H-thymidine by the untreated F9 cells was inconsistent. Lastly, some of the fluctuation in values for the colon cell lines may result from acidification of the medium, which is not buffered by sodium bicarbonate.

The values are quite consistent in some cases. Furthermore, by conducting multiple experiments one can identify the effect of drug apart from artifactual fluctuations. For example, homocyclocreatine reproducibly inhibits the growth of DU 145. The MRC-5 cell line showed consistent values with each drug. Cyclocreatine strongly and reproducibly inhibits the growth of all three colon carcinoma cell lines (SW1116, SW403, and SW48).

A representative value from one experiment for 15 of the cell lines and an additional cell line, ME-180, derived from a cervical carcinoma, was plotted in bar graph form (FIGS. 19A–D). In these drawings, the height of the bar represents the incorporation of $^3$H-thymidine as a percent of the control for cells treated with 4 mg/ml homocyclocreatine (HcCr, 19A), cyclocreatine (CCr, 19B), 1-carboxymethyl-2iminohexahydropyrimidine (6-CCr, 19C), or guanidinoacetate (GA, 19D). The comparisons reveal several trends. First, HcCr and 6-CCr showed a nearly identical pattern of specificity, such that lines that were strongly affected by the former were strongly affected by the latter. Similarly, the lines that were marginally affected by one drug were only marginally affected by the other. In contrast, cyclocreatine showed a totally different spectrum of activity against the panel of cell lines.

The precise mode and site of action for each of these three cyclic analogs of creatine is not known. However, it is interesting to note that HcCr and 6-CCr are distinct from cyclocreatine in that they are very poor substrates for creatine kinase in the forward reaction and are phosphorylated very slowly. Also, the phosphorylated form of HcCr regenerates ATP more slowly than cyclocreatine-p in the reverse reaction. It is possible that HCCR and 6-CCr sequester a portion of the phosphate pool in the cell, or at least affect a similar cellular target.

Guanidinoacetate showed a third pattern of inhibition. In the case of guanidinoacetate, two series of experiments to date have shown strong inhibition of the growth of all three colon lines and of the BALB/c3T3 line. The remainder of the lines were largely unaffected by the drug. Again, the mode of action of guanidinoacetate is not known. However, its unique pattern of inhibition may stem from its role as a precursor of creatine. Because of the problem of maintaining proper pH of the medium under the culture conditions, data for the colon cell lines should be interpreted cautiously.

Figure 20:
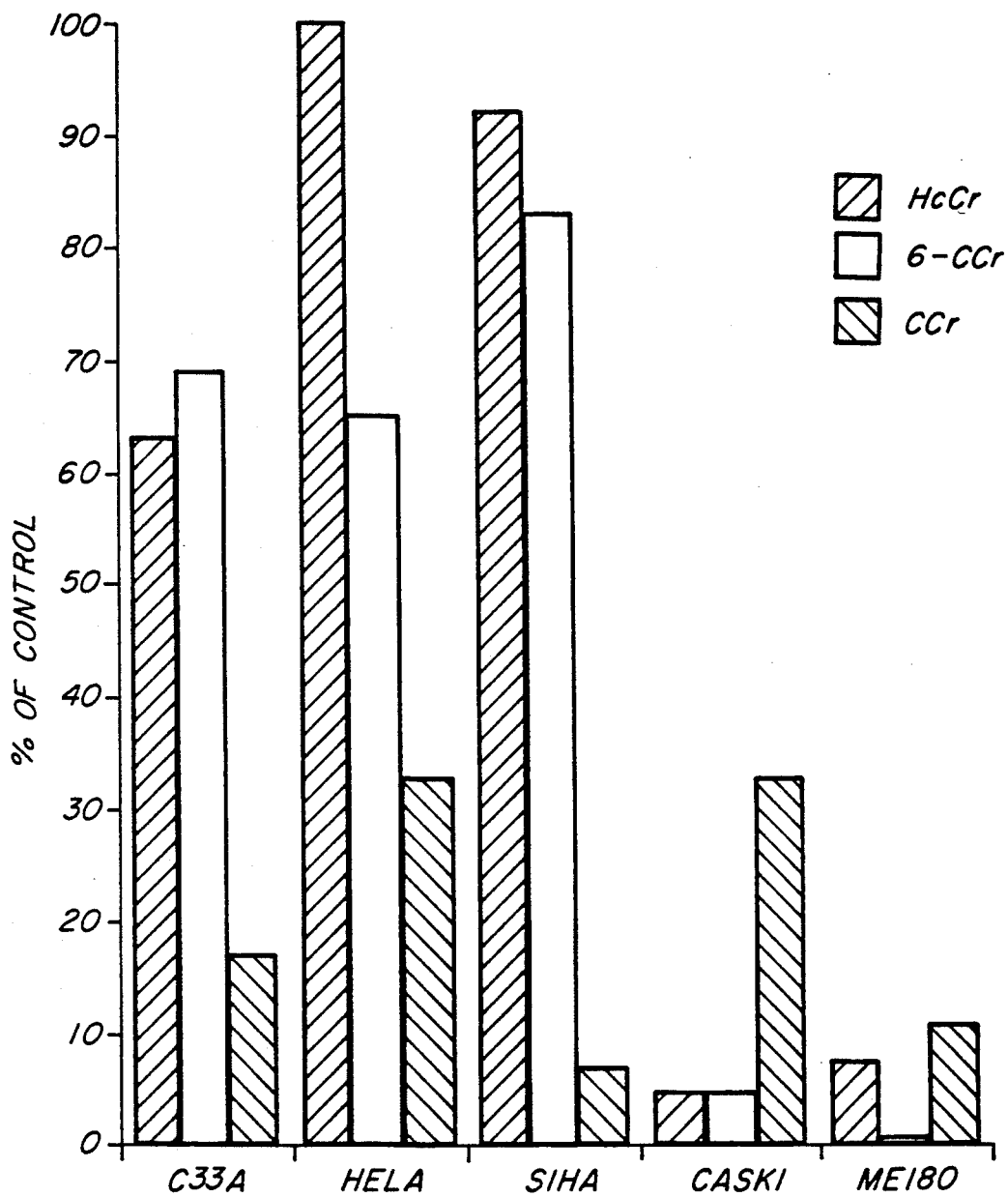
FIG. 20 is a bar graph depicting the grwoth as a percent of the untreated control for five cervical cancer cell lines grown in the presence of 4 mg/ml hmocyclocreatine, 1-carboxymethyl-2-iminhexahydropyrimidine, or cyclocreatine.

One trend is of particular interest and is emphasized in FIG. 20. FIG. 20 shows the growth as a percent of control for five cervical lines treated with HcCr, 6-CCr or CCr. The the C-33A, HeLa and SiHa lines are derived from the primary tumor, while the CaSki and ME-180 lines are derived from metastases. HcCr and 6-CCr showed a preferential inhibition of the cervical metastatic cell lines relative to the non-metastatic lines. In contrast, CCr did not show this preference for metastatic cell types. Note that HcCr and 6-CCr also tended to inhibit the growth of the metastatic prostate lines DU 145 (brain metastasis) and LNCaP.FGC (lymph node metastasis), although the results for the LNCaP.FGC line were less reproducible. Again, the non-metastatic prostate line, PC-3, was not strongly inhibited by HcCr or 6-CCr.

The metabolism of metastatic cells may differ from that of non-metastatic cells. Thus, the metastatic lines may be more susceptible to inhibition of a function that is essential, though not necessarily unique, to those cells. In addition, the function or functions inhibited in the metastatic lines may also be necessary to or involved in the process of metastasis. Conversely, HcCr and 6-CCr could be activating a suppressor of metastasis.

Recently, one identified suppressor of metastasis has been proposed to be a nucleoside diphosphate (NDP) kinase. The NDP kinases are enzymes that synthesize nucleoside triphosphates from the corresponding diphosphates, and are reported to be associated with the G proteins involved in cell signalling and with the microtubules of the mitotic spindle and cytoskeleton (Marx, J., Science, 249:482–483, 1990). Interestingly, creatine kinase has also been reported to be associated with the mitotic spindle (Eckert, B. S. et al. *J. Cell. Biol.* 86, 1–5 (1980)), and to be essential for sperm motility. HcCr and 6-CCr could be affecting the processes that control, activate, or are required for metastasis, either directly or indirectly. The drugs could be administered alone or in combination with other drugs or therapies to prevent metastasis. They may also be particularly effective in aggressive or late stage disease (especially of the prostate and cervix), where metastasis has already taken place. The DU 145 cell line does not respond to hormone therapy. Usually, late stage prostatic cancers are similarly unresponsive to hormone therapy. Thus, the drugs which inhibit growth of the DU 145 cell line, such as homocyclocreatine and 1-carboxymethyl-2-iminohexahydropyrimidine could provide effective therapies for these untreatable tumors.

Identification of the site of action of the drugs may shed light on the processes of metastasis and may suggest other methods of interfering with metastasis.

It is important to emphasize that the MRC-5 and Vero cell lines are largely unaffected by HcCr and 6-CCr. The MRC-5 and Vero lines are tissue culture versions of "normal" cell lines. Thus, HcCr and 6-CCr may also spare normal cells, suggesting they may have low toxicity in an individual.

The differences between cell lines in susceptibility to a given drug may reflect differences in the cause or severity of transformation or other properties of the cell lines, for example. The tendency of the four drugs (HcCr, 6-CCr, CCr and GA) to inhibit a particular subset of lines, in essence displaying selective killing, may also result in reduced toxicity in vivo.

It is possible that the observation that different drugs show different extents of inhibition on a single line may indicate differences in uptake, metabolism, or that multiple targets may be affected. For example, cyclocreatine and guanidinoacetate are known to inhibit the amidinotransferase involved in the biosynthesis of creatine, but cyclocreatine might affect an additional portion of the pathway. Alternatively, these differences may be a reflection of the differential effectiveness of the drugs on a single target or cellular process, such as regeneration of ATP. The drugs may also inhibit different cellular processes via a single target that has multiple functions, such as creatine kinase.

Table 3 shows the results of the same type of experiment on a subset (12) of the cell lines, using three different preparations of homocyclocreatine (#207, #235, and #236). There was some variability from preparation to preparation, however, the values for preparations #235 and #236 were very similar, despite differences in KBr in the preparations (500 parts per million in #235 and 10 parts per million in #236). Preparation #207 was an older stock which had been frozen prior to use in this assay, and appears to have lost activity as a result of this treatment. Strong inhibition of tumor cell growth was consistently observed with this preparation prior to freeze-thawing. The values for preparation #236 are also recorded in Table 2 in parentheses.

TABLE 3

Effect of Different Preparations of Homocyclocreatine on $^3$H-Thymidine Incorporation (Incorporation as a percent of Untreated Control)

| Cell Line | #207 | #235 | #236 |
|---|---|---|---|
| MRC-5 | 100 | 169 | 112 |
| CaSki | 24 | 11 | 4 |
| HeLa | 89 | 74 | 71 |
| U-2 OS | 140 | 34 | 26 |
| Saos-2 | 114 | 72 | 52 |
| Vero | 99 | 79 | 61 |
| 293 | 26 | 7 | 6 |
| PC-3 | 124 | 119 | 118 |
| DU-145 | 94 | 57 | 27 |
| SW403 | 67 | 6 | 7 |
| SW48 | 964 | 234 | 141 |
| BALB/c3T3 | 93 | 11 | 9 |

EXAMPLE 6

Guanidino Compounds with Little or No Effect on Tumor Cell Growth

Ten additional guanidino (i.e., creatine and analogs) compounds were tested for their ability to inhibit growth of a number of cell lines. The structures of the ten compounds tested, references, and sources of purchase are listed in Table 4. In these experiments, the cell lines were exposed to a drug at concentrations from 1 mg/ml to 4 mg/ml for a period of five days. After five days, cells were washed to remove the drug, and growth was assayed by incorporation of $^3$H-thymidine into DNA.

At a concentration of 1 mg/ml, after five days of exposure to drug and under the conditions of the assay, these ten guandidino compounds showed little or no effect on the growth of the cell lines. In most cases, only modest effects on cell growth were observed with the drugs at a concentration of 4 mg/ml (Table 5). In addition, β-guanidino-propionic acid and N-methyl-hydantoic acid inhibited the growth of the non-transformed MRC-5 cell line more strongly than they inhibited growth of many of the transformed cell lines, suggesting that these drugs may not have the desired specificity for tumor cells.

Although colon cell lines SW1116 and SW48 appeared to be strongly inhibited by N-methylhydantoic acid and 1-carboxymethyl-2-iminoimidazolidine-4-one, the control cells appeared to be unhealthy. (As noted above, the colon cell lines are difficult to maintain in tissue culture due to the sensitivity of the cells and possible acidification of the medium.) The values in Table 5 marked "low counts" should be interpreted with caution, because the counts per minute of $^3$H-thymidine incorporated in the control samples were quite low, these values may not be significant.

TABLE 4

GUANIDINO COMPOUNDS (CREATINE AND ANALOGUES) DEMONSTRATING LITTLE OR NO EFFECT ON TUMOR GROWTH UNDER CONDITIONS USED

| Structure | Compound Name | Reference |
|---|---|---|
| 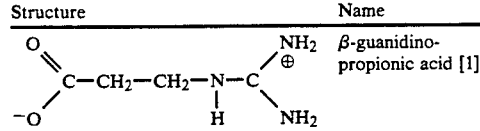 | β-guanidino-propionic acid [1] | G6878 |

TABLE 4-continued
GUANIDINO COMPOUNDS (CREATINE AND ANALOGUES) DEMONSTRATING LITTLE OR NO EFFECT ON TUMOR GROWTH UNDER CONDITIONS USED

| Structure | Compound Name | Reference |
|---|---|---|
| [structure] | N-methyl amidino-N methyl glycine [2] | Rowley, G. L. et al., J. Am. Chem. Soc. 93: 5542-5551 (1971) |
| [structure] | N-ethyl-N-amidino glycine (N-ethyl guanidino acetate) [2] | Richmond, J. J. & Walker, J Arc. Biochem. Biophys. 252: 564–570 (1982) |
| [structure] | N-acetimidoyl-sarcosine [2] | Wang, T., J. Org. Chem. 39: 3591–3594 (1974) |
| [structure] | N-propyl-N-amidino glycine (N-propyl-guanidino acetate) [2] | Rowley, G. L. et al., J. Am. Chem. Soc. 93: 5542-5551 (1971) |
| [structure] | N-methyl-N-amidino-amino methyl phosphonate [2] | Rowley, G. L. et al., J. Am. Chem. Soc. 93: 5542-5551 (1971) |
| [structure] | Creatinine [3] | F820-03 |
| [structure] | 1-carboxymethyl 2-iminoimidazolidine 4-one [2] | Ann Cae Khue Nguyen, Ph.D. Thesis in Pharmaceutical Chem., UCSF (1983) |
| [structure] | 2 methyl-N-carboxymethyl imidazole [2] | Ann Cae Khue Nguyen, Ph.D. Thesis in Pharmaceutical Chem., UCSF (1983) |
| [structure] | N-methyl-hydantoic acid [2] | — |

[1] Sigma
[2] Dalton
[3] Baker

TABLE 5

Effect of Drug on Incorporation of $^3$H-Thymidine
(% of Untreated Control)
Drug (4 mg/ml)

| Amira # | 209 | 210 | 211 | 213 | 260 | 274 | 259 | 261 | 262 | 276 |
|---|---|---|---|---|---|---|---|---|---|---|
| Exp # | 42 | 42 | 42 | 42 | 81 | 81 | 75 | 75 | 75 | 84 |
| Compound | 2-m-N-cmi | 1-cm-2-li-4-o | B·gpa | N-mha | N-ma-N-mg | N-m-N-aamp | N-e-N-ag | N-as | N-p-N-ag | creatinine |
| Cell Line | | | | | | | | | | |
| 293 | 78 | 91 | 85 | 77 | | | | | | |
| Vero | 75 | 83 | 166 | 77 | 97 | 166 | 185 | 115 | 223 | 209 |
| Balb-c 3T3 | 106 | 115 | 130 | 120 | 74 | 117 (2 mg/ml) | 80 | 88 | 73 | 125 |
| C-33A | 105 | 111 | 106 | 96 | | | | | | |
| CaSki | 102 | 106 | 108 | 76 | | | | | | |
| SiHa | 95 | 91 | 108 | 91 | 45 | 66 | 126 | 116 | 133 | 27 |
| HeLa | 107 | 128 | 112 | 169 | | | 88 | 97 | 89 | |
| DU145 | 116 | 111 | 128 | 77 | 121 | 168 | 130 | 148 | 107 | 94 |
| PC3 | 111 | 100 | 119 | 69 | | | 95 | 80 | 86 | |
| LnCAP | 71 | 76 | 77 | 36 | | | | | | |
| SAOS-2 | 98 | 90 | 80 | 68 | | | | | | |
| U2OS | 100 | 101 | 142 | 112 | | | | | | |
| SW1116 | 141 | 0 | 158 | 0 | | | | | | |
| SW48 | 126 | 0 | 131 | 0 | | | | | | |
| SW403 | | | | | | | 120 (172—low counts) | 150 (199—low counts) | 50 (99—low counts) | |
| MRC5 | 103 | 53 | 37 | 34 | | | 113 | 91 | | |
| H69 | 92 | 82 | 98 | 87 | | | | | (130—low counts) | |

Key:
2-m-N-cmi   2-methyl-N-carboxymethylinidazole
1-cm-2-li-4-o   1-carboxymethyl-2-iminoimidazolidine-4-one
B-gpa   Beta gamadinopropionic acid
N-mha   N-methyl-hydantoic acid
N-ma-N-mg   N-methylamidino-N-methylglycine
N-m-N-aamp   N-methyl-N-amidino amino methyl phosphonate
N-e-N-ag   N-ethyl-N-amidinoglycine
N-as   N-acetimidoylsarcosine
N-p-N-ag   N-propyl-N-amidinoglycine
creatinine

CREATINE KINASE B IN OTHER DISEASE ENTITIES

The relationship that has been established between the DNA tumor viruses and CKB, and the ability of creatine kinase inhibitors and creatine analogs to inhibit the growth of transformed cells suggests that these drugs may be very effective anti-tumor agents. Apart from transformation, the viruses themselves may have high energy requirements during infection. In fact, a variety of other viral infections in humans show perturbations of the creatine kinase system. Following influenza infection, many patients develop severe pain in the calf muscle and exhibit an elevated level of creatine kinase and coxsackie B virus titers. Human foreskin fibroblasts exhibit an elevated level of brain creatine kinase during permissive infection with human cytomegalovirus. Children with acute post-infection myositis, with upper respiratory tract and gastrointestinal symptoms, exhibit elevated creatine kinase. Creatine kinase levels increase in viral rhinitis infections and during the acute phase of viral and idiopathic myocarditis. These examples suggest that creatine kinase may provide some essential function during viral infection. Thus, inhibitors of creatine kinase and/or other enzymes which participate in purine and energy metabolism, directly or indirectly, may have antiviral activity against human papilloma viruses, cytomegalovirus, or other viruses.

In the adult, CKB is expressed in the brain and neuronal cells. Interestingly, high levels of creatine kinase are indicated in patients with neurological disorders, including seizures, epilepsy, strokes, meningitis, convulsions and cerebrovascular diseases. Creatine kinase is also activated in malignant hyperthermia, a pharmacogenetic disease in man and animals in which calcium homeostasis is upset, resulting in cellular damage. The disruption of energy balance may be an important component of these diseases or other disorders where CKB is elevated (e.g., psoriasis, arthritis, wound healing). Because some of the creatine kinase inhibitors and creatine analogs can cross the blood brain barrier, they may be suitable candidates for the treatment of neurological disorders. These compounds may even be of use as carriers of toxins or other compounds to the brain.

Equivalents

Those skilled in the art will recognize, or be able to ascertain, using no more than routine experimentation, many equivalents to the specific embodiments of the invention described specifically herein. Such equivalents are intended to be encompassed by the scope of the following claims.

We claim:
1. A method of inhibiting growth or transformation, singly or in combination, of a mammalian cell in which activity of creatine kinase is elevated, comprising contacting the mammalian cell with a drug selected from the group consisting of:
   a) guanidinoacetate;
   b) cyclocreatine;
   c) homocyclocreatine; and
   d) 1-carboxymethyl-2-iminohexahydropyrimidine.
2. A method of inhibiting transformation or growth, singly or in combination, a mammalian cell in which creatine kinase activity is elevated, comprising contacting the mammalian cell with a drug, or a pharmaceutically acceptable salt thereof, selected from the group consisting of:
   a) homocreatine;

b) 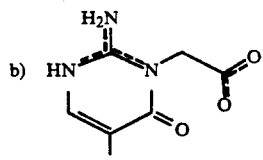

c) 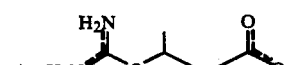

d) 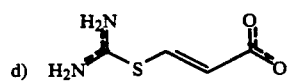

e) 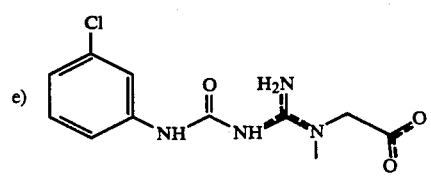

f) 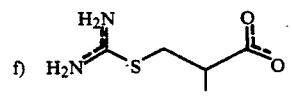

g) 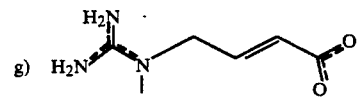

h) 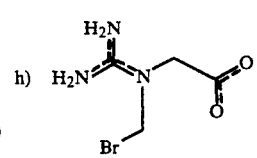

i) 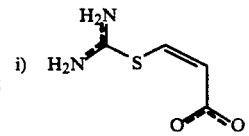

j) D: 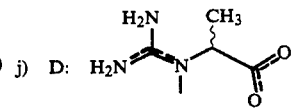

k) L: 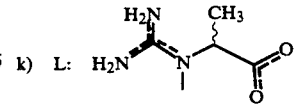

l) 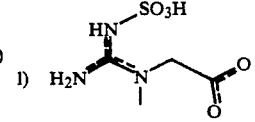

m) 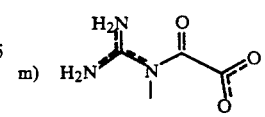

-continued n) 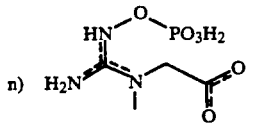

o) E: 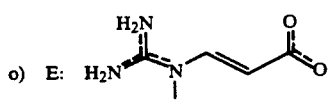

p) Z: 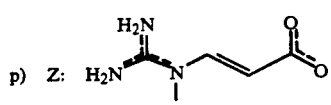

q) 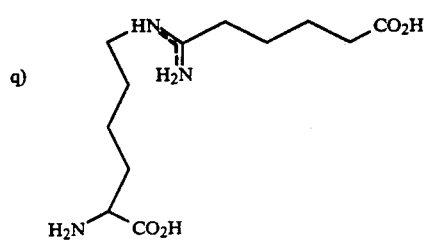

and r) 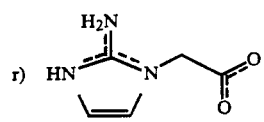

3. A method of inhibiting growth or transformation, singly or in combination, of a mammalian cell in which activity of creatine kinase is elevated, comprising administering to a mammal a drug selected from the group consisting of:
a) guanidinoacetate;
b) cyclocreatine;
c) homocyclocreatine; and
d) 1-carboxymethyl-2-iminohexahydropyrimidine.

4. A method for inhibiting growth of a tumor cell, comprising: contacting a tumor cell with a drug selected from the group consisting of:
a) guanidinoacetate;
b) cyclocreatine;
c) homocyclocreatine; and
d) 1-carboxymethyl-2-iminohexahydropyrimidine.

5. The method for inhibiting growth of a tumor cell of claim 4 wherein the drug is guanidinoacetate.

6. The method for inhibiting growth of a tumor cell of claim 4 wherein the drug is cyclocreatine.

7. The method for inhibiting growth of a tumor cell of claim 4 wherein the drug is homocyclocreatine.

8. The method for inhibiting growth of a tumor cell of claim 4 wherein the drug is 1-carboxymethyl-2-iminohexahydropyrimidine.

9. A method for inhibiting growth of a tumor cell, comprising: contacting a tumor cell with a drug of the general formula:

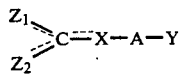

and pharmaceutically acceptable salts thereof, wherein:

(a) Y is selected from the group consisting of: $-CO_2H$, $-NHOH$, $-NO_2$, $-SO_3H$, $-C(=O)N-HSO_2J$ and $-P(=O)(OH)(OJ)$, wherein J is selected from the group consisting of: hydrogen, $C_1-C_6$ straight chain alkyl, $C_3-C_6$ branched alkyl, $C_2-C_6$ straight alkenyl, $C_3-C_6$ branched alkenyl and aryl;

(b) A is selected from the group consisting of: C, CH, $C_1-C_5$ alkyl, $C_2-C_5$ alkenyl, $C_2-C_5$ alkynyl, and $C_1-C_5$ alkoyl, each having 0–2 substituents which are selected independently from the group consisting of:

(1) K, where K is selected from the group consisting of: $C_1-C_6$ straight alkyl, $C_2-C_6$ straight alkenyl, $C_1-C_6$ straight alkoyl, $C_3-C_6$ branched alkyl, $C_3-C_6$ branched alkenyl, $C_4-C_6$ branched alkoyl, K having 0–2 substituents independently selected from the group consisting of: bromo, chloro, epoxy and acetoxy;

(2) an aryl group selected from the group consisting of: a 1–2 ring carbocycle and a 1–2 ring heterocycle, wherein the aryl group contains 0–2 substituents independently selected from the group consisting of: $-CH_2L$ and $-COCH_2L$ where L is independently selected from the group consisting of: bromo, chloro, epoxy and acetoxy; and (3) $-NH-M$, wherein M is selected from the group consisting of: hydrogen, $C_1-C_4$ alkyl, $C_2-C_4$ alkenyl, $C_1-C_4$ alkoyl, $C_3-C_4$ branched alkyl, $C_3-C_4$ branched alkenyl, and $C_4-C_6$ branched alkoyl;

(c) X is selected from the group consisting of: $NR_1$, $CHR_1$, $CR_1$, O and S, wherein $R_1$ is selected from the group consisting of (1) hydrogen;

(2) K where K is selected from the group consisting of: $C_1-C_6$ straight alkyl, $C_2-C_6$ straight alkenyl, $C_1-C_6$ straight alkoyl, $C_3-C_6$ branched alkyl, $C_3-C_6$ branched alkenyl, and $C_4-C_6$ branched alkoyl, K having 0–2 substituents independently selected from the group consisting of: bromo, chloro, epoxy and acetoxy;

(3) an aryl group selected from the group consisting of: a 1–2 ring carbocycle and a 1–2 ring heterocycle, wherein the aryl group contains 0–2 substituents independently selected from the group consisting of: $-CH_2L$ and $-COCH_2L$ where L is independently selected from the group consisting of: bromo, chloro, epoxy and acetoxy;

(4) a $C_5-C_9$ α-amino-ω-methyl-ω-adenosylcarboxylic acid attached via the ω-methyl carbon;

(5) a $C_5-C_9$ α-amino-ω-aza-ω-methyl-ω-adenosylcarboxylic acid attached via the ω-methyl carbon; and (6) a $C_5-C_9$ α-amino-ω-thia-ω-methyl-ω-adenosylcarboxylic wherein A and X are connected by a single or double bond;

(d) $Z_1$ and $Z_2$ are chosen independently from the group consisting of: $=O$, $-NHR_2$, $-CH_2R_2$, $-NR_2OH$; wherein, $Z_1$ and $Z_2$ may not both be $=O$ and wherein $R_2$ is selected from the group consisting of:

(1) hydrogen;

(2) K, where K is selected from the group consisting of: $C_1-C_6$ straight alkyl, $C_2-C_6$ straight alkenyl, $C_1$-$C_6$straight alkoyl, $C_3$-$C_6$branched alkyl, $C_3$-$C_6$branched alkenyl, and $C_4$-$C_6$branched alkoyl, K having 0-2 substituents independently selected from the group consisting of bromo, chloro, epoxy and acetoxy;

(3) an aryl group selected from the group consisting of: a 1-2 ring carbocycle and a 1-2 ring heterocycle, wherein the aryl group contains 0-2 substituents independently selected from the group consisting of: —$CH_2L$ and —$COCH_2L$ where L is independently selected from the group consisting of: bromo, chloro, epoxy and acetoxy;

(4) a $C_4$-$C_8\alpha$-amino-carboxylic acid attached via the $\omega$-carbon;

(5) B, wherein B is selected from the group consisting of: —$CO_2H$, —NHOH, —$NO_2$, —$SO_3H$, —C(=O)$NHSO_2J$ and —P(=O)(OH)(OJ), wherein J is selected from the group consisting of: hydrogen $C_1$-$C_6$straight alkyl, $C_3$-$C_6$branched alkyl, $C_2$-$C_6$straight alkenyl, $C_3$-$C_6$branched alkenyl and aryl; wherein B is optionally connected to the nitrogen via a linker selected from the group consisting of: $C_1$-$C_2$alkyl, $C_2$alkenyl, and $C_1$-$C_2$alkoyl;

(6) —D—E, wherein D is selected from the group consisting of: $C_1$-$C_3$ straight chain alkyl, $C_3$ branched alkyl, $C_2$-$C_3$ straight alkenyl, $C_3$ branched alkenyl, $C_1$-$C_3$ straight alkoyl, and aryl; and E is selected from the group consisting of: —$(PO_3)_n$NMP, where n is 0-2 and NMP is a ribonucleotide monophosphate connected via the 5'-phosphate, 3'-phosphate or the aromatic ring of the base; —[P(=O)($OCH_3$)(O)]$_m$—Q, wherein m is 0-3 and Q is a ribonucleoside connected via the ribose or the aromatic ring of the base; —[P(=O)(OH)($CH_2$)]$_m$—Q, where m is 0-3 and Q is a ribonucleoside connected via the ribose of the aromatic ring of the base; and an aryl group containing 0-3 substituents chosen independently from the group consisting of: Cl, Br, epoxy, acetoxy, —OG, —C(=O)G, and —$CO_2G$, where G is independently selected from the group consisting of: $C_1$-$C_6$straight alkyl, $C_2$-$C_6$straight alkenyl, $C_1$-$C_6$straight alkoyl, $C_3$-$C_6$branched alkyl, $C_1$-$C_6$branched alkenyl, $C_4$-$C_6$branched alkoyl; wherein E may be attached at any point to D, and
if D is alkyl or alkenyl, D may be connected at either or both ends by an amide linkage; and (7) —E, wherein E is selected from the group consisting of: —$(PO_3)_n$NMP, where n is 0-2 and NMP is a ribonucleotide monophosphate connected via the 5'-phosphate, 3'-phosphate or the aromatic ring of the base; —P[P(=O)($OCH_3$)(O)]$_m$—Q, wherein m is 0-3 and Q is a ribonucleoside connected via the ribose or the aromatic ring of the base; —[P(=O)(OH)($CH_2$)]$_m$—Q, wherein m is 0-3 and Q is a ribonucleoside connected via the ribose of the aromatic ring of the base; and an aryl group containing 0-3 substituents chosen independently from the group consisting of: Cl, Br, epoxy, acetoxy, —OG, —C(=O)G, and —$CO_2G$, where G is independently selected from the group consisting of: $C_1$-$C_6$straight alkyl, $C_2$-$C_6$straight alkenyl, $C_1$-$C_6$straight alkoyl; $C_3$-$C_6$branched alkyl, $C_3$-$C_6$branched alkenyl, $C_4$-$C_6$branched alkoyl; and if E is aryl, E may be connected by an amide linkage;

(e) if $R_1$ and at least one $R_2$ group are present, $R_1$ may be connected by a single or double bond to an $R_2$ group to form a cycle of 5 to 7 members, (f) is two $R_2$ groups are present, they may be connected by a single or double bond to form a cycle of 5 to 7 members; and (g) if $R_1$ is present and $Z_1$ or $Z_2$ is selected from the group consisting of —$NHR_2$, —$CH_2R_2$ and —$NR_2OH$, then $R_1$ may be connected by a single or double bond to the carbon or nitrogen of either $Z_1$ or $Z_2$ to form a cycle of 4 to 7 members.

10. A method for inhibiting growth of a tumor cell, comprising: contacting a tumor cell with a drug selected from the group consisting of:

a) homocreatine;

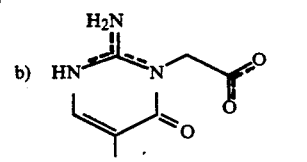

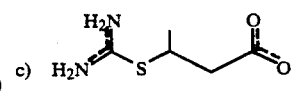

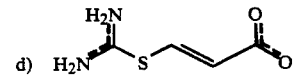

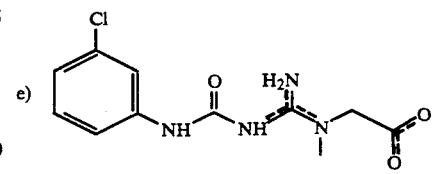

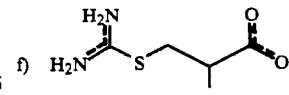

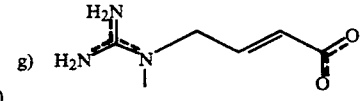

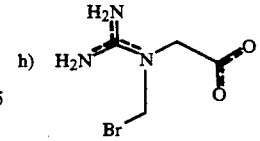

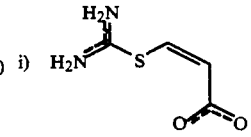

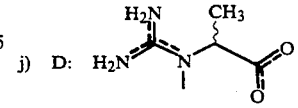

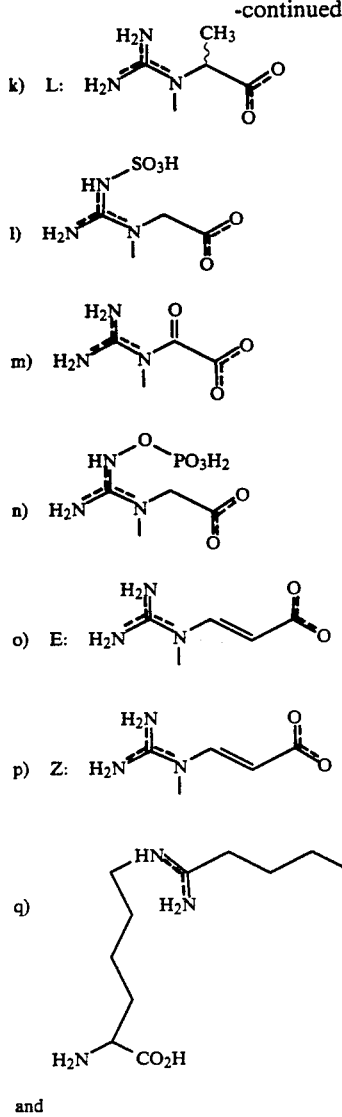

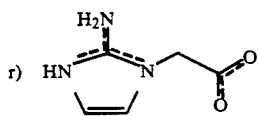

and

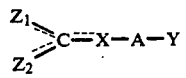

11. A method for inhibiting growth of a tumor cell, comprising: administering a drug to a mammal such that growth of a tumor cell is inhibited, the drug being selected from the group consisting of:
a) guanidinoacetate;
b) cyclocreatine;
c) homocyclocreatine; and
d) 1-carboxymethyl-2-iminohexahydropyrimidine.

12. The method of inhibiting growth of a tumor cell of claim 11, wherein the drug is guanidinoacetate.

13. The method of inhibiting growth of a tumor cell of claim 11, wherein the drug is cyclocreatine.

14. The method of inhibiting growth of a tumor cell of claim 11, wherein the drug is homocyclocreatine.

15. The method of inhibiting growth of a tumor cell of claim 11, wherein the drug is 1-caroboxymethyl-2-iminohexahydropyrimidine.

16. A method for inhibiting growth of a tumor cell, comprising: administering a drug to a mammal such that growth of a tumor cell is inhibited, the drug being of the general formula:

$$\begin{matrix} Z_1 \\ \phantom{Z}\searrow \\ \phantom{ZZZ}C=X-A-Y \\ \phantom{Z}\nearrow \\ Z_2 \end{matrix}$$

and pharmaceutically acceptable salts thereof, wherein:
(a) Y is selected from the group consisting of: —$CO_2H$, —NHOH, —$NO_2$, —$SO_3H$, —C(=O)N-HSO$_2$J and —P(=O)(OH)(OJ), wherein J is selected from the group consisting of: hydrogen, $C_1$-$C_6$ straight chain alkyl, $C_3$-$C_6$ branched alkyl, $C_2$-$C_6$ straight alkenyl, $C_3$-$C_6$ branched alkenyl and aryl;
(b) A is selected from the group consisting of: C, CH, $C_1$-$C_5$alkyl, $C_2$-$C_5$alkenyl, $C_2$-$C_5$alkynyl, and $C_1$-$C_5$alkoyl, each having 0-2 substituents which are selected independently from the group consisting of:
(1) K, where K is selected from the group consisting of: $C_1$-$C_6$straight alkyl, $C_2$-$C_6$straight alkenyl, $C_1$-$C_6$straight alkoyl, $C_3$-$C_6$branched alkyl, $C_3$-$C_6$branched alkenyl, $C_4$-$C_6$branched alkoyl, K having 0-2 substituents independently selected from the group consisting of: bromo, chloro, epoxy and acetoxy;
(2) an aryl group selected from the group consisting of: a 1-2 ring carbocycle and a 1-2 ring heterocycle, wherein the aryl group contains 0-2 substituents independently selected from the group consisting of: —$CH_2L$ and —$COCH_2L$ where L is independently selected from the group consisting of: bromo, chloro, epoxy and acetoxy; and
(3) —NH—M, wherein M is selected from the group consisting of: hydrogen, $C_1$-$C_4$ alkyl, $C_2$-$C_4$ alkenyl, $C_1$-$C_4$ alkoyl, $C_3$-$C_4$ branched alkyl, $C_3$-$C_4$ branched alkenyl, and $C_4$-$C_6$branched alkoyl;
(c) X is selected from the group consisting of: $NR_1$, $CHR_1$, $CR_1$, O and S, wherein $R_1$ is selected from the group consisting of
(1) hydrogen;
(2) K where K is selected from the group consisting of: $C_1$-$C_6$straight alkyl, $C_2$-$C_6$straight alkenyl, $C_1$-$C_6$straight alkoyl, $C_3$-$C_6$branched alkyl, $C_3$-$C_6$branched alkenyl, and $C_4$-$C_6$branched alkoyl, K having 0-2 substituents independently selected from the group consisting of: bromo, chloro, epoxy and acetoxy;
(3) an aryl group selected from the group consisting of: a 1-2 ring carbocycle and a 1-2 ring heterocycle, wherein the aryl group contains 0-2 substituents independently selected from the group consisting of: —$CH_2L$ and —$COCH_2L$ where L is independently selected from the group consisting of: bromo, chloro, epoxy and acetoxy;
(4) a $C_5$-$C_9$ αamino-ω-methyl-ω-adenosylcarboxylic acid attached via the ω-methyl carbon;
(5) a $C_5$-$C_9$α-amino-ω-aza-ω-methyl-ω-adenosylcarboxylic acid attached via the ω-methyl carbon; and
(6) a $C_5$-$C_9$α-amino-ω-thia-ω-methyl-ω-adenosylcarboxylic wherein A and X are connected by a single or double bond;

(d) $Z_1$ and $Z_2$ are chosen independently from the group consisting of: =O, —$NHR_2$, —$CH_2R_2$, —$NR_2OH$; wherein, $Z_1$ and $Z_2$ may not both be =O and wherein $R_2$ is selected from the group consisting of:
(1) hydrogen;
(2) K, where K is selected from the group consisting of: $C_1$-$C_6$straight alkyl, $C_2$-$C_6$straight alkenyl, $C_1$-$C_6$straight alkoyl, $C_3$-$C_6$branched alkyl, $C_3$-$C_6$branched alkenyl, and $C_4$-$C_6$branched alkoyl, K having 0-2 substituents independently selected from the group consisting of bromo, chloro, epoxy and acetoxy;
(3) an aryl group selected from the group consisting of: a 1-2 ring carbocycle and a 1-2 ring heterocycle, wherein the aryl group contains 0-2 substituents independently selected from the group consisting of: —$CH_2L$ and —$COCH_2L$ where L is independently selected from the group consisting of: bromo, chloro, epoxy and acetoxy;
(4) a $C_4$-$C_8$α-amino-carboxylic acid attached via the ω-carbon;
(5) B, wherein B is selected from the group consisting of: —$CO_2H$, —NHOH, —$NO_2$, —$SO_3H$, —C(=O)$NHSO_2J$ and —P(=O)(OH)(OJ), wherein J is selected from the group consisting of: hydrogen $C_1$-$C_6$straight alkyl, $C_3$-$C_6$branched alkyl, $C_2$-$C_6$straight alkenyl, $C_3$-$C_6$branched alkenyl and aryl; wherein B is optionally connected to the nitrogen via a linker selected from the group consisting of: $C_1$-$C_2$alkyl, $C_2$alkenyl, and $C_1$-$C_2$alkoyl;
(6) —D—E, wherein D is selected from the group consisting of: $C_1$-$C_3$ straight chain alkyl, $C_3$ branched alkyl, $C_2$-$C_3$ straight alkenyl, $C_3$ branched alkenyl, $C_1$-$C_3$ straight alkoyl, and aryl; and E is selected from the group consisting of: —$(PO_3)_n$NMP, where n is 0-2 and NMP is a ribonucleotide monophosphate connected via the 5'-phosphate, 3'-phosphate or the aromatic ring of the base; —[P(=O)($OCH_3$)(O)]$_m$—Q, wherein m is 0-3 and Q is a ribonucleoside connected via the ribose or the aromatic ring of the base; —[P(=O)(OH)($CH_2$)]$_m$—Q, where m is 0-3 and Q is a ribonucleoside connected via the ribose of the aromatic ring of the base; and an aryl group containing 0-3 substituents chosen independently from the group consisting of: Cl, Br, epoxy, acetoxy, —OG, —C(=O)G, and —$CO_2G$, where G is independently selected from the group consisting of: $C_1$-$C_6$straight alkyl, $C_2$-$C_6$straight alkenyl, $C_1$-$C_6$straight alkoyl, $C_3$-$C_6$branched alkyl, $C_1$-$C_6$branched alkenyl, $C_4$-$C_6$branched alkoyl; wherein E may be attached at any point to D, and
if D is alkyl or alkenyl, D may be connected at either or both ends by an amide linkage; and
(7) —E, wherein E is selected from the group consisting of: —$(PO_3)_n$NMP, where n is 0-2 and NMP is a ribonucleotide monophosphate connected via the 5'-phosphate, 3'-phosphate or the aromatic ring of the base; —P[P(=O)($OCH_3$)(O)]$_m$—Q, where m is 0-3 and Q is a ribonucleoside connected via the ribose or the aromatic ring of the base; —[P(=O)(OH)($CH_2$)]$_m$—Q, wherein m is 0-3 and Q is a ribonucleoside connected via the ribose of the aromatic ring of the base; and an aryl group containing 0-3 substituents chosen independently from the group consisting of: Cl, Br, epoxy, acetoxy, —OG, —C(=O)G, and —$CO_2G$, where G is independently selected from the group consisting of: $C_1$-$C_6$straight alkyl, $C_2$-$C_6$straight alkenyl, $C_1$-$C_6$straight alkoyl; $C_3$-$C_6$branched alkyl, $C_3$-$C_6$branched alkenyl, $C_4$-$C_6$branched alkoyl; and if E is aryl, E may be connected by an amide linkage;

(e) if $R_1$ and at least one $R_2$ group are present, $R_1$ may be connected by a single or double bond to an $R_2$ group to form a cycle of 5 to 7 members,
(f) is two $R_2$ groups are present, they may be connected by a single or double bond to form a cycle of 5 to 7 members; and
(g) if $R_1$ is present and $Z_1$ or $Z_2$ is selected from the group consisting of —$NHR_2$, —$CH_2R_2$ and —$NR_2OH$, then $R_1$ may be connected by a single or double bond to the carbon or nitrogen of either $Z_1$ or $Z_2$ to form a cycle of 4 to 7 members.

17. A method of inhibiting transformation or growth, singly or in combination, of a mammalian cell in which creatine kinase activity is elevated, comprising contacting the mammalian cell with a drug of the general formula:

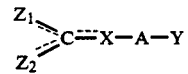

and pharmaceutically acceptable salts thereof, thereby inhibiting growth or transformation, wherein:
(a) Y is selected from the group consisting of: —$CO_2H$, —NHOH, —$NO_2$, —$SO_3H$, —C(=O)$NHSO_2J$ and —P(=O)(OH)(OJ), wherein J is selected from the group consisting of: hydrogen, $C_1$-$C_6$straight chain alkyl, $C_3$-$C_6$branched alkyl, $C_2$-$C_6$straight alkenyl, $C_3$-$C_6$branched alkenyl and aryl;
(b) A is selected from the group consisting of: C, CH, $C_1$-$C_5$alkyl, $C_2$-$C_5$alkenyl, $C_2$-$C_5$alkynyl, and $C_1$-$C_5$alkoyl, each having 0-2 substituents which are selected independently from the group consisting of:
(1) K, where K is selected from the group consisting of: $C_1$-$C_6$straight alkyl, $C_2$-$C_6$straight alkenyl, $C_1$-$C_6$straight alkoyl, $C_3$-$C_6$branched alkyl, $C_3$-$C_6$branched alkenyl, $C_4$-$C_6$branched alkoyl, K having 0-2 substituents independently selected from the group consisting of: bromo, chloro, epoxy and acetoxy;
(2) an aryl group selected from the group consisting of: a 1-2 ring carbocycle and a 1-2 ring heterocycle, wherein the aryl group contains 0-2 substituents independently selected from the group consisting of: —$CH_2L$ and —$COCH_2L$ where L is independently selected from the group consisting of: bromo, chloro, epoxy and acetoxy; and
(3) —NH—M, wherein M is selected from the group consisting of: hydrogen, $C_1$-$C_4$ alkyl, $C_2$-$C_4$ alkenyl, $C_1$-$C_4$ alkoyl, $C_3$-$C_4$ branched alkyl, $C_3$-$C_4$ branched alkenyl, and $C_4$-$C_6$branched alkoyl;

(a) Y is selected from the group consisting of: —$CO_2H$, —NHOH, —$NO_2$, —$SO_3H$, —C(=O)NH$SO_2$J and —P(=O)(OH)(OJ), wherein J is selected from the group consisting of: hydrogen, $C_1$-$C_6$straight chain alkyl, $C_3$-$C_6$branched alkyl, $C_2$-$C_6$straight alkenyl, $C_3$-$C_6$branched alkenyl and aryl;

(b) A is selected from the group consisting of: C, CH, $C_1$-$C_5$alkyl, $C_2$-$C_5$alkenyl, $C_2$-$C_5$alkynyl, and $C_1$-$C_5$alkoyl, each having 0-2 substituents which are selected independently from the group consisting of:

(1) K, where K is selected from the group consisting of: $C_1$-$C_6$straight alkyl, $C_2$-$C_6$straight alkenyl, $C_1$-$C_6$straight alkoyl, $C_3$-$C_6$branched alkyl, $C_3$-$C_6$branched alkenyl, $C_4$-$C_6$branched alkoyl, K having 0-2 substituents independently selected from the group consisting of: bromo, chloro, epoxy and acetoxy;

(2) an aryl group selected from the group consisting of: a 1-2 ring carbocycle and a 1-2 ring heterocycle, wherein the aryl group contains 0-2 substituents independently selected from the group consisting of: —$CH_2L$ and —$COCH_2L$ where L is independently selected from the group consisting of: bromo, chloro, epoxy and acetoxy; and (3) —NH—M, wherein M is selected from the group consisting of: hydrogen, $C_1$-$C_4$ alkyl, $C_2$-$C_4$ alkenyl, $C_1$-$C_4$ alkoyl, $C_3$-$C_4$ branched alkyl, $C_3$-$C_4$ branched alkenyl, and $C_4$-$C_6$branched alkoyl;

(c) X is selected from the group consisting of: $NR_1$, $CHR_1$, $CR_1$, O and S, wherein $R_1$ is selected from the group consisting of (1) hydrogen;

(2) K where K is selected from the group consisting of: $C_1$-$C_6$straight alkyl, $C_2$-$C_6$straight alkenyl, $C_1$-$C_6$straight alkoyl, $C_3$-$C_6$branched alkyl, $C_3$-$C_6$branched alkenyl, and $C_4$-$C_6$branched alkoyl, K having 0-2 substituents independently selected from the group consisting of: bromo, chloro, epoxy and acetoxy;

(3) an aryl group selected from the group consisting of: a 1-2 ring carbocycle and a 1-2 ring heterocycle, wherein the aryl group contains 0-2 substituents independently selected from the group consisting of: —$CH_2L$ and —$COCH_2L$ where L is independently selected from the group consisting of: bromo, chloro, epoxy and acetoxy;

(4) a $C_5$-$C_9$ αamino-ω-methyl-ω-adenosylcarboxylic acid attached via the ω-methyl carbon;

(5) a $C_5$-$C_9$α-amino-ω-aza-ω-methyl-ω-adenosylcarboxylic acid attached via the ω-methyl carbon; and (6) a $C_5$-$C_9$α-amino-ω-thia-ω-methyl-ω-adenosylcarboxylic wherein A and X are connected by a single or double bond;

(d) $Z_1$ and $Z_2$ are chosen independently from the group consisting of: =O, —$NHR_2$, —$CH_2R_2$, —$NR_2OH$; wherein, $Z_1$ and $Z_2$ may not both be =O and wherein $R_2$ is selected from the group consisting of:

(1) hydrogen;

(2) K, where K is selected from the group consisting of: $C_1$-$C_6$straight alkyl, $C_2$-$C_6$straight alkenyl, $C_1$-$C_6$straight alkoyl, $C_3$-$C_6$branched alkyl, $C_3$-$C_6$branched alkenyl, and $C_4$-$C_6$branched alkoyl, K having 0-2 substituents independently selected from the group consisting of: bromo, chloro, epoxy and acetoxy;

(3) an aryl group selected from the group consisting of: a 1-2 ring carbocycle and a 1-2 ring heterocycle, wherein the aryl group contains 0-2 substituents independently selected from the group consisting of: —$CH_2L$ and —$COCH_2L$ where L is independently selected from the group consisting of: bromo, chloro, epoxy and acetoxy;

(4) a $C_4$-$C_8$α-amino-carboxylic acid attached via the ω-carbon;

(5) B, wherein B is selected from the group consisting of: —$CO_2H$, —NHOH, —$NO_2$, —$SO_3H$, —C(=O)$NHSO_2$J and —P(=O)(OH)(OJ), wherein J is selected from the group consisting of: hydrogen $C_1$-$C_6$straight alkyl, $C_3$-$C_6$branched alkyl, $C_2$-$C_6$straight alkenyl, $C_3$-$C_6$branched alkenyl and aryl; wherein B is optionally connected to the nitrogen via a linker selected from the group consisting of: $C_1$-$C_2$alkyl, $C_2$alkenyl, and $C_1$-$C_2$alkoyl;

(6) —D—E, wherein D is selected from the group consisting of: $C_1$-$C_3$ straight chain alkyl, $C_3$ branched alkyl, $C_2$-$C_3$ straight alkenyl, $C_3$ branched alkenyl, $C_1$-$C_3$ straight alkoyl, and aryl; and E is selected from the group consisting of: —($PO_3$)$_n$NMP, where n is 0-2 and NMP is a ribonucleotide monophosphate connected via the 5'-phosphate, 3'-phosphate or the aromatic ring of the base; —[P(=O)($OCH_3$)(O)]$_m$—Q, wherein m is 0-3 and Q is a ribonucleoside connected via the ribose or the aromatic ring of the base; —[P(=O)(OH)($CH_2$)]$_m$—Q, where m is 0-3 and Q is a ribonucleoside connected via the ribose of the aromatic ring of the base; and an aryl group containing 0-3 substituents chosen independently from the group consisting of: Cl, Br, epoxy, acetoxy, —OG, —C(=O)G, and —$CO_2$G, where G is independently selected from the group consisting of: $C_1$-$C_6$straight alkyl, $C_2$-$C_6$straight alkenyl, $C_1$-$C_6$straight alkoyl, $C_3$-$C_6$branched alkyl, $C_1$-$C_6$branched alkenyl, $C_4$-$C_6$branched alkoyl; wherein E may be attached at any point to D, and if D is alkyl or alkenyl, D may be connected at either or both ends by an amide linkage; and (7) —E, wherein E is selected from the group consisting of: —($PO_3$)$_n$NMP, where n is 0-2 and NMP is a ribonucleotide monophosphate connected via the 5'-phosphate, 3'-phosphate or the aromatic ring of the base; —P[P(=O)($OCH_3$)(O)]$_m$—Q, where m is 0-3 and Q is a ribonucleoside connected via the ribose or the aromatic ring of the base; —[P(=O)(OH)($CH_2$)]$_m$—Q, wherein m is 0-3 and Q is a ribonucleoside connected via the ribose of the aromatic ring of the base; and an aryl group containing 0-3 substituents chosen independently from the group consisting of: Cl, Br, epoxy, acetoxy, —OG, —C(=O)G, and —$CO_2$G, where G is independently selected from the group consisting of: $C_1$-$C_6$straight alkyl, $C_2$-$C_6$straight alkenyl, $C_1$-$C_6$straight alkoyl; $C_3$-$C_6$branched alkyl, $C_3$-$C_6$branched alkenyl, $C_4$-$C_6$branched alkoyl; and if E is aryl, E may be connected by an amide linkage;

(e) if $R_1$ and at least one $R_2$ group are present, $R_1$ may be connected by a single or double bond to an $R_2$ group to form a cycle of 5 to 7 members, (f) is two $R_2$ groups are present, they may be connected by a single or double bond to form a cycle of 5 to 7 members; and (g) if $R_1$ is present and $Z_1$ or $Z_2$ is selected from the group consisting of $-NHR_2$, $-CH_2R_2$ and $-NR_2OH$, then $R_1$ may be connected by a single or double bond to the carbon or nitrogen of either $Z_1$ or $Z_2$ to form a cycle of 4 to 7 members.

* * * * *